United States Patent [19]
Civin et al.

[11] Patent Number: 5,705,625
[45] Date of Patent: Jan. 6, 1998

[54] NUCLEIC ACID ENCODING NOVEL PROTEIN TYROSINE KINASE

[75] Inventors: Curt I. Civin; Donald Small; Meredith G. Safford, all of Baltimore, Md.

[73] Assignee: The Johns Hopkins University School of Medicine, Baltimore, Md.

[21] Appl. No.: 357,598

[22] Filed: Dec. 15, 1994

[51] Int. Cl.$^6$ .......................... C12N 15/09; C12N 15/52
[52] U.S. Cl. .................. 536/23.5; 435/691; 435/194; 435/252.3; 435/254.11; 435/320.1; 435/325
[58] Field of Search .................. 435/69.1, 240.2, 435/252.3, 254.11, 320.1, 325, 194; 536/23.5

[56] References Cited
PUBLICATIONS

Silvennoinen, Proc. Natl. Acad. Sci. vol. 90, pp 8429–8433, 1993.
Sambrook et al., Molecular Cloning, A Laboratory Manual Second Edition, vol.3, 16.2–16.30, 17.2–17.28 1989 Cold Spring Harbor Laboratory Press, CSH.

*Primary Examiner*—Stephen Walsh
*Assistant Examiner*—Sally P. Teng
*Attorney, Agent, or Firm*—Fish & Richardson, P.C.

[57] ABSTRACT

A novel protein tyrosine kinase, JAK3, and a polynucleotide sequence encoding JAK3 polypeptide are disclosed herein. JAK3 is a new member of the JAK family of protein tyrosine kinases which are important in regulation of cellular proliferation and differentiation. Also disclosed are therapeutic methods utilizing JAK3 polypeptide and polynucleotide sequences.

5 Claims, 13 Drawing Sheets

```
              AAACAGTTAATACATATTTTTTATGTTACGTGTATTCTGTACAACAA
         AGTAAGCTAGACAAAAGAAAATGTTTTCTCCTTCCTGTGTGGACTTTCCTCTCGCTGCC
         TCCCGGCTCTGCCCGCCCTTCGAAAGTCCAGGGTCCCTGCCCGCTAGGCAAGTTGCACTC
  1    M  A  P  P  S  E  E  T  P  L  I  P  Q  R  S  C  S  L  L  S
         ATGGCACCTCCAAGTGAAGAGACGCCCCTGATCCCTCAGCGTTCATGCAGCCTCTTGTCC        60
  21   T  E  A  G  A  L  H  V  L  L  P  A  R  G  P  G  P  P  Q  R
         ACGGAGGCTGGTGCCCTGCATGTGCTGCTGCCCGCTCGGGGCCCCGGCCCCCCCAGCGC       120
  41   L  S  F  S  F  G  D  H  L  A  E  D  L  C  V  Q  A  A  K  A
         CTATCTTTCTCCTTTGGGGACCACTTGGCTGAGGACCTGTGCGTGCAGGCTGCCAAGGCC       180
  61   S  A  I  L  P  V  Y  H  S  L  F  A  L  A  T  E  D  L  S  C
         AGCGCGATCCTGCCTGTGTACCACTCCCTCTTTGCTCTGGCCACGGAGGACCTGTCCTGC       240
  81   W  F  P  R  A  T  S  S  P  W  R  M  P  A  P  Q  V  L  L  Y
         TGGTTCCCCCGAGCCACATCTTCTCCGTGGAGGATGCCAGCACCCCAAGTCCTGCTGTAC       300
 101   R  I  R  P  Y  F  P  N  W  F  G  L  E  K  C  H  R  F  G  L
         AGGATTCGCTTTTACTTCCCCAATTGGTTTGGGCTGGAGAAGTGCCACCGCTTCGGGCTA       360
 121   R  K  D  L  A  S  A  I  L  D  L  P  V  L  E  H  L  F  A  Q
         CGCAAGGATTTGGCCAGTGCTATCCTTGACCTGCCAGTCCTGGAGCACCTCTTTGCCCAG       420
 141   H  R  S  D  L  V  S  G  R  L  P  R  G  L  S  L  K  E  Q  G
         CACCGCAGTGACCTGGTGAGTGGGCGCCTCCCCGTGGCCTCAGTCTCAAGGAGCAGGGT       480
 161   E  C  L  S  L  A  V  L  D  L  A  R  M  A  R  E  Q  A  Q  R
         GAGTGTCTCAGCCTGGCCGTGTTGGACCTGGCCCGGATGGCGCGAGAGCAGGCCCAGCGG       540
 181   R  G  E  L  L  K  T  V  S  Y  K  A  C  L  P  P  S  L  R  D
         CGGGAGAGCTGCTGAAGACTGTCAGCTACAAGGCCTGCCTACCCCCAAGCCTGCGCGAC       600
 201   L  I  Q  G  L  S  F  V  T  G  R  R  I  R  R  T  V  E  S  P
         CTGATCCAGGGCCTGAGCTTCGTGACGGGGAGGCGTATTCGGAGGACGGTGGAGAGCCCC       660
 221   L  R  R  V  A  A  C  Q  A  D  R  H  S  L  M  A  K  Y  I  M
         CTGCGCCGGGTGGCCGCCTGCCAGGCAGACCGGCACTCGCTCATGGCCAAGTACATCATG       720
 241   D  L  E  R  L  D  P  A  G  A  A  E  T  F  H  V  G  L  P  G
         GACCTGGAGCGGCTGGATCCAGCCGGGGCCGCCGAGACCTTCCACGTGGGCCTCCCTGGG       780
 261   A  L  G  G  H  D  G  L  G  L  V  R  V  A  G  D  G  G  I  A
         GCCCTTGGTGGCCACGACGGGCTGGGGCTCGTCCGCGTGGCTGGTGACGGCGGCATCGCC       840
```

```
                                AAACAGTTAATACATATTTTTATGTTACGTGTATTCTGTACAACAA          60
     AGTAAGCTAGACAAAGAAAATGTTTTCCTCCTGTGGGACTTTCCTCTGCTGCC                              120
     TCCCGGCTCTGCCCCGCCTTCCAAGTGCCCCTAGCCAAGTTGCACTC                                    180
  1  M  A  P  P  S  E  E  T  P  L  I  P  Q  R  S  C  S  L  L  S
     ATGGCACCTCCAAGTGAAGAGACGCCCCTGATCCCTCAGCGTTCATGCAGCCTCTTGTCC                       240
 21  T  E  A  G  A  L  H  V  L  L  P  A  R  G  P  P  Q  R
     ACGGAGGCTGGTGCCCTGCATGTCCTGCTGCCCGCGCGGGGCCCCCCCAGGC                               300
 41  L  S  F  S  F  G  D  H  L  A  E  D  L  C  V  Q  A  A  K  A
     CTATCTTTCTCCTTTGGGGACCACTTGGCTGAGGACCTGTGCGTGCAGGCTGCCAAGGCC                       360
 61  S  A  I  L  P  V  Y  H  S  L  F  A  L  A  T  E  D  L  S  C
     AGCGCGATCCTGCCTGTATACCACTCCCTTTGCTCTGGCACGGAGGACCTGTCCTGC                          420
 81  W  F  P  R  A  T  S  S  P  W  R  M  P  A  P  Q  V  L  L  Y
     TGGTTCCCCCGAGCCACATCTTCTCCGTGGAGGATGCCAGCCAAGTCCTGCTGTAC                           480
101  R  I  R  P  Y  F  P  N  W  F  G  L  E  K  C  H  R  F  G  L
     AGGATTCGCCTTTTACTCCCAATGGTTTGGGCTGGAGAAGTGCCACCGCTTCGGGCTA                         540
121  R  K  D  L  A  S  A  I  L  D  L  P  V  L  E  H  L  F  A  Q
     CGCAAGGATTTGGCCAGTGCTATCCTTGACCTGCCAGTCCTGGAGCACCTCTTTGCCCAG                       600
141  H  R  S  D  L  V  S  G  R  L  P  R  G  L  S  L  K  E  Q  G
     CACCGGAGTGACCTGGTGAGTGGTCGGCTTCCCCGTGGCCTGAGTCTCAAGGAGCAGGGT                       660
161  E  C  L  S  L  A  V  L  D  L  A  R  M  A  R  E  Q  A  Q  R
     GAGTGTCTCAGCCTGGCCGTGTTGGACCTGGCCCGGATGGCCCGAGAGCAGGCCCAGCGG                       720
181  R  G  E  L  L  K  T  V  S  Y  K  A  C  L  P  P  S  L  R  D
     CGGGAGCTGCTCAAGACTGTCAGCTACAAGGCCTACCCCAAGCCTGGCGAC                                780
201  L  I  Q  G  L  S  F  V  T  G  R  R  I  R  R  T  V  E  S  P
     CTGATCCAGGGCCTGAGCTTCGTGACCGGGAGGCGTATTCGGAGGACGGTGGAGAGCCCC                       
221  L  R  R  V  A  A  C  Q  A  D  R  H  S  L  M  A  K  Y  I  M
     CTGCGCCGGGTGGCCGCCTGCCAGGCAGACCGGCACTCGCTCATGGCCAAGTACATCATG                       
241  D  L  E  R  L  D  P  A  G  A  A  E  T  F  H  V  G  L  P  G
     GACCTGGAGCGGCTCGATCCAGCCGGGGCCGCCGAGACCTTCCACGTGGGCCTGCCCGGG                       
261  A  L  G  G  H  D  G  L  G  L  V  R  V  A  G  D  G  G  I  A
     GCCCTTGGTGGCCACGACGGGCTGGGGCTCGTCCGGGTGGCTGGTGACGGCGGCATCGCC                       
```

FIG. 1A

```
281  W  T  Q  G  E  Q  E  V  L  Q  P  F  C  D  F  P  P  E  I  V  D
     TGGACCCAGGGAGAACAGGAGGTCCTCCAGCCCTTCTGTGACTTTCCAGAAATGTAGAC        900
301  I  S  I  K  Q  A  P  R  V  G  P  A  G  E  H  R  L  V  T  V
     ATTAGCATCAAGCAGGCCCCGCGTTGGCCCGGAGAGCACCGCCTGGTCACTGTT            960
321  T  R  T  D  N  Q  I  L  E  A  E  F  P  G  L  P  E  A  L  S
     ACCAGGACAGACAATCAGATTTTAGAGGCCGAGTTCCCAGGGCTGCCCGAGGCTCTGTCG     1020
341  F  V  A  L  V  D  G  Y  F  R  L  T  T  D  S  Q  H  F  F  C
     TTCGTGGCGCTCGTGGACGGCTACTTCCGGCTACTTCCGGACTACTGACACTTCTTCTGC     1080
361  K  E  V  D  P  R  L  L  E  E  V  A  E  Q  C  H  G  P  I  T
     AAGGAGGTGGACCCGAGGCTGCTGGAGGAAGTGGCCGAGCAGTGCCACGGCCCCATCACT     1140
381  L  D  F  A  I  N  K  L  K  T  G  G  S  R  P  G  S  Y  V  L
     CTGGACTTTGCCATCAACAAGCTCAAGACTGGGGGCTCACTGCCTGGCTCCTATGTTCTC    1200
401  R  R  I  P  Q  D  F  D  S  F  L  L  T  V  C  V  Q  N  P  L
     CGCCGCATCCCCCAGGACTTTGACAGCTTCCTCCTCACTGTCTGTGTCCAGAACCCCTT     1260
421  G  P  D  Y  K  G  C  L  I  R  R  S  P  T  G  T  F  L  L  V
     GGTCCTGATTATAAGGGCTGCCTCATCCGGCGCAGCCCCACAGGAACCTTCCTTCTGGTT    1320
441  G  L  S  R  P  H  S  S  L  R  E  L  L  A  T  C  W  D  G  G
     GGCCTCAGCCGACCCCACAGCAGTCTTCGAGAGCTCCTGGCAACCTGCTGGGATGGGGG     1380
461  L  H  V  D  G  V  A  V  T  L  T  S  C  C  I  P  R  P  K  E
     CTGCACGTAGATGGGGTGGCAGTGACCCTCACTTCCTGTTGTATCCCCAGACCCAAAGAA    1440
481  K  S  N  L  I  V  V  Q  R  G  H  S  P  P  T  S  S  L  V  Q
     AAGTCCAACCTGATTGTGGTCCAGAGAGGTCACAGCCCACCACATCCTTGGTTCAG       1500
501  P  Q  S  Q  Y  Q  L  S  Q  M  T  F  H  K  I  P  A  D  S  L
     CCCCAATCCCAATACCAGTTCAGATGACATTTCACAAGATCCCTGCTGACAGCCTG        1560
521  E  W  H  E  N  L  G  H  G  S  F  T  K  I  Y  R  G  C  R  H
     GAGTGGCATGAGAACCTGGGCCATGGCTCCTTCACCAAGATTTACCGGGGCTGTCCCAT    1620
541  E  V  V  D  G  E  A  R  K  T  E  V  L  K  V  M  D  A  K
     GAGGTGGTGGATGGGGAGGCCCGAAAGACAGAGGTGCTGAAAGTCATGGATGCCAAG      1680
561  H  K  N  C  M  E  S  F  L  E  A  S  L  M  S  Q  V  S  Y
     CACAAGAACTGCATGGAGTCATTCCTGGAAGCCAGCCTTGATGAGCCAAGTGTCGTAC     1740
```

```
581  R  H  L  V  L  L  H  G  V  C  M  A  G  D  S  T  M  V  E  E
     CGGCATCTCGTGCTCCACGGGGTGTGCATGGCTGGAGACAGCACCATGGTCGAGGAA        1800
601  F  V  H  L  G  A  I  D  M  Y  L  R  K  R  G  H  L  V  P  A
     TTTGTACACTTGGGGGCCATAGACATGTATCTCCGAAAGCGTGGCCACCTGGTGCCAGCC     1860
621  S  W  K  L  Q  V  V  K  Q  L  A  Y  A  L  N  Y  L  E  D  K
     AGCTGGAAGCTGCAGGTCGTCAAACAGCTGGCCTACGCCCTCAACTATCTGGAGGACAAA     1920
641  G  L  S  H  G  N  V  S  A  R  K  V  L  L  A  R  E  G  A  D
     GGCCTGTCCCATGGCAATGTCTCCGCCCGGAAGGTCCTCCTGGCTCGGGAGGGGCTGAT      1980
661  G  S  P  P  F  I  K  L  S  D  P  G  V  S  P  A  V  L  S  L
     GGGAGCCCCGCCCTTCATCAAGCTGAGTGACCCCGGTGTCAGCCCTGTTAAGCCTG         2040
681  E  M  L  T  D  R  I  P  W  V  A  P  E  C  L  R  E  A  Q  T
     GAGATGCTCACCGACAGGATCCCCTGGGTGGCCCCCGAGTGTCTCCGGGAGGCCAGACA      2100
701  L  S  L  E  A  D  K  W  G  F  G  A  T  V  W  E  V  F  S  G
     CTTAGCTTGGAAGCTGACAAGTGGGGCTTCGGGGCAACGGTCTGGGAAGTGTTTAGTGGC     2160
721  V  T  M  P  I  S  A  L  D  P  A  K  K  L  Q  F  Y  E  D  R
     GTCACCATGCCCATCAGTGCCCTAGACCCTGCCAAGAAACTTCAATTTTATGAGGACCGG    2220
741  Q  Q  L  S  A  P  K  W  T  E  L  A  L  L  I  Q  Q  C  M  A
     CAGCAGCTGTCGGCCCCAAAGTGGACAGAGCTGGCCCTCCTCATTCAACAGTGCATGGCC    2280
761  Y  E  P  V  Q  R  P  S  L  R  A  V  I  R  D  L  N  S  L  I
     TATGAGCCGGTCCAGAGGCCCTCCTTACGAGCCGTCATTCGTGACCTCAATAGTCTCATC    2340
781  S  S  D  Y  E  L  L  S  D  H  T  W  C  P  G  T  R  D  G  L
     TCTTCAGACTATGAGCTCCTCAGTGACCACACCTGGTGCCCACTCGTGATGGCTG         2400
801  W  N  G  A  Q  L  Y  A  C  Q  D  P  T  I  F  E  E  R  H  L
     TGGAATGGTGCCCAGCTCTATGCCTGCCAAGACCCCACGATCTTCGAGGAGAGACACCTC    2460
821  K  Y  I  S  Q  L [G  K  G  F  G] S  V  E  L  C  R  Y  D
     AAGTACATCTCACAGCTGGGCAAGGGCTTCTTGGCCGTCGAGCTGTGCCGCTATGAC       2520
841  P  L  G  D  N  T  G  A  L  V  A  V  K  Q  L  Q  H  S  G  P
     CCGCTAGGGGACAATACAGGGGCACTGGTGGCCGTGAAACAGTTGCAACAGAGTGGGCCA    2580
```

```
 861  D  Q  Q  R  D  F  Q  R  E  I  Q  I  L  K  A  Q  H  S  D  F
      GACCAGCAGAGGGACTTTCAGCGGGAGATTCAGATTCTCAAGGCACAGCACAGTGATTTC   2640
 881  I  V  K  Y  R  G  V  S  Y  G  P  G  R  Q  S  P  A  L  V  M
      ATTGTCAAGTATCGTGGTGTCAGCTATGGCCCCGGCCGCCAGAGCCCTGGCTCTGGTCATG   2700
 901  E  Y  L  P  S  G  C  L  R  D  F  L  Q  R  H  R  G  L  D  A
      GAGTACCTGCCCAGCGGCTGCCTGCGAGACTTCCTGCAGCGCCACCGGGGCCTGGATGCC   2760
 921  S  R  L  L  Y  S  Q  I  C  K  G  M  E  Y  L  G  S  R
      AGCCGCCTCCTCTATTCCCAGATCTGCAAGGGCATGGAGTACCTGGGCTCCCGC         2820
 941  R  C  V  H  R  D  L  A  A  R  N  I  L  V  E  S  E  A  H  V
      CGCTGCGTGCACCGCGACCTGGCCGCCCGCAACATCCTGGTGGAGAGCGAGGCACACGTC   2880
 961  K  I  A  D  F  G  L  A  K  L  L  P  L  D  K  D  Y  Y  V  V
      AAGATCGCTGACTTCGGCCTAGCTAAGCTGCTCCCTTTGGACAAAGACTACTACGTGGTC   2940
 981  R  E  P  G  Q  S  P  I  F  W  Y  A  P  E  S  L  S  D  N  I
      CGCGAGCCAGGCCAGAGCCCCATTTTCTGGTATGCCCCAGAATCCCTCAGTGACAACATC   3000
1001  F  S  R  Q  S  D  V  W  S  F  G  V  V  L  Y  E  L  F  T  Y
      TTCTCTCGCCAGTCAGACGTCTGGAGCTTCGGGGTGGTCCTGTACGAGCTCTTCACCTAC   3060
1021  C  D  K  S  C  S  P  S  A  E  F  L  R  M  H  G  C  E  R  D
      TGCGACAAAAGCTGCAGCCCCTCGGCCGAGTTCCTGCGGATGCATGGATGTGAGCGGGAT   3120
1041  V  P  R  L  C  R  L  L  E  L  L  E  E  G  Q  R  L  P  A  P
      GTCCCCCGCCTCTGCCGTCTCCTGGAACTGCTGGAAGAGGGCCAGAGGCTCCCGGCCCCT   3180
1061  P  C  C  P  A  E  V  S  C  Y  S  G  W  R  D  D  I  C  L  P
      CCTTGCTGCCCTGCCGAGGTGAGTTGCTACAGTGGCTGGAGAGACGACATCTGCCTGCCT   3240
1081  A  E
      GCTGAGTGAGTTGCTACAGTGCTACAGAGACCACATCTCCATGCCTCCTGTGCCGACA     3300
      GTAATCTCACGGCAGCTGCCGCAACCCTGCCAGACCTTCTACCATCACCCGCCACC       3360
      ACCGTGCAGCTGCCACAACCCTGTCCTGCACGCTACTACCCGCTGTACCCAACAAG       3420
      ACCTGCTGACCCTGTCCTTGGTGTCACGTCACCTCAGAGTGCTGAGG                3480
      CCCAGCAGGGGTCTGGTTGGTCTGGTGTCACACACAGGCCACACAGACCATCGCATCT     3540
      ACAGGCCTTTGATTACCTCCTGGATGGTGCTCCTACTATCTACCCCAGACCAAGGCCACC  3600
      TGCAGCCTGTGGAGTCAACTGCAGAATGCAGAATAAATCACCCTA
```

FIG. 1D

```
     1
JAK3   MAPPSEETPLIPQRSCLLLSTEAGA..LHVLLPARGPGPPQR............LSFSFGDHLAEDLCVQAAKASAILPVYHSLFALATEDLSCWFPRAT   100
JAK2   HGMACLTMTEMEATSTSPVHQNGDIPGSANSVKQIEPVLQVLYHSLGQAEGEYLKFPSGEYVAEEICVAASKACGITPVYHNMFALMSETERIWYPPNH
JAK1   MQYLNIKEDCNAMAFCAKMRSSKKTEVNLEAPEPGVEVIF.YL.......SDREPLRLGSGEYTAEELCIRAAQACRISPLCHNLFALYDENTKLMYAPNR
TYK2   HPLRHWGMARGSKPVGDGAQPHAAMGGLKVLLHWAGPGGGEFW..........VTFSESSLTAEEVCIHIAHKVGITPPCFNLFALFDAQAVWLPPNH
CONS   M--------------------------------------------------L----G----AEE-C---A--A-I-P---HNLFAL--------W-PPN-

101
JAK3   SSPWRMPAPQVLLYRIRFYFPNWFGLEKCHRFGLRKDL................ASAILDLPVLEHLFAQHRSDLVSGRLPRGLSLKEQG.........ECLSLA   200
JAK2   VFHIDESTRHDILYRIRFYFPHWYCSGSSRTYRYGVSRGAEA............PLLDDFVMSYLFVQWRHDFVHGNIKVPVTHETQE........ECLGMA
JAK1   TITVDDKMSLRLHYRMRFYFTNWHGTNDNEQSVWRHISPKKQKNGYEKKKIPDATPLLDASSLEYLFAQGQYDLVKCLAPIRDPKTEQDGHDIENECLGMA
TYK2   ILEIPRDASLMLYFRIRFYFRNWHGMNPREPAVYRCGPPGTEASSD..QTAQGMQLLDPASFEYLFEQKHEFVNDVASLWELSTEEIHHFKNESLGMA
CON    -------L-YRIRFYF-NW-G----------------------------LLD-----EYLF-Q----D-V-------EQ--------ECLGMA

201
JAK3   VLDLARMAREQAQRGELLKTVSYKACLPPSLRDLIQGLSFVTGRRIRRTVESPLRRV....AACQADRHSLMAKYIMDLERLDPAGAAETFHVGLFG.   300
JAK2   VLDMMRIAKEKDQTPLAVYNSVSYKTFLPKCVRAKIQDYHILTRKRIRYRFRRFIQQF...SQCKATARNLKLKYLINLETLQSAFYTEQFEVKESAR
JAK1   VLAISHYAMHKKMQLPELPKDISYKRYIPETLNKSIRQRNLLTRMRINNVFKDFLKEFNNKTICDSSVSTHDLKVKYLATLETLTKHYGAEIFETSMLLI
TYK2   FLHLCHLALRHGIPLEEVAKKTSFKDCIPRSFRRHIRQHSALTRLRLRNVFRRFLRDFQ.....PGRLSQQMVVKYLATLERLAPRFGTERVPVCHLRL
CONS   VL-----A-------E--K--SYK-----P----R--I--------LTR-RIR--F--FL--F-------LK-KYL--LE-L-------E-F-V----

301
JAK3   ..............ALGGHDGLGLVRVAGDGGIAWTQGE.............................................QEVLQPFCDFPE   400
JAK2   GPSGEEIFATIIIT............................CNGGIQWSRGKH..........................KESETLTEQDVQLYCDFPD
JAK1   SSENEMNWFHSND............GGNVLYYEVMVTGNLGIQWRHKPNVVSVEKE........KNKLKRKKLENKDKKDEEKNKIREE.WNNFSFFPE
TYK2   LAQAEGEPCYIRDSGVAPTDPGPESAAGPPTHEVLVTGTGGIQWMPVEEEVNKEEGSSGSGRNPQASLFGKKAKAHKAFGQPADRPREPLWAYFCDFRD
CONS   --------------------------V-VTG-GGIQW-----------------------------------------------E------FCDFP-

401
JAK3   IVDISIKQAPRVGPAGEHRLVTVTRTDNQILEAEFPGLPEALSFVALVDGYFRLTTDSQHFFCKEVD.PRLLEEVAEQCHGPITLDFAINKLKTGGSRPG   500
JAK2   IIDVSIKQANQ.ECSNESRIVTVHKQDGKVLEIELSSLKEALSFVSLIDGYYRLTADNIIYLCKEVAPPAVLENIHSNCHGPISMDFAISKLKKAGNQTG
JAK1   ITHIVIKE...........SVVSINKQDNKKMELKLSSIEEALSFVSLVDGYFRLTADANHYLCTDVAPPLIVHNIQNGCHGPICTEYAINKLRQEGSEEG
TYK2   ITHIVVLKE...........HCVSIHRQDNKCLELSLPSRAAALSFVSLVDGYFRLTADSSHYLCHEVAPPRLVMSIRDGIHGPLLEPFVQAKLR...PEDG
CONS   I-----IK---------V----QDNK-LE--L-S----EALSFVSLVDGYFRLTAD--HYLC-EVAPP-------I----CHGPI---FAI-KL-----G
```

FIG. 2A

```
       501
JAK3   SYVLRRIPQDFDSFLLTVC......VQNPLGPDYKGCLIRRSPTGTFLIVGLSRPHSSLRELLATCWDGGLHVPGVAVTLTSCCIPRPKEKSNLIVVQR
JAK2   LYVLRCSPKDFNKYFLTFA......VERENVIEYKHCLITKNENGEYNLSGTNRNFSNLKDLLNCYQMETVRSDSIIFQFTKCCPPKPKDKSNLLVFRT
JAK1   MYVLRWSCTDFDNILMTTCFKSEQVQGAQK.QFKNFQI.EVQKGRYSLHGSDRSFPSLGDLMSHLKKQILRTDNISFMLKRCCQPKPREISNLLVATK
TYK2   LYLIHWSTSHPYRLILTVA..QRSQAPDGMQSLRLRKFPI.EQQDGAFVLEGWGRSFPSVRELGAALQGCLLRAGDDCFSLRRCCLPQPGETSNLII.MR
CONS   -YVLRWS---DF----LTV-------V------I---G------L--G---R-F-SL--L--------R-D---F-L---CC-P-P----SNLLV----
       601
JAK3   GHSPPTTSSLVQPQSQYQLSQMTFHKIPADSLEWHENLGHGSFTKIYRGCRHEVD.GEARKTE.............................VLLKVMDAKHKNCMESFL
JAK2   NGISDVQISPTLQRHNNVNQMVFHKIRNEDLIFNESLGQGTFTKIFKGVRREVGDYGQLHKTE..............................VLLKVLDKAHRNYSESFF
JAK1   K......AQEWQPVYPMSQLSFDRILKKDLVQGEHLGRGTRTHIYSGTLMDYKDDEGTSEEK...........................IKVILKVLDPSHRDISLAFF
TYK2   G......ARASPRTLNLSQLSFHRVDQKEITQLSHLGQGTRTNVYEGRLR..VEGSGDPEEGKMDDEDPLVPGRDRGQELRVVLKVLDPSHHDIALAFY
CONS   -------Q-----FH-I----L---E-LG-GT-T-IY-G-------D-------------------V-LKVLD---H-------F--
       701                                                              JH2
                                                                         ↑
JAK3   EAASLMSQVSYRHLVLLHGVCMAG..DSTMVEEFVHLGAIDMYLRKRGHLVPASWKLQVVKQLAYALNYLEDKGLSHGNVSARKVLLAREGA..DGSPPFI
JAK2   EAASMSQLSKHLVLNYGVCVCGEENILVQEFVKFGSLDTYLKKNKNSINILWKLGVAKQLAWAMHFLEEKSLIHGNVCAKNILLIREEDRRTGNPPFI
JAK1   EAASMRQVSHKHIVYLYGVCVRDVENIMVEEFVEGGPLDLFMHRKSDVLTTPWKFKVAKQLASALSYLEDKDLVHGNVCTKNLLLAREGI.DSECGPFI
TYK2   ETASLMSQVSHTHLAFVHGVCVRGPENSMVTEYVEHGPLDVWLRERGHVPMAWKMVVAQQLASALSYLENKNLVHGNVCGRNILLARLGL.AEGTSPFI
CONS   EAAS--HSQVSH-HLV----GVCV-G--EN-HV-EFV---G--LD---R-------WK--VAKQLA-AL-YLEDL-L-HGNVC--NILLAREG------PFI
       801
JAK3   KLSDPGVSPAVLSLEMLTDRIPWVAPECLREAQT.LSLEADKWGFGATVWEVFSGVTMPISALDPAKKLQFYEDRQQLSAPKWTELALLIQCMAYEPVQ
JAK2   KLSDPGISITVLPKDILQERIPWVPPECIENPKN.LNLATDKWSFGTTLWEICSGGDKPLSALDSQRKLQFYEDKHQLPAPKWTELANLINNCMDYEPDF
JAK1   KLSDPGIPITVLSRQECIERIPWIAPECVEDSKN.LSVAADKWSFGTTLWEICYNGEIPLKDKTLIEKERFYESRCRPVTPSCKELADLMTRCMNYDPNQ
TYK2   KLSDPGVGLGALSREERVERIPWLAPECLPGGANSLSTAMDKWGFGATLLEICFDGEAPIQSRSPSEKEHFYQRQHRLPEPSCPQLATLTSQCLTYEPTQ
CONS   KLSDPG----VLS-----ERIPW-APEC-------G---PL------K--FYE-----L--P----ELA-L--CM-YEP-Q
```

FIG. 2B

```
       901
JAK3   RPSLRAVIRDLNSLISSDYELLSDRTWCPGTRDGLMNGAQLYACQ.DPTIFEERIILKYISQLGKGFFGSVELCRYDPLGDNTGALVAVKQLQ.HSGPDQQ
JAK2   RPAFRAVIRDLNSLFTPDYELLTENDMLPNMRIGALGFSGAFEDR.DPTQFEERIILKFLQQLGKGNFGSVEMCRYDPLQDNTGEVVAVKKLQ.HSTEEHL
JAK1   RPFFRAIMRDINKLEEQNPDIVSRKKNQPTEV........DPTIFEKRFLKRIRDLGEGHFGKVELCRYDP.EDNTGEQVAVKSLKPESGGNHI
TYK2   RPSFRTILRDLTRVQPHNLADVLTVNRDSPAV.........GPTTFHKRYLKKIRDLGEGHFGKVSLYCYDPTNDCTGEMVAVKALKADCGPQHR
CONS   RP--FRA--RDLN-L------------P------------DPT-FE-R-LKQI--LG-G-FG-VELCRYDP--DNTGE-VAVK-L---SG--H-
       1001                                                                                  1100
JAK3   RDFQREIQILKAQHSDFIVKYRGVSYGPGRQSPALVMEYLPSGCLRDFLQRHRG..LDASRLLLYSSQICKGMEYLGSRRCVHRDLAARNILVESEAHVKI
JAK2   RDFEREIEILKSLQHDNIVKYKGVCYSAGRRNLRLIMEYLPYGSLRDYLQKHKERIDHKKLLQYTSQICKGMEYLGTKRYIHRDLATRNILVENENRVKI
JAK1   ADLKKEIEILRNLYHENIVKYKGICTEDGGNGIKLIMEFLPSGSLKEYLPKNKNINLKQQLKYAVQICKGMDYLGSRQYVHRDLAARNVLVESEHQVKI
TYK2   SGWKQEIDILRTLYHEHIIKYKGCCEDQGEKSLQLVMEYVPLGSLRDYLP..RISIGLAQLLFAQQICEGMAYLHAHDYIHRDLAARNVLLDNDRLVKI
CONS   -D---EI--IL--L-H---IVKYKG-C----G-----L-HEYLP-GSLRDYL------I----L-HRDLAARN-LV-E---VKI
       1101                                                                                  1200
JAK3   ADFGLAKLLPLDKDYYVVREPGQSPIFWYAPESLSDNIFSRQSDVWSFGVVLYELFTYCDKSCSPSAEFLRMMGCERDVPRLC.RLLELLEEGQRLPAPP
JAK2   GDFGLTKVLPQDKEYYKVKEPGESPIFWYAPECLMQSKFYIASDVWSFGVTLYELFTYIEKSKSPPVEFMRHIGNDKQGQMIVFHLIELLKSNGRLPRPE
JAK1   GDFGLTKAIETDKEYYTVKDDRDSPVFWYAPECLMQSKFYIASDVWSFGVTLHELLTYCDSDSSPMALFLKMIGPT.HGQMTVTRLVNTLKEGKRLPCPP
TYK2   GDFGLAKAVPEGHEYYRVREDGDSPVFWYAPECLKEYKFYYASDVWSFGVTLYELLTNICDSSQSPPTKFLELIGIA.QQGMTVLRLTELLERGERLPRPD
CONS   GDFGL-K--P-DKEYY-V--E-G-SP-FWYAPE-L---LF--ASDVWSFGV-LYEL-TYCD-S-SP----FL-MIG----GQM-V-RL-ELL--G-RLP-P-
       1201                     1249
JAK3   CCPAEVSCYSGWRDDICLPAE..........
JAK2   GCPDEIYVIMTECWNNNVSQRPSFRDLSFGWIKCGTV.........
JAK1   NCPDEVYQLMRKCWEFQPSNRTSFQNLIEGFEALLK..........
TYK2   KCPCEVYHLMKNCWETEASFRPTFENLIPILKTVIEKYQGQAPSVFSVC
CONS   -CP-EVY-LM---CW----S-R--F---L-----------------
```

```
hJAK3    1  MAPPSEETPLIPQRSCSLLSTEAGALHVLLPARGPPPQRLSFSFGDHLAEDLCVQAAKA       60
rJAK3    1  MAPPSEETPLISQRSCSLSSSEAGALHVLLPPRGPPPQRLSFSFGDYLAEDLCVRAAKA       60
CONS        MAPPSEETPLI QRSCSL S+EAGALHVLLP RGPGPPPQRLSFSFGD+LAEDLCV+AAKA hJAK3   61  SAILPVYHSLFALATEDLSCWFPRATSSPWRMPAPQVLLYRIRFYFPNWFGLEKCHRFGL    120
rJAK3   61  CGILPVYHSLFALATEDLSCWFPPSHIFSIEDVDTQVLVYRLRFYFPGWFGLETCHRFGL    120
CONS            ILPVYHSLFALATEDLSCWFP +        QVL+YR+RFYFP WFGLE CHRFGL hJAK3  121  RKDLASAILDLPVLEHLFAQHRSDLVSGRLPRGLSLKEQGECLSLAVLDLARMAREQAQR    180
rJAK3  121  HKDLTSAILDVHVLEHLFAQHRSDLVSGRLPVGLSLKDQGEFLSLAVLDLAQMARKQAQR    180
CONS         KDL SAILD+ VLEHLFAQHRSDLVSGRLP GLSLK+QGE LSLAVLDLA+MAR+QAQR hJAK3  181  RGELLKTVSYKACLPPSLRDLIQGLSFVTGRRIRRTVESPLRRVAACQADRHSLMAKYIM    240
rJAK3  181  PGELLKSVSYKACLPPSLRDLIQGSFVTRRRIRRTVVQALAPCSSLPSRPYALMAKYIL    240
CONS         GELLK+VSYKACLPPSLRDLIQG SFVT RRIRRTV  L    +  +  ++LMAKYI+ hJAK3  241  DLERLDPAGAAETFHVGLPGALGGHDGLGLVRVAGDGGIAWTQGEQEVLQPFCDFPEIVD    300
rJAK3  241  DLERLHPAATTESFLVGLPGAQEEP...GCLRVTGDNGIAWSSKDQELFQTFCDFPEIVD    297
CONS        DLERL PA    E+F VGLPGA       G   RV GD GIAW+   +QE+  Q FCDFPEIVD hJAK3  301  ISIKQAPRVGPAGEHRLVTVTRTDNQILEAEFPGLPEALSFVALVDGYFRLTTDSQHFFC    360
rJAK3  298  VSIKQAPRVGPAGEHRLVTITRMDGHILEAEFPGLPEALSFVALVDGYFRLICDSRHFFC    357
CONS        +SIKQAPRVGPAGEHRLVT+TR D   ILEAEFPGLPEALSFVALVDGYFRL  DS+HFFC hJAK3  361  KEVDP.RLLEEVAEQCHGPITLDFAINKLKTGGSRPGSYVLRRIPQDFDSFLLTVCVQNP    419
rJAK3  358  KEVAPPRLLEEEAELCHGPITLDFAIHKLKAAGSLPGSYILRRSPQDYDSFLLTACVQTP    417
CONS        KEV P RLLEE AE CHGPITLDFAI+KLK  GS PGSY+LRR PQD+DSFLLT CVQ P hJAK3  420  LGPDYKGCLIRRSPTGTFLLVGLSRPHSSLRELLATCWDGGLHVDGVAVTLTSCCIPRPK    479
rJAK3  418  LGPDYKGCLIRQDPSGAFSLVGLSQLHRSLSQLELLTACWHSGLQVDGTALNLTSCCVPRPK    477
CONS        LGPDYKGCLIR+ P+G F LVGLS+ H SL+ELL  CW    GL  VDG A+ LTSCC+PRPK hJAK3  480  EKSNLIVVQRGHSPPTSSLVQPQSQYQLSQMTFHKIPADSLEWHENLGHGSFTKIYRGCR    539
rJAK3  478  EKSNLIVVRRGRN PTPAPGHSPSCCALTKLSFHTIPADSLEWHENLGHGSFTKIFHGHR    537
CONS        EKSNLIVV+RG + PT +      S       L++++FH IPADSLEWHENLGHGSFTKI+ G R
```

```
hJAK3  540  HEVVDGEARKTEVLLKVMDAKHKNCMESFLEAASLMSQVSYRHLVLLHGVCMAGDSTMVE  599
rJAK3  538  REVVDGETHDTEVLLKVMDSRHQNCMESFLEAASLMSQVSYPHLVLLHGVCMAGDSIMVQ  597
CONS        EVVDGE   TEVLLKVMD  H NCMESFLEAASLMSQVSY HLVLLHGVCMAGDS MV+ hJAK3  600  EFVHLGAIDMYLRKRGHLVPASWKLQVVKQLAYALNYLEDKGLSHGNVSARKVLLAREGA  659
rJAK3  598  EFVYLGAIDTYLRKRGHLVPASWKLQVTKQLAYALNYLEDKGLPHGNVSARKVLLAREGV  657
CONS        EFV+LGAID YLRKRGHLVPASWKLQV KQLAYALNYLEDKGL HGNVSARKVLLAREG hJAK3  660  DGSPPFIKLSDPGVSPAVLSLEMLTDRIPWVAPECLREAQTLSLEADKWGFGATWEVFS   719
rJAK3  658  DGNPPFIKLSDPGVSPTVLSLEMLTDRIPWVAPECLQEAGTLNLEADKWGFGATTWEVFS  717
CONS        DG+PPFIKLSDPGVSP VLSLEMLTDRIPWVAPECL+EA TL+LEADKWGFGAT WEVFS hJAK3  720  GVTMPISALDPAKKLQFYEDRQQLSAPKWTELALLIQQCMAYEPVQRFSLRAVIRDLNSL  779
rJAK3  718  GAPMHITSLEPAKKLKFYEDRGQLPALKWTELEGLIAQCMAYDPGRRPSFRAILRDLNGL  777
CONS        G  M I++L+PAKKL+FYEDR QL A KWTEL  LI QCMAY+P  +RPS RA++RDLN L hJAK3  774  ISSDYELLSDHTW.CPGTRDGLWNGAQLYACQDPTIFEERHLKYISQLGKGFFGSVELCR  838
rJAK3  778  ITSDYELLSDPTPGIPNPRDELCGGAQLYACQDPAIFEERHLKYISLLGKGNFGSVELCR  837
CONS        I+SDYELLSD T  P  RD L  GAQLYACQDP IFEERHLKYIS LGKG FGSVELCR hJAK3  794  YDPLGDNTGALVAVKQLQHSGPDQQRDFQREIQILKAQHSDFIVKYRGVSYGPGRQSPAL  898
rJAK3  838  YDPLGDNTGPLVAVKQLQHSGPEQQRDFQREIQILKALHCDFIVKYRGVSYGPGRQELRL  897
CONS        YDPLGDNTG LVAVKQLQHSGP+ QQRDFQREIQILKA H DFIVKYRGVSYGPGRQ   L hJAK3  899  VMEYLPSGCLRDFLQRHRG.LDASRLLLYSSQICKGMEYLGSRRCVHRDLAARNILVESE  957
rJAK3  898  VMEYLPSGCLRDFLQRHRARLHNDRLLLFAWQICKGMEYLGARRCVHRDLAARNILVESE  957
CONS        VMEYLPSGCLRDFLQRHRA L   RLLL++ QICKGMEYLG+RRCVHRDLAARNILVESE hJAK3  958  AHVKIADFGLAKLLPLDKDYYVVREPGQSPIFWYAPESLSDNIFSRQSDVWSFGVVLYEL  1017
rJAK3  958  AHVKIADFGLAKLLPLGKDYYVVRPGQSPIFWYAPESLSDNIFSRQSDVWSFGVVLYEL  1017
CONS        AHVKIADFGLAKLLPL KDYYVVR PGQSPIFWYAPESLSDNIFSRQSDVWSFGVVLYEL hJAK3  1018 FTYCDKSCSPSAEFLRMMGCERDVPRLCRLLELLEEGQRLPAPPCCPAEVSCYSGWRDDI 1077
rJAK3  1018 FTYSDKSCSPSTEFLRMIGPEREGSPLCHLLELLAEGRRLPPPSTCPTEVQELMQLCWSP 1077
CONS        FTY DKSCSPS EFLRM+ G ER+     LC LLELL EG+RLP +RLP P  CP EV hJAK3  1078 CLPAE                                                        1082
rJAK3  1078 NPQDRPAFDTLSPQLDALWRGSPG                                     1101
CONS

FIG. 3B
```

NUCLEIC ACID ENCODING NOVEL PROTEIN TYROSINE KINASE

The present invention was made with government support under grant no. CA 06973 from the National Institutes of Health. The government has certain rights in the invention.

BACKGROUND OF THE INVENTION

1. Field of the Invention

The present invention relates generally to a protein tyrosine kinases and specifically to JAK3, a novel protein tyrosine kinase of the JAK family.

2. Description of Related Art

Proliferation and differentiation of hematopoietic cells is dependent upon the binding of hematopoietic growth factors and cytokines to their respective cell surface receptors (Cross, et al., Cell, 64:271, 1991; Ogawa, M., Blood, 81:2844, 1993; Heimfeld, S., et al., Proc. Natl. Acad Sci. USA, 88:9902, 1991). Some of these receptors transduce the signal at the cell surface to the cytoplasm through the activation of a tyrosine kinase domain in the cytoplasmic portion of the receptor (eg., CSF1, c-kit, STK-1/FLT3/FLK2-) (Boyle, W. J., Current Opinion in Oncology, 4:156, 1992, Chiba, T., et al., Nature, 362:646, 1993, Schlessinger, J., et al., Neuron, 9:383, 1992, Ullrich, A. and Schlessinger, J., Cell, 61:203, 1990). Another group of hematopoietic receptors lack intrinsic kinase catalytic domains (e.g., IL-3, GM-CSF, G-CSF, and EPO receptors) (Miyajima, A., et at., Blood, 82:1960, 1993, Fukunaga, R., et al., EMBO, 10:2855, 1991, Wojchowski, D. M., et al., Stem Cells, 11:381, 1993), however, upon binding of their ligands, these receptors activate protein tyrosine phosphorylation of second messengers and the subsequent signal pathways to the cell's nucleus (Kishimoto, T. et al., Science, 258:593, 1992, Stahl, N., et at., Cell, 74:587, 1993).

Tyrosine kinases often play pivotal rules in the proliferation and differentiation of many cell types. Many growth factor receptors contain a tyrosine kinase domain as part of their cytoplasmic tail such that binding by ligand directly activates their tyrosine kinase activity. However, many other receptors do not contain a tyrosine kinase domain in their cytoplasmic tail. Addition of ligand to many cell types expressing these receptors still results in increased levels of phosphotyrosine. The JAK family, a series of related intracellular tyrosine kinases, has recently been shown to link these receptors and other members of the signal transduction pathway.

The JAK family members contain the highly conserved catalytic domain found in other tyrosine kinases (Firmbach-Kraft, I., et al., Oncogene, 5:1329, 1990, Hanks, S. K., et al., Methods in Enzymology, 200:38, 1991, Hunter, T., Methods in Enzymology, 200:3, 1991, Wilks, A. F., Proc. Natl. Acad. Sci. USA, 86:1603, 1989). One feature that distinguishes the JAK family from other tyrosine kinases is that each member also contains a second kinase-like domain of unknown function (Harpur, A. G., et al, Oncogene, 7:1347, 1992). In addition, the JAK family members do not contain SH2 or SH3 domains, signal peptide sequences, or transmembrane domains, and are localized in the cytoplasm (Wilks, A. F., et al, Molecular and Cellular Biology, 11:2057, 1991).

Three members of the JAK family, JAK1, JAK2, an TYK-2, have been functionally described. The first two members were isolated by a PCR approach utilizing degenerate oligonucleotide primers and TYK-2 was isolated by screening with a tyrosine kinase probe at reduced stringency (Silvennoinen, O. et al., Proc. Natl. Acad. Sci. USA, 90:8429, 1993). To date, the JAK family members have been shown to be involved with the receptors for numerous cytokines and growth factors, including IFNαβ and γ, IL-3, GM-CSF, EPO, GH, CNTF, LIF, OSM, IL-6, and PRL (Argetsinger, L. S., et al., Cell, 74:237, 1993, Lüttichen, C., et al., Science, 263:89, 1994, Müller, M., et al., Nature, 366:129, 1993, Stahl, N., et al., Science, 263:92, 1994, Velazquez, L., et al., Cell, 70:313, 1992, Watling, D., et al., Nature, 366:166, 1993, Witthuhn, B. A., et al., Cell, 74:227, 1993, Rui, H., et al., The Journal of Biological Chemistry, 269:5364, 1994). In most cases, the JAK family members seem to associate with the proximal membrane portion of the cytoplasmic domain of the receptor (e.g., gp130, LIFRβ, EPO) as a constitutive complex (Narazaki, M., et al., Proc. Natl. Acad. Sci. USA, 91:2285, 1994). In other cases, the association is not evident until ligand binding takes place (e.g., GH receptor). In either case, ligand binding results in increased JAK kinase activity.

The first evidence for the functional role of JAK family members was provided when it was shown that TYK-2 could rescue IFNα/β responsiveness in a cell line that had become unresponsive. In a similar fashion, JAK1 and JAK2 have been shown to function in the signalling of interferon pathways, as well. In each case, two different JAKS have been found to act with each type of IFN receptor; JAK2 and TYK-2 are involved exclusively with IFNγ and IFNα/β, respectively, whereas JAK1 is involved with both receptors. Stimulation of the IFNα/β receptors by the binding of their respective ligands results in the phosphorylation of p91 (STAT1) and p113 (STAT2), which are subunits of the ISGF3 transcription complex that binds the interferon-stimulated response element (ISRE). In the case of IFNγ, p91 alone is phosphorylated, which then binds gamma-activated sequences (GAS) of IFNγ activated genes (Shual, K., et at., Nature, 366:580, 1993, Ihle, J. N., et al., Trends in Biological Science, 19:222, 1994). Because each of these receptors associate with JAK1 it has been suggested that JAK1 may directly phosphorylate p91 (Loh, J. E., et al., Molecular and Cellular Biology, 14:2170, 1994). It has been recently reported that IL-6 (via gp130), which associates with JAK1 and TYK-2, also triggers the activation of p91 (STAT1) (Yuan, J., et al., Molecular and Cellular Biology, 14:1657, 1994). The EPO, and IL-3 receptors are also believed to similarly activate STAT family members. As all of the hematopoietic receptors seem to utilize certain common proteins in their signal transduction pathways, some of the specificity of the pathways may reside in the cell specific expression of STAT family members and their activation by JAK family members (Metcalf, D., Blood, 82:3515, 1993, Darnell, J. E., et at., Science, 264:1415, 1994).

Additional pairs of JAK family members have been found to associate with other receptors (e.g., CNTF, LIF, IL-6) and both become tyrosine phosphorylated upon the stimulation of these receptors (Silvennoinen, O., et al., Nature, 366:583, 1993). It is possible that reciprocal tyrosine phosphorylation between two JAKs is required as phosphorylation of both associating JAKs is necessary for signal transduction to occur. Thus, JAK family members may act in pairs, possibly as heterodimers.

Recently a Drosophila JAK family member, hop, was shown to be required maternally for normal embryonic development (Binari, et al., Genes & Dev., 8:300, 1994). Mutants in hop showed defects in the expression of several paired-role and segment polarity genes, implicating it in the control of transcription of these genes, a role that could be analogous to the defect in TYK-2, JAK1, or JAK2 in several cell lines that lost IFN responsiveness.

The present invention provides a new member of the JAK protein tyrosine kinase family. The structural homology between the JAK3 of this invention and the other members of JAK family, indicates that JAK3 is a new member of this family of non-receptor tyrosine kinases. In analogy to the other JAK family members, JAK3 is likely involved in the signal transduction pathway of already characterized receptors which lack intrinsic activity. Because of its strong expression in the fraction enriched for CD34+ normal human bone marrow, JAK3 is likely to be important in stem/progenitor cell growth, and/or survival, and/or differentiation, by transducing the signals of receptors which modulate these processes. In addition, JAK3 may also be involved in the signal transduction pathways of any of several already known or as yet unidentified non-tyrosine kinase receptors with which the other JAK members have not been shown to associate (e.g. IL-2, IL-4, IL-11).

SUMMARY OF THE INVENTION

The present invention provides a novel protein tyrosine kinase JAK3, a polynucleotide sequence which encodes JAK3 and antibodies which are immunoreactive with the protein. The amino acid sequence of JAK3 indicates that it is a new member of the JAK family of non-receptor tyrosine kinases. JAK3 is highly expressed in the CD34+/lin– fraction in normal human bone marrow which is highly enriched in hematopoietic stem/progenitor cells. Therefore, by analogy to other JAK family members, it is likely that JAK3 plays a role in the growth factor modulated differentiation/proliferation/survival of the stem/progenitor cells.

JAK3 is expressed in mammalian tissues, and particularly human tissue. For example, JAK3 is expressed in human hematopoietic tissues, (e.g., bone marrow), and non-hematopoietic human tissues, such as liver, lung, kidney, spleen and intestine. In particular, JAK-3 is most highly expressed in the stem/progenitor cell enriched fraction of normal human bone marrow. JAK-3 is further expressed in a wide range of leukemic derived cell lines including AMLs (KG1, TF-1, HEL), B lineage ALLs (PB697, Nalm-16, and Nalm-6), and T-ALLs (Molt-16, and Molt-3).

JAK3 is localized to chromosome 19, band p12-13.1, where another member of the JAK family, TYK-2 is co-localized. Several other genes containing tyrosine kinase domains are tandemly linked and may have evolved by cis duplications. Examples include the genes for the receptors of c-fms (CSF-1 receptor) and PDGFR β on chromosome 5 bands q31-q33, c-kit and PDGFR α on chromosome 4 bands q11-q13, as well as FLT1 and STK-1/FLT3/FLK2 on chromosome 13 band q12.

In another embodiment, the invention provides a method for ameliorating a cell proliferative disorder associated with JAK-3. In another embodiment, the invention provides a method for stimulating stem/progenitor cell proliferation/survival and differentiation in vitro.

BRIEF DESCRIPTION OF THE DRAWINGS

FIG. 1 shows nucleotide (cDNA) and predicted amino acid sequence of JAK3, (SEQ ID NO:1 and NO:2, respectively. The predicted amino acids are numbered on the left of each column with the nucleotides of the largest open reading frame numbered on the right, starting with the initiating methionine of JAK3. The conserved tyrosine kinase motifs GXGXXG and DFG are shown boxed. The highly conserved peptide regions chosen for the design of the degenerate oligo nucleotides used for the initial PCR [VHRDLA & DVWSFG] are shown in ovals. Also shown are 167 bases of the 5' untranslated region and 394 bases of the 3' untranslated region. Potential polyadenylation signals are underlined.

FIG. 2 (SEQ ID NO:5-9) shows an amino acid comparison between JAK3 and other JAK family members. The numbering system begins with the initiating methionine of the JAK family members. The numbering system does not take into account the insertion of gaps and, therefore, should be only regarded as a relative measure of location. The consensus sequence (CONS) is derived if three out of four JAK family members have the identical amino acid in that position. The conserved kinase domain of all tyrosine kinases, JAK homology domain 1 (JH1), and the putative second kinase domain, JAK homology domain 2 (JH2) are designated with arrows. With the exception of JAK2, (murine), all sequences are human.

FIG. 3 (SEQ ID NO:10-12) shows an amino acid comparison between human JAK3 and rat JAK3. The amino acid residues of each member are numbered beginning with the initiating methionine. The consensus sequence (CONS) of the two JAK family members are listed below the compared sequences when identical. Pluses (+) denote conservative amino acid substitutions.

DETAILED DESCRIPTION OF THE INVENTION

Figure 4A:
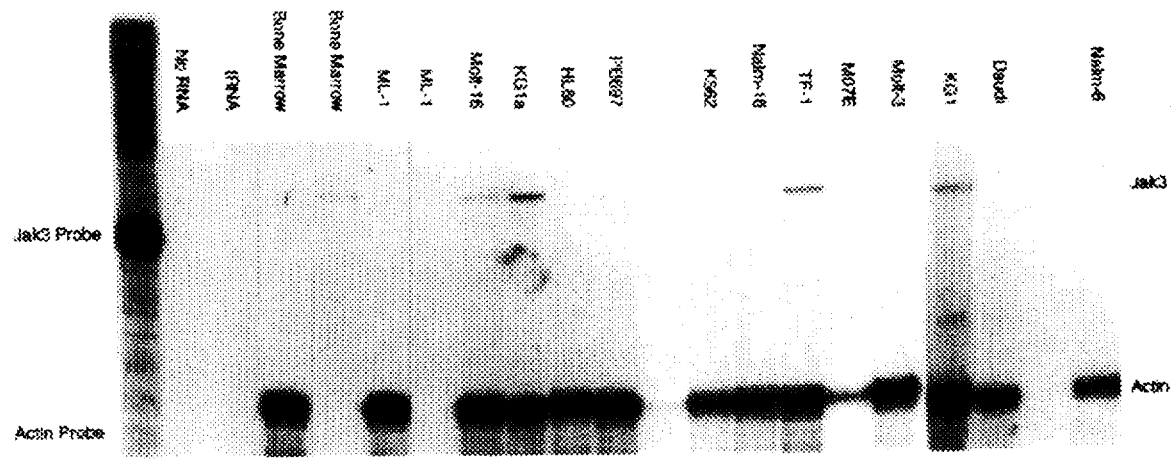
FIG. 4a shows an RNAse protection analysis of JAK3 expression in human leukemia derived cell lines and normal bone marrow. On the left side the undigested full-length JAK3 and actin probes are denoted. The RNA sources are labeled above each lane. To show the specificity of the protected bands, reactions with no RNA and with tRNA (tRNA) were also conducted. The position of the protected JAK3 and actin species are denoted on the right side.

The present invention provides a novel protein tyrosine kinase, JAK3, and a polynucleotide sequence encoding JAK3 polypeptide. The amino acid sequence of JAK3 indicates that it is a new member of the JAK family of non-receptor tyrosine kinases. In normal human bone marrow, JAK3 is highly expressed in the CD34+/lin− fraction which is enriched in hematopoietic stem/progenitor cells. As JAK kinases have been shown to be involved in the signal transduction pathways of various hematopoietic growth factors, it is likely that JAK3 plays a role in the growth factor modulated differentiation/proliferation/survival of hematopoietic stem/progenitor cells.

In a first embodiment, the invention provides a substantially pure JAK3 polypeptide consisting essentially of the amino acid sequence of SEQ ID NO:2. The full-length JAK3 polypeptide sequence has 1082 amino acids with a molecular weight of approximately 121 kD. JAK3 has 48% identity and 67% similarity with JAK2 (murine), 41% identity and 61% similarity with JAK1 (human), and 40% identity and 60% similarity with TYK-2 (human). Comparison of human JAK3 with the rat JAK3 shows 77% identity and 84% similarity (Takahashi, T. and Shirasawa, T., *FEBS Letters*, 342:124, 1994).

The term "substantially pure" or "isolated" as used herein, refers to JAK3 polypeptide which is substantially flee of other proteins, lipids, carbohydrates, nucleic acids, or other materials with which it is naturally associated. One skilled in the art can purify JAK3 using standard techniques for protein purification. The substantially pure polypeptide will yield a single major band on a non-reducing polyacrylamide gel. The purity of the JAK3 polypeptide can also be determined by amino-terminal amino acid sequence analysis.

The invention includes a functional polypeptide, JAK3, and functional fragments thereof. As used herein, the term "functional polypeptide" refers to a polypeptide which possesses a biological function or activity which is identified through a defined functional assay and which is associated with a particular biologic, morphologic, or phenotypic alteration in the cell. Functional fragments of the JAK3 polypeptide, includes fragments of JAK3 as long as the activity, e.g., protein tyrosine kinase activity, of JAK3 remains. Smaller peptides containing the biological activity of JAK3 are included in the invention. The biological function, for example, can vary from a polypeptide fragment as small as an epitope to which an antibody molecule can bind to a large polypeptide which is capable of participating in the characteristic induction or programming of phenotypic changes within a cell. An enzymatically functional JAK3 polypeptide or fragment thereof possesses JAK3 tyrosine kinase activity. A "functional polynucleotide" denotes a polynucleotide which encodes a functional polypeptide as described herein.

Minor modifications of the JAK3 primary amino acid sequence may result in proteins which have substantially equivalent activity as compared to the JAK3 polypeptide described herein. Such modifications may be deliberate, as by site-directed mutagenesis, or may be spontaneous. All of the polypeptides produced by these modifications are included herein as long as the tyrosine kinase activity of JAK3 is present. Further, deletion of one or more amino acids can also result in a modification of the structure of the resultant molecule without significantly altering its kinase activity. This can lead to the development of a smaller active molecule which may have broader utility. For example, it is possible to remove amino or carboxyl terminal amino acids which may not be required for JAK3 kinase activity.

The JAK3 polypeptide of the invention also includes conservative variations of the polypeptide sequence. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The invention also provides an isolated polynucleotide sequence consisting essentially of a polynucleotide sequence encoding a polypeptide having the amino acid sequence of SEQ ID NO:2. As used herein, "polynucleotide" refers to a polymer of deoxyribonucleotides or ribonucleotides, in the form of a separate fragment or a larger construct. The term "isolated" as used herein includes polynucleotides substantially free of other nucleic acids, proteins, lipids, carbohydrates or other materials with which it is naturally associated. Polynucleotide sequences of the invention include DNA, cDNA and RNA sequences which encode JAK3. It is understood that all polynucleotides encoding all or a portion of JAK3 are also included herein, as long as they encode a polypeptide with JAK3 kinase activity. Such polynucleotides include naturally occurring, synthetic, and intentionally manipulated polynucleotides. For example, JAK3 polynucleotide may be subjected to site-directed mutagenesis. The polynucleotide sequence for JAK3 also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of JAK3 polypeptide encoded by the nucleotide sequence is functionally unchanged. In addition, the invention also includes a polynucleotide consisting essentially of a polynucleotide sequence encoding a polypeptide having an amino acid sequence of SEQ ID NO:2 and having at least one epitope for an antibody immunoreactive with JAK3 polypeptide.

Specifically disclosed herein is a cDNA sequence which encodes JAK3 which comprising a 3,807 base pair (bp) predicted coding region for JAK3, 167 base pairs of 5' untranslated and 394 base pairs of 3' untranslated sequence (SEQ. ID NO:1). The cDNA includes an open reading frame of 3,246 base pairs encoding a protein of about 1082 amine acids, having a molecular weight of about 121 kD. The putative initiating methionine shows the strongest homology with the Kozak consensus sequence (Kozak, M., *Nucleic Acids Research*, 15:8125, 1987). At the 3' end, an in frame stop codon defines the C-terminus of the JAK3 protein at position 3242.

The polynucleotide encoding JAK3 includes the nucleotide sequence in FIG. 1 (SEQ ID NO:1), as well as nucleic acid sequences complementary to that sequence. A complementary sequence may include an antisense nucleotide. When the sequence is RNA, the deoxynucleotides A, G, C, and T of FIG. 1 are replaced by ribonucleotides A, G, C, and U, respectively. Also included in the invention are fragments of the above-described nucleic acid sequences that are at least 15 bases in length, which is sufficient to permit the fragment to selectively hybridize to DNA that encodes the protein of FIG. 1 (SEQ ID NO:2) under physiological conditions.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences; 2) antibody screening of expression libraries to detect cloned DNA fragments with shared structural features; and 3) PCR amplification of a desired nucleotide sequence using oligonucleotide primers.

Preferably the JAK3 polynucleotide of the invention is derived from a mammalian organism, and most preferably from human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amine acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low mount of mRNA sequences relating to the polypeptide of interest are present. In other words, by using stringent hybridization conditions directed to avoid nonspecific binding, it is possible, for example, to allow the autoradiographic visualization of a specific cDNA clone by the hybridization of the target DNA to that single probe in the mixture which is its complete complement (Wallace, et al., *Nucl. Acid Res.*, 9:879, 1981).

The development of specific DNA sequences encoding JAK3 can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.*, 11:2325, 1983).

A preferred method for obtaining genomic DNA for example is Polymerase Chain Reaction (PCR), which relies on an in vitro method of nucleic acid synthesis by which a particular segment of DNA is specifically replicated. Two oligonucleotide primers that flank the DNA fragment to be amplified are utilized in repeated cycles of heat denaturation of the DNA, annealing of the primers to their complementary sequences, and extension of the annealed primers with DNA polymerase. These primers hybridize to opposite strands of the target sequence and are oriented so that DNA synthesis by the polymerase proceeds across the region between the primers. Since the extension products themselves are also complementary to and capable of binding primers, successive cycles of amplification essentially double the amount of the target DNA synthesized in the previous cycle. The result is an exponential accumulation of the specific target fragment, approximately $2^n$, where n is the number of cycles of amplification performed (see PCR Protocols, Eds. Innis, et al., Academic Press, Inc., 1990, incorporated herein by reference).

A cDNA expression library, such as lambda gt11, can be screened indirectly for JAK3 peptides having at least one epitope, using antibodies specific for JAK3. Such antibodies can be either polyclonally or monoclonally derived and used to detect expression product indicative of the presence of JAK3 cDNA. The polynucleotide sequence for JAK3 also includes sequences complementary to the polynucleotide encoding JAK3 (antisense sequences). Antisense nucleic acids are DNA or RNA molecules that are complementary to at least a portion of a specific mRNA molecule (Weintraub, *Scientific American*, 262:40, 1990). The invention embraces all antisense polynucleotides capable of inhibiting production of JAK3 polypeptide. In the cell, the antisense nucleic acids hybridize to the corresponding mRNA, forming a double-stranded molecule. The antisense nucleic acids may interfere with the translation of the mRNA since the cell will not translate a mRNA that is double-stranded, or alternatively, the double-stranded mRNA is degraded. Antisense oligomers of about 15 nucleotides are preferred, since they are easily synthesized, small enough to enter the cell, and are less likely to cause problems than larger molecules when introduced into the target JAK3-producing cell. The use of antisense methods to inhibit the translation of genes is well known in the art (Marcus-Sakura, Anal. Biochem., 172:289, 1988).

In addition, ribozyme nucleotide sequences for JAK3 are included in the invention. Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, IJ. Amer. Med. Assn., 260:3030, 1988). A major advantage of this approach is that, because they are sequence-specific, only mRNAs with particular sequences are inactivated.

There are two basic types of ribozymes namely, tetrahymena-type (Hasselhoff, Nature, 334:585, 1988) and "hammerhead"-type. Tetrahymena-type ribozymes recognize sequences which are four bases in length, while "hammerhead"-type ribozymes recognize base sequences 11-18 bases in length. The longer the recognition sequence, the greater the likelihood that sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

DNA sequences encoding JAK3 can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the JAK3 polynucleotide sequences may be inserted into a recombinant expression vector. The term "recombinant expression vector" refers to a plasmid, virus or other vehicle known in the art that has been manipulated by insertion or incorporation of the JAK3 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., Gene, 56:125, 1987), the pMSXND expression vector for expression in mammalian cells (Lee and Nathans, J. Biol. Chem., 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding JAK3 can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional vital and plasmid DNA vectors capable of expression and replication in a host are known in the art. Such vectors are used to incorporate DNA sequences of the invention.

Methods which are well known to those skilled in the art can be used to construct expression vectors containing the JAK3 coding sequence and appropriate transcriptional/translational control signals. These methods include in vitro recombinant DNA techniques, synthetic techniques, and in vivo recombination/genetic techniques. See, for example, the techniques described in Maniatis, et al., 1989 Molecular Cloning A Laboratory Manual, Cold Spring Harbor Laboratory, N.Y.

A variety of host-expression vector systems may be utilized to express the JAK3 coding sequence. These include but are not limited to microorganisms such as bacteria transformed with recombinant bacteriophage DNA, plasmid DNA or cosmid DNA expression vectors containing the JAK3 coding sequence; yeast transformed with recombinant yeast expression vectors containing the JAK3 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the JAK3 coding sequence; insect cell systems infected with recombinant virus expression vectors (e.g., baculovirus) containing the JAK3 coding sequence; or animal cell systems infected with recombinant virus expression vectors (e.g., retroviruses, adenovirus, vaccinia virus) containing the JAK3 coding sequence, or transformed animal cell systems engineered for stable expression. Since JAK3 has not been confirmed to contain carbohydrates, both bacterial expression systems as well as those that provide for translational and post-translational modifications may be used; e.g., mammalian, insect, yeast or plant expression systems.

Depending on the host/vector system utilized, any of a number of suitable transcription and translation elements, including constitutive and inducible promoters, transcription enhancer elements, transcription terminators, etc. may be used in the expression vector (see e.g., Bitter, et al., 1987, Methods in Enzymology, 153:516-544). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted JAK3 coding sequence.

In bacterial systems a number of expression vectors may be advantageously selected depending upon the use intended for the expressed. For example, when large quantities of JAK3 are to be produced, vectors which direct the expression of high levels of fusion protein products that are readily purified may be desirable. Those which are engineered to contain a cleavage site to aid in recovering are preferred. Such vectors include but are not limited to the E. coli expression vector pUR278 (Ruther, et al., EMBO J., 2:1791, 1983), in which the JAK3 coding sequence may be ligated into the vector in frame with the lac Z coding region so that a hybrid -lac Z protein is produced; pIN vectors (Inouye and Inouye, Nucleic Acids Res., 13:3101, 1985; Van Heeke and Schuster, J. Biol. Chem. 264:5503, 1989) and the like.

In yeast, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu and Grossman, 31987, Acad. Press, N.Y., Vol. 153, pp.516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger and Kimmel, Acad. Press, N.Y., Vol. 152, pp. 673–684; and The Molecular Biology of the Yeast Saccharomyces, 1982, Eds. Strathern, et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. D. M. Glover, 1986, IRL Press, Wash., D.C.). Alternatively, vectors may be used which promote integration of foreign DNA sequences into the yeast chromosome.

In cases where plant expression vectors are used, the expression of the JAK3 coding sequence may be driven by any of a number of promoters. For example, viral promoters such as the 35S RNA and 19S RNA promoters of CaMV (Brisson, et al., *Nature*, 310:511, 1984), or the coat protein promoter to TMV (Takamatsu, et al., *EMBO J.*, 6:307, 1987) may be used; alternatively, plant promoters such as the small subunit of RUBISCO (Coruzzi, et al., *EMBO J.*, 3:1671–1680, 1984; Broglie, et al., *Science*, 224:838, 1984); or heat shock promoters, e.g., soybean hsp17.5-E or hsp17.3-B (Gurley, et al., *Mol. Cell. Biol.*, 6:559, 1986) may be used. These constructs can be introduced into plant cells using Ti plasmids, Ri plasmids, plant virus vectors, direct DNA transformation, microinjection, electroporation, etc. For reviews of such techniques see, for example, Weissbach and Weissbach, 1988, Methods for Plant Molecular Biology, Academic Press, N.Y., Section VIII, pp. 421–463; and Grierson and Corey, 1988, Plant Molecular Biology, 2d Ed., Blackie, London, Ch. 7–9.

An alternative expression system which could be used to express is an insect system. In one such system, *Autographa californica* nuclear polyhedrosis virus (AcNPV) is used as a vector to express foreign genes. The virus grows in *Spodoptera frugiperda* cells. The JAK3 coding sequence may be cloned into non-essential regions (for example the polyhedrin gene) of the virus and placed under control of an AcNPV promoter (for example the polyhedrin promoter). Successful insertion of the JAK3 coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith, et al., *J. Virol.*, 46:584, 1983; Smith, U.S. Pat. No. 4,215,051).

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and advantageously, secretion of the gene product may be used as host cells for the expression of JAK3. Mammalian cell lines may be preferable. Such host cell lines may include but are not limited to CHO, VERO, BHK, HeLa, COS, MDCK, –293, and WI38.

Mammalian cell systems which utilize recombinant viruses or viral elements to direct expression may be engineered. For example, when using adenovirus expression vectors, the JAK3 coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the protein in infected hosts (e.g., see Logan and Shenk, *Proc. Natl. Acad. Sci. USA* 81:3655, 1984). Alternatively, the vaccinia virus 7.5K promoter may be used. (e.g., see, Mackett, et al., *Proc. Natl. Acad. Sci. USA*, 79:7415, 1982; Mackett, et al., *J. Virol.*, 49:857, 1984; Panicali, et al., *Proc. Natl. Acad. Sci. USA*, 79:4927, 1982). Of particular interest are vectors based on bovine papilloma virus which have the ability to replicate as extrachromosomal elements (Sarver, et al., *Mol. Cell. Biol.*, 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as, for example, the neo gene. Alternatively, the retroviral genome can be modified for use as a vector capable of introducing and directing the expression of the JAK3 gene in host cells (Cone and Mulligan, *Proc. Natl. Acad. Sci. USA*, 81:6349, 1984). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with the JAK3 cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler, et al., *Cell*, 11:223, 1977), hypoxanthine-guanine phosphoribosyltransferase (Szybalska and Szybalski, *Proc. Natl. Acad. Sci. USA*, 48:2026, 1962), and adenine phosphoribosyltransferase (Lowy, et al., *Cell*, :22:817, 1980) genes can be employed in tk$^-$, hgprt$^-$ or aprt$^-$ cells respectively. Also, antimetabolite resistance can be used as the basis of selection for dhfr, which confers resistance to methotrexate (Wigler, et al., *Natl. Acad. Sci. USA*, 77:3567, 1980; O'Hare, et al., *Proc. Natl. Acad. Sci. USA*, 78:1527, 1981); gpt, which confers resistance to mycophenolic acid (Mulligan and Berg, *Proc. Natl. Acad. Sci. USA*, 78:2072, 1981; neo, which confers resistance to the aminoglycoside G418 (Colberre-Garapin, et al., *J. Mol. Biol.*, 150:1, 1981); and hygro, which confers resistance to hygromycin (Santerre, et al., *Gene*, 30:147, 1984) genes. Recently, additional selectable genes have been described, namely trpB, which allows cells to utilize indole in place of tryptophan; hisD, which allows cells to utilize histinol in place of histidine (Hartman and Mulligan, *Proc. Natl. Acad. Sci. USA*, 85:8047, 1988); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

Transformation of a host cell with recombinant DNA may be carried out by conventional techniques as are well known to those skilled in the art. Where the host is prokaryotic, such as E. coli, competent cells which are capable of DNA uptake can be prepared from cells harvested after exponential growth phase and subsequently treated by the CaCl$_2$ method using procedures well known in the art. Alternatively, MgCl$_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the JAK3 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors*, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

The invention includes antibodies immunoreactive with or which bind to JAK3 polypeptide or functional fragments thereof. Antibody which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., *Nature*, 256:495, 1975). The term antibody as used in this invention is meant to include intact molecules as well as fragments thereof, such as Fab and F(ab')$_2$, which are capable of binding an epitopic determinant on JAK3. The antibodies of the invention include antibodies which bind to the polypeptide of SEQ ID NO:2 and which bind with immunoreactive fragments of SEQ ID NO:2.

The term "antibody" as used in this invention includes intact molecules as well as fragments thereof, such as Fab, F(ab')$_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable genetically fused single chain molecule.

Methods of making these fragments are known in the art. (See for example, Harlow and Lane, *Antibodies: A Laboratory Manual*, Cold Spring Harbor Laboratory, New York (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the JAK3 polypeptide of the invention can be prepared using an intact polypeptide or fragments containing small peptides of interest as the immunizing antigen. The polypeptide such as SEQ ID NO:2 used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology*, Wiley Interscience, 1991, incorporated by reference). It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

The invention also provides a method for detecting a cell proliferative disorder associated with JAK3 in a subject, comprising contacting a target cellular component containing JAK3, with a reagent which detects JAK3. The target cell component can be nucleic acid, such as DNA or RNA, or it can be protein. When the component is nucleic acid, the reagent is a nucleic acid probe or PCR primer. When the cell component is protein, the reagent is an antibody probe. The probes can be detectably labeled, for example, with a radioisotope, a fluorescent compound, a bioluminescent compound, a chemiluminescent compound, a metal chelator, or an enzyme. Those of ordinary skill in the art will know of other suitable labels for binding to the antibody, or will be able to ascertain such, using routine experimentation.

For purposes of the invention, an antibody or nucleic acid probe specific for JAK3 may be used to detect the presence of JAK3 polypeptide (using antibody) or polynucleotide (using nucleic acid probe) in biological fluids or tissues. Oligonucleotide primers based on any coding sequence region in the JAK3 sequence are useful for amplifying DNA, for example by PCR. Any specimen containing a detectable amount of polynucleotide or antigen can be used. A preferred sample of this invention is blood or a tissue of liver, lung, kidney, spleen and intestine. Preferably the subject is human. When the cell proliferative disorder associated with JAK3 is a hematopoietic cell disorder, it may include leukemia, myelodysplasia, polyethemia vera, thrombocytosis and aplastic anemia, for example.

Monoclonal antibodies used in the method of the invention are suited for use, for example, in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The term "immunometric assay" or "sandwich immunoassay", includes simultaneous sandwich, forward sandwich and reverse sandwich immunoassays. These terms are well understood by those skilled in the art. Those of skill will also appreciate that antibodies according to the present invention will be useful in other variations and forms of assays which are presently known or which may be developed in the future. These are intended to be included within the scope of the present invention.

Monoclonal antibodies can be bound to many different carriers and used to detect the presence of JAK3 polypeptide. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such using routine experimentation.

In performing the assays it may be desirable to include certain "blockers" in the incubation medium (usually added with the labeled soluble antibody). The "blockers" are added to assure that non-specific proteins, proteases, or antiheterophilic immunoglobulins to anti-JAK3 immunoglobulins present in the experimental sample do not cross-link or destroy the antibodies on the solid phase support, or the radiolabeled indicator antibody, to yield false positive or false negative results. The selection of "blockers" therefore may add substantially to the specificity of the assays described in the present invention.

It has been found that a number of nonrelevant (i.e., nonspecific) antibodies of the same class or subclass (isotype) as those used in the assays (e.g., IgG1, IgG2a, IgM, etc.) can be used as "blockers". The concentration of the "blockers" (normally 1–100 µg/µl) may be important, in order to maintain the proper sensitivity yet inhibit any unwanted interference by mutually occurring cross reactive proteins in the specimen.

In using a monoclonal antibody for the in vivo detection of antigen, the detectably labeled monoclonal antibody is given in a dose which is diagnostically effective. The term "diagnostically effective" means that the mount of detectably labeled monoclonal antibody is administered in sufficient quantity to enable detection of the site having the JAK3 antigen for which the monoclonal antibodies are specific.

The concentration of detectably labeled monoclonal antibody which is administered should be sufficient such that the binding to those cells having JAK3 is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. The dosage of monoclonal antibody can vary from about 0.001 mg/m$^2$ to about 500 mg/m$^2$, preferably 0.1 mg/m$^2$ to about 200 mg/m$^2$, most preferably about 0.1 mg/m$^2$ to about 10 mg/m$^2$. Such dosages may vary, for example, depending on whether multiple injections are given, tumor burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

A monoclonal antibody useful in the method of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The present invention also provides a method for treating a subject with a cell proliferative disorder associated with JAK3 comprising administering to a subject with the disorder a therapeutically effective amount of reagent which modulates JAK3. In hematopoietic cancers, for example, the JAK3 nucleotide sequence may be under-expressed as compared to expression in a normal cell, therefore, it is possible to design appropriate therapeutic or diagnostic techniques directed to this sequence. Thus, where a cell-proliferative disorder is associated with the expression of JAK3 associated with malignancy, nucleic acid sequences that modulate JAK3 expression at the transcriptional or translational level can be used. In cases when a cell proliferative disorder or abnormal cell phenotype is associated with the under expression of JAK3, for example, nucleic acid sequences encoding JAK3 (sense) could be administered to the subject with the disorder.

The term "cell-proliferative disorder" denotes malignant as well as non-malignant cell populations which often appear to differ from the surrounding tissue both morphologically and genotypically. Such disorders may be associated, for example, with absence of expression of JAK3. Essentially, any disorder which is etiologically linked to expression of JAK3 could be considered susceptible to treatment with a reagent of the invention which modulates JAK3 expression.

The term "modulate" envisions the suppression of JAK3 gene expression when JAK3 is over-expressed. When JAK3 is over-expressed, an antisense polynucleotide for JAK3 can be introduced into the cell. Alternatively, when a cell proliferative disorder is associated with under-expression of JAK3 polypeptide, a sense polynucleotide sequence (the DNA coding strand) encoding JAK3 polypeptide can be introduced into the cell. The term "therapeutically effective" amount refers to that amount of reagent includes that amount which modulates JAK3 expression o kinase activity such that the symptoms of the disorder are reduced.

The present invention also provides gene therapy for the treatment of cell proliferative disorders which are mediated by JAK3. Such therapy would achieve its therapeutic effect by introduction of the appropriate JAK3 polynucleotide which contains a JAK3 gene (sense), into cells of subjects having the proliferative disorder. Delivery of sense JAK3 polynucleotide constructs can be achieved using a recombinant expression vector such as a chimeric virus or a colloidal dispersion system. An expression vector including the JAK3 polynucleotide sequence could be introduced to the subject's cells ex vivo after removing, for example, stem cells from a subject's bone marrow. The cells are then reintroduced into the subject, (e.g., into subject's bone marrow).

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammmary tumor virus (MuMTV), and Rous Sarcoma Virus (RSV), and gibbon ape leukemia virus (GaLV), which provides a broader host range than many of the murine viruses. A number of additional retroviral vectors can incorporate multiple genes. All of these vectors can transfer or incorporate a gene for a selectable marker so that transduced cells can be identified and generated. By inserting a JAK3 sequence (including promoter region) of interest into the viral vector, along with another gene which encodes the ligand for a receptor on a specific target cell, for example, the vector is now target specific. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the JAK3 sense or antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Another targeted delivery system for JAK3 polynucleotide is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 um can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In general, the compounds bound to the surface of the targeted delivery system will be ligands and receptors which will allow the targeted delivery system to find and "home in" on the desired cells. A ligand may be any compound of interest which will bind to another compound, such as a receptor.

In general, surface membrane proteins which bind to specific effector molecules are referred to as receptors. In the present invention, antibodies are preferred receptors. Antibodies can be used to target liposomes to specific cell-surface ligands. For example, certain antigens expressed specifically on tumor cells, referred to as tumor-associated antigens (TAAs), may be exploited for the purpose of targeting JAK3 antibody-containing liposomes directly to the malignant tumor. Since the JAK3 gene product may be indiscriminate with respect to cell type in its action, a targeted delivery system offers a significant improvement over randomly injecting non-specific liposomes. Preferably, the target tissue is human brain, colon, lung, and renal cancers. A number of procedures can be used to covalently attach either polyclonal or monoclonal antibodies to a liposome bilayer. Antibody-targeted liposomes can include monoclonal or polyclonal antibodies or fragments thereof such as Fab, or F(ab')$_2$, as long as they bind efficiently to an antigenic epitope on the target cells. Liposomes may also be targeted to cells expressing receptors for hormones or other serum factors.

For use in the diagnostic research and therapeutic applications suggested above, kits are also provided by the invention. The invention provides a diagnostic kit useful for the detection of a target cellular component indicative of a cell proliferative disorder associated with JAK3 comprising carrier means being compartmentalized to receive in close confinement therein one or more containers comprising a first container containing a probe for detection of JAK3 nucleic acid. Such a kit may comprise a carrier means being compartmentalized to receive in close confinement one or more container means such as vials, tubes, and the like, each of the container means comprising one of the separate elements to be used in the method.

For example, one of the container means may comprise a probe which is or can be detectably labelled. Such probe may be an antibody or nucleotide specific for a target protein or a target nucleic acid, respectively, wherein the target is indicative, or correlates with, the presence of JAK3 of the invention. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radionucleotide label.

The above disclosure generally describes the present invention. A more complete understanding can be obtained by reference to the following specific examples which are provided herein for purposes of illustration only and are not intended to limit the scope of the invention.

EXAMPLE 1

CLONING AND SEQUENCING OF JAK3

In order to clone the cDNA for a new member of the JAK family of non-receptor protein tyrosine kinases, degenerate oligonucleotides corresponding to parts of the highly conserved tyrosine kinase domain were used to amplify first strand cDNA from oligo (dT) primed, reverse transcribed, CD34+ total RNA from normal human bone marrow.

1. Bone Marrow Fractions

Iliac crest bone marrow was aspirated from consenting adult volunteers under an IRB approved protocol. Mononuclear cells were separated by Ficoll-Hypaque (Pharmacia, Piscataway, N.J.) density gradient separation. Cell subsets were purified by immunomagnetic separation (Strauss, L. C., et al., *The American Journal of Pediatric Hematology/Oncology*, 13:217, 1991, Civin, C. I., et al, *Bone Marrow Purging and Processing*, 1990). Positive selection of the CD34+ fraction was done by incubation of the mononuclear fraction with 0.5 ug CD34 (HPCA-1, Becton Dickinson, San Jose, Calif.) antibody per $10^6$ cells for 30 minutes at 4° C. Cells were washed twice in RPMI 1640 (Sigma, St. Louis, Mo.) then resuspended in RPMI-1640 containing 1% human serum albumin at $5\times10^7$ cells/ml and incubated with sheep anti-mouse IgG1 conjugated immunomagnetic microspheres for 30 minutes at 4° C. The CD34+ bound cells were released from the microspheres by treatment with chymopapain (Chymodiactin TM, Boots USA, Lincolnshire Ill.; final concentration 200 U/ml, 15 min., RT). The microspheres were removed from the free (CD34+ enriched) cells using a magnetic particle concentrator (Dynal, Great Neck, N.Y.). CD34+ cells were further purified to obtain CD34+/Lin− cells by negative selection as described by Gore (Gore, S. D. et al., *Blood*, 8:1681, 1991).

2. Isolation of RNA

Poly A+ RNA was isolated from human hematopoietic cell lines using the Mini Ribosep mRNA isolation kit (Becton Dickinson, San Jose, Calif.). Total RNA from bone marrow cells and hematopoietic cell lines was extracted using the guanidium thiocyanate method (Chomczynski, P. and Sacchi, N., *Anal Biochem.*, 162:156, 1987).

3. Cloning of JAK3

Total RNA isolated from CD34+ cells (see above) was reverse transcribed with Superscript Moloney murine-leukemia-virus reverse transcriptase (BRL, Gaithersburg, Md.) using oligo d(T) (Boehringer Mannheim, Germany) for priming. PCR amplification was carried out using degenerate oligonucleotides based on the highly conserved sequence motifs VHRDLA (5' GTNCA(T,C)(T,C)(C,A) GNGA(T,C) (TN GC3') AND DVWSYG (5' CCC(G,A)TAN(G,C)(A,T) CCA NAC (G,A)TC3') from the PTK catalytic domain (Wilks, A. F., et al., *Gene*, 85:67, 1989, Wilks, A. F., *Methods in Enzymology*, 200:533, 1991). To facilitate subcloning of the amplified PCR products Not 1 and Sal 1 sites were included as part of the PCR primers.

The resultant 226 bp bands were isolated after electrophoresis in agarose gels and cloned into the Not 1/Sal 1 sites of pBluescript II KS− (Stratagene, La Jolla, Calif.). After sequencing, products containing known tyrosine kinase motifs were compared to reported sequences using the NCBI BlastN program (Altschul, S. F., et al., *Journal of Molecular Biology*, 215:403, 1990). The fragment did not match any other sequences in the databases but was most closely related to members of the JAK family of tyrosine kinases at 65–70% nucleic acid identity.

The conditions for RT-PCR and thermal RACE were carried out as described by Frohman (Frohman, M. A., *Methods in Enzymology*, 218:340, 1993). KG1a poly A+ RNA was used as the substrate for RACE. The 5' and 3' ends of JAK3 were also amplified from normal human bone marrow cDNA isolated from a λgt10 human bone marrow library (Clonetech, Palo Alto, Calif.) using primers specific for JAK3 with primers specific for the arms of λgt10 under the same PCR conditions used for RACE.

4. Sequencing of JAK3

To correct for PCR errors, multiple overlapping partial clones of JAK3 isolated from KG 1a and bone marrow cells were sequenced and compared using the dideoxy DNA sequencing method (USB, Cleveland, Ohio) (Sanger, F., et al., *Proc. Natl. Acad. Sci. USA*, 74:5463, 1977). To verify some regions, RT PCR amplified fragments from normal human bone marrow and exon containing portions of normal human JAK3P 1 genomic clones (see below) were also sequenced.

5. RNAse Protection Assays

Efforts to obtain the full-length JAK3 clone by screening of several libraries proved unsuccessful. Therefore, RNAse protection assay were developed utilizing the initial PCR amplified kinase domain fragment to screen for leukemic derived cell lines expressing JAK3. RNAse protection assays were carried out using the MAXIscript T3 in vitro Transcription Kit (Ambion, Austin, Tex.). Briefly, an antisense RNA probe was synthesized by runoff transcription using Bacteriophage T3 RNA polymerase on a pBluescript II KS– (Stratagene, La Jolla, Calif.) template linearized downstream of the JAK3 207 nucleotide PTK domain fragment. The resulting $^{32}$Pα-UTP labelled 249 base RNA probe was hybridized with approximately 5 μg of total RNA from hematopoietic cell lines and RNA from approximately equal numbers of cells from normal human bone marrow sub-fractions. RNA-RNA hybrids were treated with RNAse A and T, denatured and separated on an 8M-Urea, 6% acrylamide gel and exposed to film (Kodak X-OMAT) (Melton, D. A., et al., *Nucleic Acids Research*, 12:7035, 1984). As an internal standard, a β-actin probe was also included with each hybridization reaction.

6. JAK3 nucleotide and predicted amino acid sequence

Of the cell lines tested in this initial screening, JAK3 was most highly expressed by the myeloblastic cell line KG1a. Thermal RACE and PCR was employed to cone the full-length cDNA of JAK3 from KG1a and normal human bone marrow cells (Frohman, M. A., *Therman RACE, Methods in Enzymology*, 218:340, 1993). Using several rounds of RACE we isolated 3,807 bp of JAK3 cDNA, a region which covers the entire predicted coding region for JAK3, 167 bases of 5' untranslated and 394 bases of 3' untranslated sequence. FIG. 1 shows the nucleotide and predicted amino acid sequence of JAK3. The cDNA includes an open reading frame of 3,246 bases that predicts a protein of 1082 amino acids with a molecular weight of 121 kD. The putative initiating methionine shows the strongest homology with the Kozak consensus sequence (Kozak, M., *Nucleic Acids Research*, 15:8125, 1987). At the 3' end an in frame stop codon defines the C terminus of the JAK3 protein at position 3242.

EXAMPLE 2

SEQUENCE COMPARISON BETWEEN JAK3 AND OTHER JAK FAMILY MEMBER

1. Amino acid comparison between JAK3 and other JAK family members

The initial identification of JAK3 as the fourth member of the JAK family was based on a database search using the 207 bp PCR fragment. The comparison of full-length-JAK3 with the other JAK family members is shown in FIG. 2. Sequences of JAK family members were aligned using the Pileup program (GCG Company, Madison, Wis.). The numbering system begins with the initiating methionine of the JAK family members. The numbering system does not take into account the insertion of gaps and, therefore, should be only regarded as a relative measure of location. The fifth line in the figure shows a consensus sequence derived if three out of four JAK family members have the identical amino acid in that position. Full-length JAK3 has 48% identity and 67% similarity with JAK2 (murine), 41% identity and 61% similarity with JAK1, and 40% identity and 60% similarity with TYK-2. In addition, recently, small fragments of tyrosine kinases by PCR approaches from a human breast cancer cell line (TK5) and rat brain (Ptk-2) have been isolated (Cance, W. G., et al., *Int. J. Cancer*, 54:571, 1993, Sánchez, M. P., et al., *Proc. Natl. Acad. Sci. USA*, 91:1819, 1994). Both of these TK's show 93% identity with JAK3 in this short region, while rat Jak3 shares 99% identity in this region. How JAK3 relates to these PTKs must await the isolation of their full coding regions.

2. Amino acid comparison between JAK3 and rat JAK3

FIG. 3 shows the comparison of JAK3 with the recently reported rat Jak3. The sequences of human JAK3 and rat Jak3 were aligned using the Pileup program (GCG Company, Madison, Wis.) The amino acids of each member are numbered beginning with the initiating methionine. The comparison shows 77% identity and 84% similarity making it likely that these genes are homologies (Takahashi, T. and Shirasawa, T., *FEBS Letters*, 342:124, 1994).

EXAMPLE 3

CHARACTERIZATION OF JAK3 EXPRESSION

1. RNAse protection analysis of JAK3 expression in leukemic derived cell lines

To investigate the hematopoietic expression of JAK3, the RNAse protection assay was used utilizing the 206 bp PCR kinase domain fragment of JAK3 to screen leukemic derived cell lines (see above). Briefly, a 32P α-UTP labelled antisense RNA probe to the kinase domain of JAK3 was hybridized with 5 ugs total RNA from hematopoietic cell lines. A β-actin probe was also included with each reaction as an internal standard, with the exception of the bone marrow and ML-1 populations, which were separately assayed for JAK3 and actin. As shown in FIG. 4a, a protected band migrating at the expected size is seen in a number of lanes. Positive signals were discernable for the Molt-16, Molt-3, KG1, KG1a, PB697, Nalm-16, Nalm-6, and TF-1 cell lines. These positive cell lines represent various forms of leukemia; the Molt lines were derived from T-lineage ALL, the KG1 lines from AML, PB697 and the Nalm lines are B lineage ALL, and TF-1 was established from an erythroleukemia. No signals were seen from RNA derived from the ML-1, HL60, K562, or Daudi cell lines representing additional AML, APL, CML, and Burkitt's leukemia lines, respectively.

2. Northern blot analysis of JAK3 expression in leukemic derived cell lines

Figure 4B:
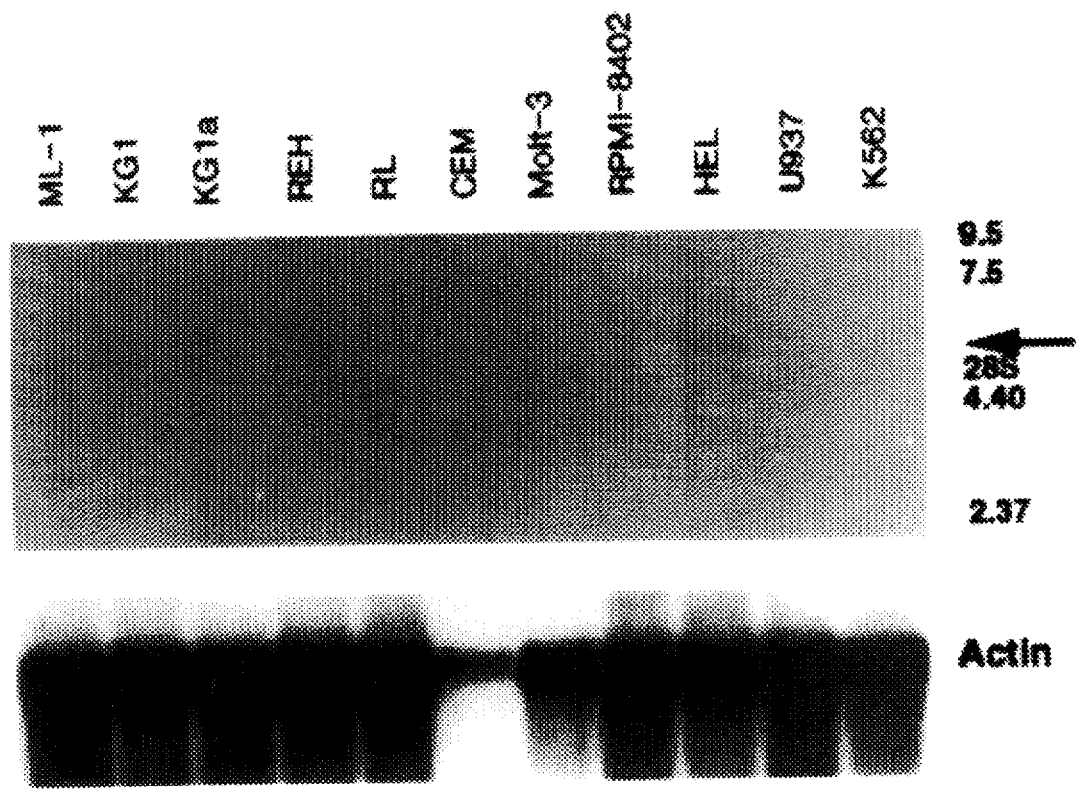
FIG. 4b shows a northern blot analysis of JAK3 expression in human leukemia derived cell lines. (Upper half) A Northern blot of poly A+ RNA from the leukemia-derived cell lines noted above each lane was hybridized with a randomly primed $^{32}$P α-dCTP labeled probe corresponding to a 1.8 kb fragment of JAK3. The relative mobilities of the 28S ribosomal RNA and RNA markers are denoted on the right. The JAK3 band is indicated by an arrow. (Lower half) The blot was stripped and reprobed with actin.

Although the coding region of the cDNAs for the JAK family are ~3400 bp, the 5' and 3' untranslated regions and polyadenylation result in transcripts ranging from 4.4 kbp for JAK1, 4.8 kbp for JAK2, 5.4 kbp for TYK-2 and 4.0 kbp for rat Jak3. To investigate the size of JAK3 message, a Northern blot with poly A+ RNA isolated from a number of hematopoietic cell lines was probed with a 1.8 kbp JAK3 fragment. 5 μg of poly A+RNA samples from hematopoietic cell lines were incubated at 55° C. for 15 minutes with 50% formamide, 6.5% formaldehyde, and 1×MOPS. Following the addition of formaldehyde loading buffer and ethidium bromide, RNA samples were electrophoresed in a 1.2% agarose gel containing 1×MOPS and 11% formaldehyde. Following electrophoresis, gels were transferred by capillary action to nitrocellulose 47. Sambrook J., Fritsch E. F., Maniatis T.: Molecular Cloning. A Laboratory Manual. 1989). As is evident from FIG. 4b (upper half), JAK3 is not a very highly expressed message. Even after an exposure of 17 days at –80° C. with two intensifying screens, signals were barely visible in the lanes containing RNA from the HEL, REH, KG1, and KG1 a cell lines (HEL represents an erythroleukemia, REH is derived from a B-lineage ALL, and the KG1 and KG1a cell lines are myeloblastic). RNA markers give an estimate of 5.8 kbp for the JAK3 transcript in these cells.

3. Northern blot analysis of JAK3 expression in non-hematopoietic tissues

To assess the expression of JAK3 in non-hematopoietic normal adult tissues, a Northern blot containing 2 µg of poly A+ RNA from human heart, brain, placenta, lung, liver, skeletal muscle, kidney, and pancreas was screened. (Clonetech, Palo Alto, Calif.). Northern blots were prehybridized for 2 hrs in 50% formamide, 5× SSPE, 10× Denhardt's, 2% SDS, and 100 ug/ml denatured salmon sperm DNA (Clonetech). Blots were hybridized with a randomly primed $^{32}$P-dCTP labeled probe corresponding to a 1.8 kbp fragment of JAK3 cDNA (Feinberg, A. P. and Vogelstein, B., *Anal. Biochem.*, 132:6, 1983). The blots were exposed to film (Kodak x-OMAT) for 1'/days at −80° C. between two intensifying screens.

Figure 4C:
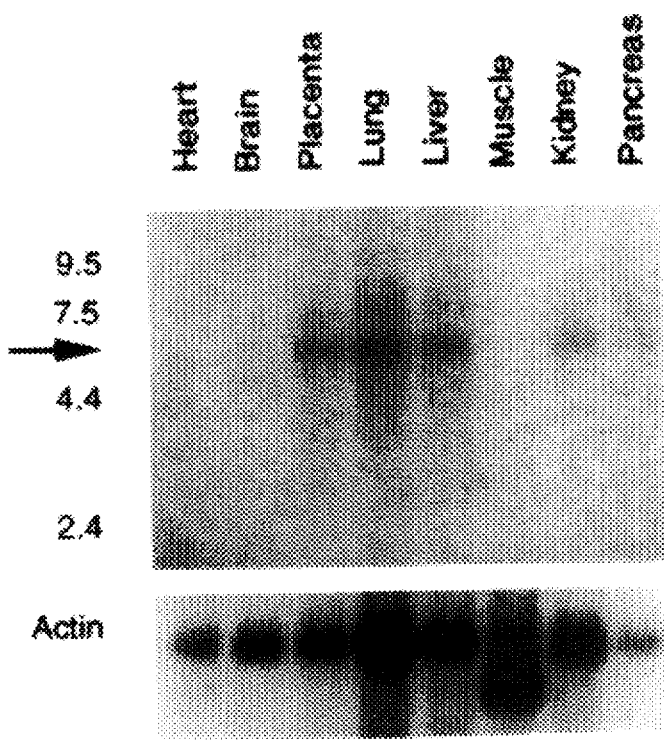
FIG. 4c shows a northern blot analysis of JAK3 expression in non-hematopoietic tissues. A multiple tissue Northern blot (Clonetech, Palo Alto, Calif.) containing 2 ug of poly A+ RNA from human heart, brain, placenta, lung, live, skeletal muscle, kidney, and pancreas was hybridized with the same probe as in FIG. 4b. The relative mobilities of the RNA markers are denoted on the left. The JAK3 band is indicated by an arrow.
Figure 5A:
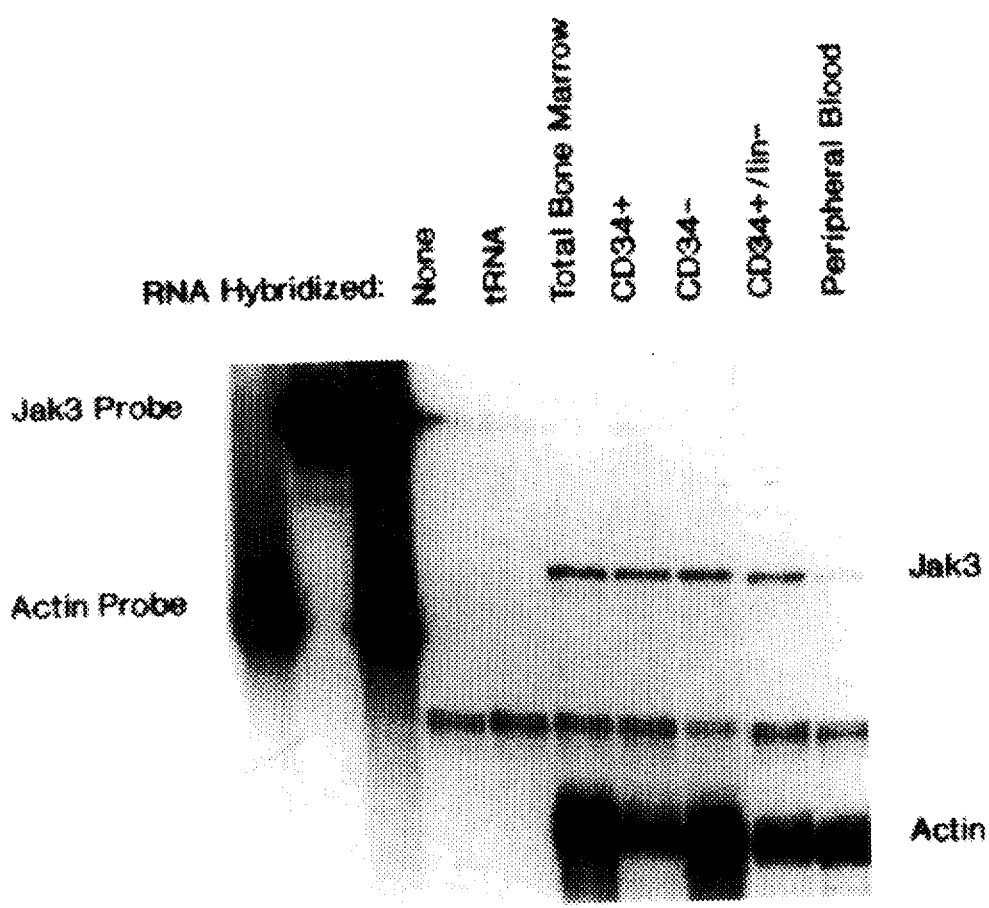
FIG. 5a shows an RNAse protection analysis of JAK3 expression in normal bone marrow fractions. On the left side the undigested, full-length, JAK3 and actin probes are denoted. The RNA sources are labeled above each lane. To show the specificity of the protected bands, reactions with no RNA (None) and with tRNA (tRNA) were also conducted. The protected JAK3 and actin species are denoted on the right side. The unlabelled band that migrates between the JAK3 and actin bands is present in all lanes, including the no RNA and tRNA lanes, and is a result of incomplete digestion of the probe.

When the same JAK3 fragment was also used to probe a Northern blot containing RNA from non-hematopoietic human tissues (FIG. 4c), signals are seen from placenta, lung, liver, kidney, and pancreas, all with a similar message size of 5.8 kbp with possibly an additional less distinct band at −7.5 kbp. Unlike rat JAK3, which is expressed in rat heart and brain, no signals were seen from the RNA representing heart, brain, or skeletal muscle.

4. RNAse Protection of JAK3 expression in normal bone marrow fractions

Although the initial JAK3 fragment was generated by PCR amplification of CD34+ enriched bone marrow RNA, it remained a possibility that JAK3 expression was restricted to contaminating CD34− cells. To determine which populations of normal bone marrow express JAK3, fractions representing whole BM, CD34+, CD34− (i.e. depleted of CD34+ cells), CD34+/lin−, as well as peripheral blood were isolated. RNA was then extracted and used to perform the RNAse protection assay. The same probe used in FIG. 4a was hybridized with approximately 1-5 µgs of RNA from normal total bone marrow, bone marrow subfractions, and from peripheral blood. As an internal standard, a β-actin probe was also included with each reaction as a standard for the amount and quality of RNA loaded in each sample. The presence of a band that migrates between the JAK3 and actin bands in all lanes, including the no RNA and tRNA control lanes, is a result of incomplete digestion of the probe. All of the sample lanes give a protected JAK3 band migrating at the expected size. However, probably because of the limited amounts of RNA obtained from several fractions, the actin bands indicate a variation in total RNA loaded for each sample.

Figure 5B:
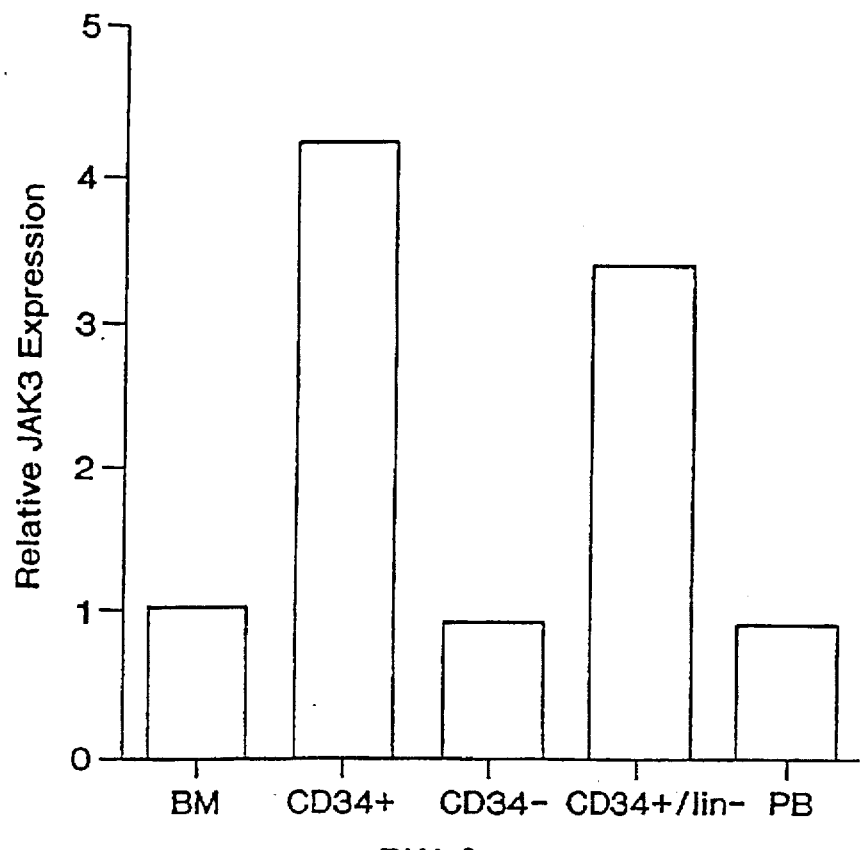
FIG. 5b shows a phosphorimage analysis of bone marrow fractions. Following exposure to film, the gel shown in FIG. 5a was exposed to a phosphorimage screen (Molecular Dynamics, Sunnyvale, Calif.). Bands were quantified using the ImageQuantify program and normalized relative to the actin signals.

To determine the relative expression of JAK3 in these different populations, the bands were quantified by phosphorimager scanning and normalized relative to the actin signal. FIG. 5b shows the phosphorimage analysis of bone marrow fractions. Following exposure to film, the gel shown in FIG. 5b was exposed to a phosphor-image screen (Molecular Dynamics, Sunnyvale, Calif.). Bands were quantified using the ImageQuantify program and normalized relative to the actin signals. FIG. 5b shows the strongest relative signals result from the CD34+ RNA and the even more stem cell enriched CD34+/lin− RNA sample. Thus, JAK3 is most highly expressed in this primitive population of cells and may play a role in transducing the signal of receptor functioning in the proliferative, survival and/or developmental pathways of these cells. JAK3 is also expressed in the CD34− and peripheral blood fractions and is thus likely to be involved with a subset of receptors involved in differentiated cell signalling, in analogy to JAK1, JAK2, and TYK-2.

EXAMPLE 4

CHROMOSOMAL LOCALIZATION OF THE JAK3 GENE

1. Somatic cell hybrid analysis

To determine the chromosomal localization of the JAK3 gene, a human/rodent somatic cell hybrid mapping panel, NIGMS #2, which included human, mouse and hamster genomic DNA controls was screened by PCR (Drwinga, H., et al., *Genomics*, 16:311, 1993, Dubois, B. and Naylor, S., *Genomics*, 16:315, 1993). In this panel, most of the somatic cell hybrid samples contained DNA from a single specific human chromosome in a rodent background. To preclude cDNA contamination problems, a primer pair was selected that resulted in a PCR product from genomic DNA that was larger than the produce resulting from cDNA due to the presence of intronic sequence. The plus strand oligo 5'AGC-CGCCTCCTTCTCT3' (SEQ. ID NO:3) and minus strand oligo 5'CGGCAGCAGCTTAGCTAGG3' (SEQ. ID NO:4) amplify an approximate 410 base pair product from human genomic DNA and a 156 base pair product from JAK3 cDNA.

For PCR, 100 ngs of genomic DNA from each hybrid cell line were used as the target for amplification. PCR amplification was performed using the following parameters: (94° C., 1'->55° C., 1'->72° C., 2')×30->72° C., 15'. The final concentrations of reagents were 0.2 mM dNTP, 50 mM KCL, 3.0 mM Mg, 0.1 U Taq Polymerase/ml, and 2.5 mM each primer. The results from the PCR amplification were confirmed by Southern transfer and hybridization with a $^{32}$P γ-ATP kinase labelled oligo internal to the primers used for amplification.

Using the primer pair results in a PCR product only with DNA from human cells and not from mouse or hamster DNA. These oligonucleotides were then used on DNA samples from the library representing each of the human chromosomes. The amplified DNA was electrophoresed and after transfer to nitrocellulose was hybridized to a radiolabelled oligonucleotide internal to the other oligonucleotides used for the PCR. Only the DNA from a cell line containing human chromosome 19 gave a significant signal.

2. Fluorescence in situ hybridization

TYK-2 has also been mapped to chromosome 19 (JAK1 and JAK2 have been mapped to 1p31.3 and 9p24, respectively)[55,56] Several pairs of tyrosine kinases (eg. PDGFRβ and c-fms, PDGFα and c-kit, FLT3 and FLT1) have been shown to be closely linked, leading to the hypothesis that these receptor tyrosine kinases evolved by a trans duplication followed by a cis duplication.[57-60] In order to confirm the location of the gene on chromosome 19, to sublocalize the gene to a specific band, and to investigate the possibility that JAK3 and TYK-2 were linked, FISH experiment was carried out.

First clone containing approximately 80 kbp of the JAK3 gene was isolated by PCR screening of a P1 library using the same oligonucleotides used above. Briefly, P1 genomic clones of JAK3 were obtained by PCR screening of the Du Pont Merck Pharmaceutical Company Human Foreskin Fibroblast P1 Library #1 (DMPC-HFF#1)-(Genome System, St. Louis, Mo.). The clones were designated DMPC-HFF#1-1441, DMPC-HFF#1-1442, DMPC-HFF#1-1443 and identified using the same primer pairs and PCR conditions used for the screening of the human/rodent somatic cell hybrid mapping panel (see above). Partial sequencing of these P1 clones has confirmed that they represent genomic JAK3 DNA.

The P1 vector containing the approximate 80 kbp genomic clone 1441 of JAK3 was nick-translated with biotin-14 dATP (BRL, Gaithersburg, Md.), with 30% incorporation determined by tritium tracer incorporation. Slides with chromosome spreads were made from normal male lymphocytes cultured with BrdU (Bhatt, B., et al., *Nucleic*

Acids Res., 16:3951, 1988). Fluorescence in situ hybridization was performed as described by Lichter, et. al., (53. Lichter, P., Tang, C., Call, K., Hermanson, G., Evans, G., Housman, D., Ward, D.: High resolution mapping of human chromosome 11 by in situ hybridization with cosmid clones. Science 247:64, 1990) with modifications. Probe mix (2× SSCP, 60% formamide, 10% dextran sulfate, 4 ng/ul biotinylated probe, 300 ng/ul Cot-1 DNA (to suppress repeated sequences) and 150 ng/ul salmon sperm DNA was denatured at 70° C. for 5 minutes, preannealed at 37° C. for 40 minutes, placed on slides and hybridized at 37° C. overnight. Slides were washed in 70% formamide/2× SSC at 43° C. for 20 minutes, and 2 changes of 2× SSC at 37° C. for 5 minutes each. Biotinylated probe was detected with FITC-avidin and amplified with biotinylated anti-avidin, using reagents from an in situ hybridization kit (Oncor Inc., Gaithersburg, Md.), following the manufacturer's instructions.

Figure 6A:
FIG. 6a shows fluorescence in situ hybridization (FISH) used to identify the localization of JAK3. A plasmid containing approximately 80 kb of the JAK3 genomic DNA was labelled with biotin-14 dATP and hybridized to chromosome spreads made from normal human male lymphocytes cultured with BrdU. Analysis of 36 metaphase cells showed 20 cells (56%) had at least one pair of signals (involving both chromatids of a single chromosome), an example of which is shown. Paired signals are indicated by arrows.
Figure 6B:
FIG. 6b shows G-banding of chromosome spreads. The same metaphase spread shown in FIG. 6a was G-banded by fluorescence plus Giemsa (FPG) after hybridization, photographed and aligned with the color FISH slides. The position of the paired FISH signals on the G-banded chromosomes are indicated by arrows.
Figure 6C:
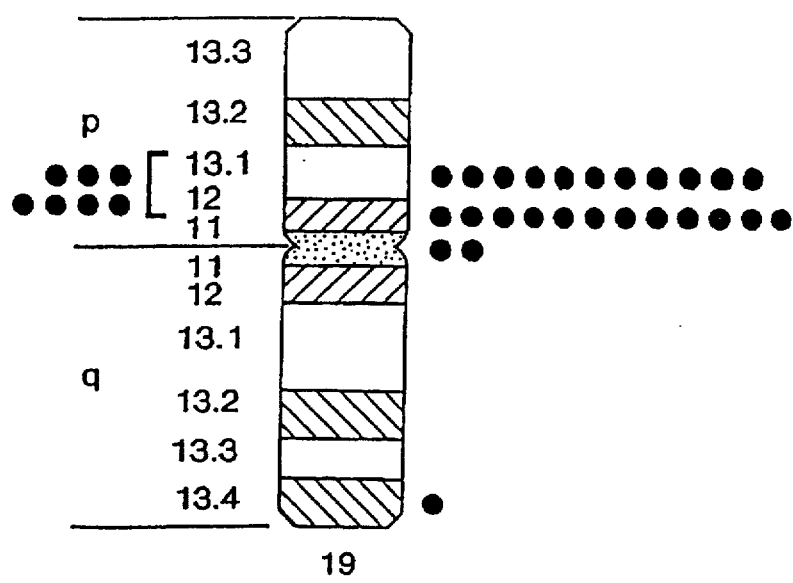
FIG. 6c shows an ideogram of human chromosome 19, revealing localization of JAK3 to 19p12-13.1. Each dot represents a paired signal seen on metaphase chromosomes. Signals clearly located on a single band are diagrammed to the right of the ideogram; those which could not be sublocalized to a single band are assigned to regions diagrammed to the left (brackets).

Analysis of 36 metaphase cells showed 20 cells (56%) had at least one pair of signals (involving both chromatids of a single chromosome). These 20 metaphases were photographed on color slide film (Kodak Ekttachrome 400HC) and 33 paired signals were seen, with all but one located on the proximal short arm of an F-group (chr. 19 or 20) chromosome, an example of which is shown in FIG. 6a. To determine the specific chromosome and band location of the signals, the hybridized slides were G-banded by FPG (fluorescence plus Giemsa), photographed, and aligned with the color slides to determine the subband location. FIG. 6b shows the position of the paired FISH signals on the G-banded chromosomes. All 33 signals were analyzable after banding and all were on chromosome 19, with most on bands p12-13.1 (FIG. 6c). Thus JAK3 may be located near TYK-2, which has been localized to 19p13.2. FIG. 6c is the ideogram of human chromosome 19, showing localization of JAK3 to 19p12-13.1. Each dot represents a paired signal seen on metaphase chromosomes. Signals clearly located on a single band are diagrammed to the right of the ideogram; those which could not be sublocalized to a single band are assigned to regions diagrammed to the left (brackets).

The foregoing is meant to illustrate, but not to limit, the scope of the invention. Indeed, those of ordinary skill in the art can readily envision and produce further embodiments, based on the teachings herein, without undue experimentation.

---

We claim:

1. An isolated polynucleotide sequence comprising a polynucleotide sequence encoding a polypeptide having an amino acid sequence of SEQ ID NO:2.

2. The isolated polynucleotide sequence of claim 1, comprising a polynucleotide sequence encoding a polypeptide having an amino acid sequence of SEQ ID NO:2 and having at least one epitope for an antibody immunoreactive with JAK3.

3. A host cell which contains the polynucleotide of claim 1 in an expression vector.

4. A recombinant expression vector which contains the polynucleotide of claim 1.

5. An isolated polynucleotide sequence, wherein the nucleotide sequence is selected from the group consisting of:

a) SEQ ID NO:1; and b) nucleic acid sequences encoding a polypeptide according to SEQ ID NO:2.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 3807 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

```
AAACAGTTAA  TACATATTTT  TTATGTTACG  TGTATTCTGT  ACAACAAAGT  AAGCTAGACA           60

AAAGAAAATG  TTTTCTCCTT  CCTGTGTGGG  ACTTTCCTCT  CGCTGCCTCC  CGGCTCTGCC          120

CGCCCTTCGA  AAGTCCAGGG  TCCCTGCCCG  CTAGGCAAGT  TGCACTC  ATG  GCA  CCT          176
                                                          Met  Ala  Pro
                                                           1

CCA  AGT  GAA  GAG  ACG  CCC  CTG  ATC  CCT  CAG  CGT  TCA  TGC  AGC  CTC  TTG  224
Pro  Ser  Glu  Glu  Thr  Pro  Leu  Ile  Pro  Gln  Arg  Ser  Cys  Ser  Leu  Leu
      5                        10                      15

TCC  ACG  GAG  GCT  GGT  GCC  CTG  CAT  GTG  CTG  CTG  CCC  GCT  CGG  GGC  CCC  272
Ser  Thr  Glu  Ala  Gly  Ala  Leu  His  Val  Leu  Leu  Pro  Ala  Arg  Gly  Pro
20                      25                      30                      35

GGG  CCC  CCC  CAG  CGC  CTA  TCT  TTC  TCC  TTT  GGG  GAC  CAC  TTG  GCT  GAG  320
Gly  Pro  Pro  Gln  Arg  Leu  Ser  Phe  Ser  Phe  Gly  Asp  His  Leu  Ala  Glu
                 40                      45                      50

GAC  CTG  TGC  GTG  CAG  GCT  GCC  AAG  GCC  AGC  GCG  ATC  CTG  CCT  GTG  TAC  368
Asp  Leu  Cys  Val  Gln  Ala  Ala  Lys  Ala  Ser  Ala  Ile  Leu  Pro  Val  Tyr
           55                      60                      65

CAC  TCC  CTC  TTT  GCT  CTG  GCC  ACG  GAG  GAC  CTG  TCC  TGC  TGG  TTC  CCC  416
His  Ser  Leu  Phe  Ala  Leu  Ala  Thr  Glu  Asp  Leu  Ser  Cys  Trp  Phe  Pro
                70                      75                      80

CGA  GCC  ACA  TCT  TCT  CCG  TGG  AGG  ATG  CCA  GCA  CCC  CAA  GTC  CTG  CTG  464
Arg  Ala  Thr  Ser  Ser  Pro  Trp  Arg  Met  Pro  Ala  Pro  Gln  Val  Leu  Leu
 85                      90                      95
```

-continued

| | | | | | | | | | | | | | | | | |
|---|---|---|---|---|---|---|---|---|---|---|---|---|---|---|---|---|
| TAC | AGG | ATT | CGC | TTT | TAC | TTC | CCC | AAT | TGG | TTT | GGG | CTG | GAG | AAG | TGC | 512 |
| Tyr | Arg | Ile | Arg | Phe | Tyr | Phe | Pro | Asn | Trp | Phe | Gly | Leu | Glu | Lys | Cys | |
| 100 | | | | | 105 | | | | | 110 | | | | | 115 | |
| CAC | CGC | TTC | GGG | CTA | CGC | AAG | GAT | TTG | GCC | AGT | GCT | ATC | CTT | GAC | CTG | 560 |
| His | Arg | Phe | Gly | Leu | Arg | Lys | Asp | Leu | Ala | Ser | Ala | Ile | Leu | Asp | Leu | |
| | | | | 120 | | | | | 125 | | | | | 130 | | |
| CCA | GTC | CTG | GAG | CAC | CTC | TTT | GCC | CAG | CAC | CGC | AGT | GAC | CTG | GTG | AGT | 608 |
| Pro | Val | Leu | Glu | His | Leu | Phe | Ala | Gln | His | Arg | Ser | Asp | Leu | Val | Ser | |
| | | | 135 | | | | | 140 | | | | | 145 | | | |
| GGG | CGC | CTC | CCC | CGT | GGC | CTC | AGT | CTC | AAG | GAG | CAG | GGT | GAG | TGT | CTC | 656 |
| Gly | Arg | Leu | Pro | Arg | Gly | Leu | Ser | Leu | Lys | Glu | Gln | Gly | Glu | Cys | Leu | |
| | | 150 | | | | | 155 | | | | | 160 | | | | |
| AGC | CTG | GCC | GTG | TTG | GAC | CTG | GCC | CGG | ATG | GCG | CGA | GAG | CAG | GCC | CAG | 704 |
| Ser | Leu | Ala | Val | Leu | Asp | Leu | Ala | Arg | Met | Ala | Arg | Glu | Gln | Ala | Gln | |
| 165 | | | | | 170 | | | | | 175 | | | | | | |
| CGG | CGG | GGA | GAG | CTG | CTG | AAG | ACT | GTC | AGC | TAC | AAG | GCC | TGC | CTA | CCC | 752 |
| Arg | Arg | Gly | Glu | Leu | Leu | Lys | Thr | Val | Ser | Tyr | Lys | Ala | Cys | Leu | Pro | |
| 180 | | | | | 185 | | | | | 190 | | | | | 195 | |
| CCA | AGC | CTG | CGC | GAC | CTG | ATC | CAG | GGC | CTG | AGC | TTC | GTG | ACG | GGG | AGG | 800 |
| Pro | Ser | Leu | Arg | Asp | Leu | Ile | Gln | Gly | Leu | Ser | Phe | Val | Thr | Gly | Arg | |
| | | | | 200 | | | | | 205 | | | | | 210 | | |
| CGT | ATT | CGG | AGG | ACG | GTG | GAG | AGC | CCC | CTG | CGC | CGG | GTG | GCC | GCC | TGC | 848 |
| Arg | Ile | Arg | Arg | Thr | Val | Glu | Ser | Pro | Leu | Arg | Arg | Val | Ala | Ala | Cys | |
| | | | 215 | | | | | 220 | | | | | 225 | | | |
| CAG | GCA | GAC | CGG | CAC | TCG | CTC | ATG | GCC | AAG | TAC | ATC | ATG | GAC | CTG | GAG | 896 |
| Gln | Ala | Asp | Arg | His | Ser | Leu | Met | Ala | Lys | Tyr | Ile | Met | Asp | Leu | Glu | |
| | | 230 | | | | | 235 | | | | | 240 | | | | |
| CGG | CTG | GAT | CCA | GCC | GGG | GCC | GCC | GAG | ACC | TTC | CAC | GTG | GGC | CTC | CCT | 944 |
| Arg | Leu | Asp | Pro | Ala | Gly | Ala | Ala | Glu | Thr | Phe | His | Val | Gly | Leu | Pro | |
| 245 | | | | | 250 | | | | | 255 | | | | | | |
| GGG | GCC | CTT | GGT | GGC | CAC | GAC | GGG | CTG | GGG | CTC | GTC | CGC | GTG | GCT | GGT | 992 |
| Gly | Ala | Leu | Gly | Gly | His | Asp | Gly | Leu | Gly | Leu | Val | Arg | Val | Ala | Gly | |
| 260 | | | | | 265 | | | | | 270 | | | | | 275 | |
| GAC | GGC | GGC | ATC | GCC | TGG | ACC | CAG | GGA | GAA | CAG | GAG | GTC | CTC | CAG | CCC | 1040 |
| Asp | Gly | Gly | Ile | Ala | Trp | Thr | Gln | Gly | Glu | Gln | Glu | Val | Leu | Gln | Pro | |
| | | | 280 | | | | | 285 | | | | | 290 | | | |
| TTC | TGC | GAC | TTT | CCA | GAA | ATC | GTA | GAC | ATT | AGC | ATC | AAG | CAG | GCC | CCG | 1088 |
| Phe | Cys | Asp | Phe | Pro | Glu | Ile | Val | Asp | Ile | Ser | Ile | Lys | Gln | Ala | Pro | |
| | | | 295 | | | | | 300 | | | | | 305 | | | |
| CGC | GTT | GGC | CCG | GCC | GGA | GAG | CAC | CGC | CTG | GTC | ACT | GTT | ACC | AGG | ACA | 1136 |
| Arg | Val | Gly | Pro | Ala | Gly | Glu | His | Arg | Leu | Val | Thr | Val | Thr | Arg | Thr | |
| | | 310 | | | | | 315 | | | | | 320 | | | | |
| GAC | AAC | CAG | ATT | TTA | GAG | GCC | GAG | TTC | CCA | GGG | CTG | CCC | GAG | GCT | CTG | 1184 |
| Asp | Asn | Gln | Ile | Leu | Glu | Ala | Glu | Phe | Pro | Gly | Leu | Pro | Glu | Ala | Leu | |
| 325 | | | | | 330 | | | | | 335 | | | | | | |
| TCG | TTC | GTG | GCG | CTC | GTG | GAC | GGC | TAC | TTC | CGG | CTG | ACC | ACG | GAC | TCC | 1232 |
| Ser | Phe | Val | Ala | Leu | Val | Asp | Gly | Tyr | Phe | Arg | Leu | Thr | Thr | Asp | Ser | |
| 340 | | | | | 345 | | | | | 350 | | | | | 355 | |
| CAG | CAC | TTC | TTC | TGC | AAG | GAG | GTG | GAC | CCG | AGG | CTG | CTG | GAG | GAA | GTG | 1280 |
| Gln | His | Phe | Phe | Cys | Lys | Glu | Val | Asp | Pro | Arg | Leu | Leu | Glu | Glu | Val | |
| | | | | 360 | | | | | 365 | | | | | 370 | | |
| GCC | GAG | CAG | TGC | CAC | GGC | CCC | ATC | ACT | CTG | GAC | TTT | GCC | ATC | AAC | AAG | 1328 |
| Ala | Glu | Gln | Cys | His | Gly | Pro | Ile | Thr | Leu | Asp | Phe | Ala | Ile | Asn | Lys | |
| | | | 375 | | | | | 380 | | | | | 385 | | | |
| CTC | AAG | ACT | GGG | GGC | TCA | CGT | CCT | GGC | TCC | TAT | GTT | CTC | CGC | CGC | ATC | 1376 |
| Leu | Lys | Thr | Gly | Gly | Ser | Arg | Pro | Gly | Ser | Tyr | Val | Leu | Arg | Arg | Ile | |
| | | 390 | | | | | 395 | | | | | 400 | | | | |
| CCC | CAG | GAC | TTT | GAC | AGC | TTC | CTC | CTC | ACT | GTC | TGT | GTC | CAG | AAC | CCC | 1424 |
| Pro | Gln | Asp | Phe | Asp | Ser | Phe | Leu | Leu | Thr | Val | Cys | Val | Gln | Asn | Pro | |
| 405 | | | | | 410 | | | | | 415 | | | | | | |

```
CTT GGT CCT GAT TAT AAG GGC TGC CTC ATC CGG CGC AGC CCC ACA GGA          1472
Leu Gly Pro Asp Tyr Lys Gly Cys Leu Ile Arg Arg Ser Pro Thr Gly
420                 425                 430                 435

ACC TTC CTT CTG GTT GGC CTC AGC CGA CCC CAC AGC AGT CTT CGA GAG          1520
Thr Phe Leu Leu Val Gly Leu Ser Arg Pro His Ser Ser Leu Arg Glu
                440                 445                 450

CTC CTG GCA ACC TGC TGG GAT GGG GGG CTG CAC GTA GAT GGG GTG GCA          1568
Leu Leu Ala Thr Cys Trp Asp Gly Gly Leu His Val Asp Gly Val Ala
            455                 460                 465

GTG ACC CTC ACT TCC TGC TGT ATC CCC AGA CCC AAA GAA AAG TCC AAC          1616
Val Thr Leu Thr Ser Cys Cys Ile Pro Arg Pro Lys Glu Lys Ser Asn
        470                 475                 480

CTG ATT GTG GTC CAG AGA GGT CAC AGC CCA CCC ACA TCA TCC TTG GTT          1664
Leu Ile Val Val Gln Arg Gly His Ser Pro Pro Thr Ser Ser Leu Val
    485                 490                 495

CAG CCC CAA TCC CAA TAC CAG CTG AGT CAG ATG ACA TTT CAC AAG ATC          1712
Gln Pro Gln Ser Gln Tyr Gln Leu Ser Gln Met Thr Phe His Lys Ile
500                 505                 510                 515

CCT GCT GAC AGC CTG GAG TGG CAT GAG AAC CTG GGC CAT GGG TCC TTC          1760
Pro Ala Asp Ser Leu Glu Trp His Glu Asn Leu Gly His Gly Ser Phe
                520                 525                 530

ACC AAG ATT TAC CGG GGC TGT CGC CAT GAG GTG GTG GAT GGG GAG GCC          1808
Thr Lys Ile Tyr Arg Gly Cys Arg His Glu Val Val Asp Gly Glu Ala
            535                 540                 545

CGA AAG ACA GAG GTG CTG CTG AAG GTC ATG GAT GCC AAG CAC AAG AAC          1856
Arg Lys Thr Glu Val Leu Leu Lys Val Met Asp Ala Lys His Lys Asn
        550                 555                 560

TGC ATG GAG TCA TTC CTG GAA GCA GCG AGC TTG ATG AGC CAA GTG TCG          1904
Cys Met Glu Ser Phe Leu Glu Ala Ala Ser Leu Met Ser Gln Val Ser
    565                 570                 575

TAC CGG CAT CTC GTG CTG CTC CAC GGC GTG TGC ATG GCT GGA GAC AGC          1952
Tyr Arg His Leu Val Leu Leu His Gly Val Cys Met Ala Gly Asp Ser
580                 585                 590                 595

ACC ATG GTC GAG GAA TTT GTA CAC CTG GGG GCC ATA GAC ATG TAT CTG          2000
Thr Met Val Glu Glu Phe Val His Leu Gly Ala Ile Asp Met Tyr Leu
                600                 605                 610

CGA AAA CGT GGC CAC CTG GTG CCA GCC AGC TGG AAG CTG CAG GTG GTC          2048
Arg Lys Arg Gly His Leu Val Pro Ala Ser Trp Lys Leu Gln Val Val
            615                 620                 625

AAA CAG CTG GCC TAC GCC CTC AAC TAT CTG GAG GAC AAA GGC CTG TCC          2096
Lys Gln Leu Ala Tyr Ala Leu Asn Tyr Leu Glu Asp Lys Gly Leu Ser
        630                 635                 640

CAT GGC AAT GTC TCT GCC CGG AAG GTG CTC CTG GCT CGG GAG GGG GCT          2144
His Gly Asn Val Ser Ala Arg Lys Val Leu Leu Ala Arg Glu Gly Ala
    645                 650                 655

GAT GGG AGC CCG CCC TTC ATC AAG CTG AGT GAC CCT GGG GTC AGC CCC          2192
Asp Gly Ser Pro Pro Phe Ile Lys Leu Ser Asp Pro Gly Val Ser Pro
660                 665                 670                 675

GCT GTG TTA AGC CTG GAG ATG CTC ACC GAC AGG ATC CCC TGG GTG GCC          2240
Ala Val Leu Ser Leu Glu Met Leu Thr Asp Arg Ile Pro Trp Val Ala
                680                 685                 690

CCC GAG TGT CTC CGG GAG GCG CAG ACA CTT AGC TTG GAA GCT GAC AAG          2288
Pro Glu Cys Leu Arg Glu Ala Gln Thr Leu Ser Leu Glu Ala Asp Lys
            695                 700                 705

TGG GGC TTC GGC GCC ACG GTC TGG GAA GTG TTT AGT GGC GTC ACC ATG          2336
Trp Gly Phe Gly Ala Thr Val Trp Glu Val Phe Ser Gly Val Thr Met
        710                 715                 720

CCC ATC AGT GCC CTA GAT CCT GCT AAG AAA CTC CAA TTT TAT GAG GAC          2384
Pro Ile Ser Ala Leu Asp Pro Ala Lys Lys Leu Gln Phe Tyr Glu Asp
    725                 730                 735
```

-continued

| | | | | | | | | | | | | | | | | |
|---|---|---|---|---|---|---|---|---|---|---|---|---|---|---|---|---|
| CGG | CAG | CAG | CTG | TCG | GCC | CCC | AAG | TGG | ACA | GAG | CTG | GCC | CTG | CTG | ATT | 2432 |
| Arg 740 | Gln | Gln | Leu | Ser 745 | Ala | Pro | Lys | Trp | Thr 750 | Glu | Leu | Ala | Leu | Leu 755 | Ile | |
| CAA | CAG | TGC | ATG | GCC | TAT | GAG | CCG | GTC | CAG | AGG | CCC | TCC | TTA | CGA | GCC | 2480 |
| Gln | Gln | Cys | Met | Ala 760 | Tyr | Glu | Pro | Val | Gln 765 | Arg | Pro | Ser | Leu | Arg 770 | Ala | |
| GTC | ATT | CGT | GAC | CTC | AAT | AGT | CTC | ATC | TCT | TCA | GAC | TAT | GAG | CTC | CTC | 2528 |
| Val | Ile | Arg 775 | Asp | Leu | Asn | Ser | Leu | Ile 780 | Ser | Ser | Asp | Tyr | Glu 785 | Leu | Leu | |
| TCA | GAC | CAC | ACC | TGG | TGC | CCT | GGC | ACT | CGT | GAT | GGG | CTG | TGG | AAT | GGT | 2576 |
| Ser | Asp | His 790 | Thr | Trp | Cys | Pro | Gly 795 | Thr | Arg | Asp | Gly | Leu 800 | Trp | Asn | Gly | |
| GCC | CAG | CTC | TAT | GCC | TGC | CAA | GAC | CCC | ACG | ATC | TTC | GAG | GAG | AGA | CAC | 2624 |
| Ala 805 | Gln | Leu | Tyr | Ala | Cys 810 | Gln | Asp | Pro | Thr | Ile 815 | Phe | Glu | Glu | Arg | His | |
| CTC | AAG | TAC | ATC | TCA | CAG | CTG | GGC | AAG | GGC | TTC | TTT | GGC | AGC | GTG | GAG | 2672 |
| Leu 820 | Lys | Tyr | Ile | Ser | Gln 825 | Leu | Gly | Lys | Gly | Phe 830 | Phe | Gly | Ser | Val | Glu 835 | |
| CTG | TGC | CGC | TAT | GAC | CCG | CTA | GGC | GAC | AAT | ACA | GGT | GCC | CTG | GTG | GCC | 2720 |
| Leu | Cys | Arg | Tyr | Asp 840 | Pro | Leu | Gly | Asp | Asn 845 | Thr | Gly | Ala | Leu | Val 850 | Ala | |
| GTG | AAA | CAG | CTG | CAG | CAC | AGC | GGG | CCA | GAC | CAG | CAG | AGG | GAC | TTT | CAG | 2768 |
| Val | Lys | Gln | Leu 855 | Gln | His | Ser | Gly | Pro 860 | Asp | Gln | Gln | Arg | Asp 865 | Phe | Gln | |
| CGG | GAG | ATT | CAG | ATC | CTC | AAA | GCA | CAG | CAC | AGT | GAT | TTC | ATT | GTC | AAG | 2816 |
| Arg | Glu | Ile | Gln 870 | Ile | Leu | Lys | Ala | Gln 875 | His | Ser | Asp | Phe | Ile 880 | Val | Lys | |
| TAT | CGT | GGT | GTC | AGC | TAT | GGC | CCG | GGC | CGC | CAG | AGC | CCT | GCG | CTG | GTC | 2864 |
| Tyr | Arg 885 | Gly | Val | Ser | Tyr | Gly 890 | Pro | Gly | Arg | Gln | Ser 895 | Pro | Ala | Leu | Val | |
| ATG | GAG | TAC | CTG | CCC | AGC | GGC | TGC | TTG | CGC | GAC | TTC | CTG | CAG | CGG | CAC | 2912 |
| Met 900 | Glu | Tyr | Leu | Pro | Ser 905 | Gly | Cys | Leu | Arg | Asp 910 | Phe | Leu | Gln | Arg | His 915 | |
| CGG | GGC | CTC | GAT | GCC | AGC | CGC | CTC | CTT | CTC | TAT | TCC | TCG | CAG | ATC | TGC | 2960 |
| Arg | Gly | Leu | Asp | Ala 920 | Ser | Arg | Leu | Leu | Leu 925 | Tyr | Ser | Ser | Gln | Ile 930 | Cys | |
| AAG | GGC | ATG | GAG | TAC | CTG | GGC | TCC | CGC | CGC | TGC | GTG | CAC | CGC | GAC | CTG | 3008 |
| Lys | Gly | Met | Glu 935 | Tyr | Leu | Gly | Ser | Arg 940 | Arg | Cys | Val | His | Arg 945 | Asp | Leu | |
| GCC | GCC | CGA | AAC | ATC | CTC | GTG | GAG | AGC | GAG | GCA | CAC | GTC | AAG | ATC | GCT | 3056 |
| Ala | Ala | Arg 950 | Asn | Ile | Leu | Val | Glu 955 | Ser | Glu | Ala | His | Val 960 | Lys | Ile | Ala | |
| GAC | TTC | GGC | CTA | GCT | AAG | CTG | CTG | CCG | CTT | GAC | AAA | GAC | TAC | TAC | GTG | 3104 |
| Asp | Phe | Gly 965 | Leu | Ala | Lys | Leu | Leu 970 | Pro | Leu | Asp | Lys | Asp 975 | Tyr | Tyr | Val | |
| GTC | CGC | GAG | CCA | GGC | CAG | AGC | CCC | ATT | TTC | TGG | TAT | GCC | CCC | GAA | TCC | 3152 |
| Val 980 | Arg | Glu | Pro | Gly | Gln 985 | Ser | Pro | Ile | Phe | Trp 990 | Tyr | Ala | Pro | Glu | Ser 995 | |
| CTC | TCG | GAC | AAC | ATC | TTC | TCT | CGC | CAG | TCA | GAC | GTC | TGG | AGC | TTC | GGG | 3200 |
| Leu | Ser | Asp | Asn | Ile 1000 | Phe | Ser | Arg | Gln | Ser 1005 | Asp | Val | Trp | Ser | Phe 1010 | Gly | |
| GTC | GTC | CTG | TAC | GAG | CTC | TTC | ACC | TAC | TGC | GAC | AAA | AGC | TGC | AGC | CCC | 3248 |
| Val | Val | Leu | Tyr | Glu 1015 | Leu | Phe | Thr | Tyr | Cys 1020 | Asp | Lys | Ser | Cys | Ser 1025 | Pro | |
| TCG | GCC | GAG | TTC | CTG | CGG | ATG | ATG | GGA | TGT | GAG | CGG | GAT | GTC | CCC | CGC | 3296 |
| Ser | Ala | Glu | Phe | Leu 1030 | Arg | Met | Met | Gly | Cys 1035 | Glu | Arg | Asp | Val | Pro 1040 | Arg | |
| CTC | TGC | CGC | CTC | TTG | GAA | CTG | CTG | GAG | GAG | GGC | CAG | AGG | CTG | CCG | GCG | 3344 |
| Leu | Cys | Arg 1045 | Leu | Leu | Glu | Leu | Leu 1050 | Glu | Glu | Gly | Gln | Arg 1055 | Leu | Pro | Ala | |

```
CCT CCT TGC TGC CCT GC TGAGGTGAGT TGCTACAGTG GCTGGAGAGA                    3391
Pro Pro Cys Cys Pro
1060

CGACATCTGC CTGCCTGCTG AGTGAGTTGC TACAGTGGCT GAGAGACGAC ATCTGCTCCA          3451

TGGCTGGTGG CCGACAGTAA TCTCACGCCG GACCTGCCGC AGCCCCTGCC CCAGACCTCT          3511

CACCATCACC GCCACCACCG TGCAGCTGCC ACCAACCCTG CACGCTACTG CTGCCTCAGT          3571

GGCTGTACCC AACAAGACCT GCTGACCCTC TGTCCCTACT GATTCCTCCT TGGGTGCAGC          3631

CTCAGAGTGC CTGAGGCCCA GAGGGTCTGG TCTGGTGAGC TCCTGAGGCC ACACAGCACC          3691

ATAAAGTCTC GCATCTACAG GCCTTTGATT ACCTCCTGGG ATGGGTGCTC ACTATCTACC          3751

CCAGACCAAC GCCACCTGCA GCCTGTGGAG TCAACTGCAG AATAAATCAC ACCCTA             3807
```

( 2 ) INFORMATION FOR SEQ ID NO:2:

( i ) SEQUENCE CHARACTERISTICS:
      ( A ) LENGTH: 1064 amino acids
      ( B ) TYPE: amino acid
      ( D ) TOPOLOGY: linear ( i i ) MOLECULE TYPE: protein ( x i ) SEQUENCE DESCRIPTION: SEQ ID NO:2:

```
Met Ala Pro Pro Ser Glu Glu Thr Pro Leu Ile Pro Gln Arg Ser Cys
 1               5                  10                  15

Ser Leu Leu Ser Thr Glu Ala Gly Ala Leu His Val Leu Leu Pro Ala
            20                  25                  30

Arg Gly Pro Gly Pro Pro Gln Arg Leu Ser Phe Ser Phe Gly Asp His
            35                  40                  45

Leu Ala Glu Asp Leu Cys Val Gln Ala Ala Lys Ala Ser Ala Ile Leu
    50                  55                  60

Pro Val Tyr His Ser Leu Phe Ala Leu Ala Thr Glu Asp Leu Ser Cys
65                  70                  75                  80

Trp Phe Pro Arg Ala Thr Ser Ser Pro Trp Arg Met Pro Ala Pro Gln
                85                  90                  95

Val Leu Leu Tyr Arg Ile Arg Phe Tyr Phe Pro Asn Trp Phe Gly Leu
                100                 105                 110

Glu Lys Cys His Arg Phe Gly Leu Arg Lys Asp Leu Ala Ser Ala Ile
            115                 120                 125

Leu Asp Leu Pro Val Leu Glu His Leu Phe Ala Gln His Arg Ser Asp
    130                 135                 140

Leu Val Ser Gly Arg Leu Pro Arg Gly Leu Ser Leu Lys Glu Gln Gly
145                 150                 155                 160

Glu Cys Leu Ser Leu Ala Val Leu Asp Leu Ala Arg Met Ala Arg Glu
                165                 170                 175

Gln Ala Gln Arg Arg Gly Glu Leu Leu Lys Thr Val Ser Tyr Lys Ala
            180                 185                 190

Cys Leu Pro Pro Ser Leu Arg Asp Leu Ile Gln Gly Leu Ser Phe Val
            195                 200                 205

Thr Gly Arg Arg Ile Arg Arg Thr Val Glu Ser Pro Leu Arg Arg Val
    210                 215                 220

Ala Ala Cys Gln Ala Asp Arg His Ser Leu Met Ala Lys Tyr Ile Met
225                 230                 235                 240

Asp Leu Glu Arg Leu Asp Pro Ala Gly Ala Ala Glu Thr Phe His Val
                245                 250                 255

Gly Leu Pro Gly Ala Leu Gly Gly His Asp Gly Leu Gly Leu Val Arg
            260                 265                 270
```

| | | | | | | | | | | | | | |
|---|---|---|---|---|---|---|---|---|---|---|---|---|---|
|Val|Ala|Gly 275|Asp|Gly|Gly|Ile|Ala 280|Trp|Thr|Gln|Gly|Glu 285|Gln|Glu|Val|
|Leu|Gln 290|Pro|Phe|Cys|Asp|Phe 295|Pro|Glu|Ile|Val|Asp 300|Ile|Ser|Ile|Lys|
|Gln 305|Ala|Pro|Arg|Val|Gly 310|Pro|Ala|Gly|Glu|His 315|Arg|Leu|Val|Thr|Val 320|
|Thr|Arg|Thr|Asp|Asn 325|Gln|Ile|Leu|Glu|Ala 330|Glu|Phe|Pro|Gly|Leu 335|Pro|
|Glu|Ala|Leu|Ser 340|Phe|Val|Ala|Leu|Val 345|Asp|Gly|Tyr|Phe|Arg 350|Leu|Thr|
|Thr|Asp|Ser 355|Gln|His|Phe|Phe|Cys 360|Lys|Glu|Val|Asp|Pro 365|Arg|Leu|Leu|
|Glu|Glu 370|Val|Ala|Glu|Gln|Cys 375|His|Gly|Pro|Ile|Thr 380|Leu|Asp|Phe|Ala|
|Ile 385|Asn|Lys|Leu|Lys|Thr 390|Gly|Gly|Ser|Arg|Pro 395|Gly|Ser|Tyr|Val|Leu 400|
|Arg|Arg|Ile|Pro|Gln 405|Asp|Phe|Asp|Ser|Phe 410|Leu|Leu|Thr|Val|Cys 415|Val|
|Gln|Asn|Pro|Leu 420|Gly|Pro|Asp|Tyr|Lys 425|Gly|Cys|Leu|Ile|Arg 430|Arg|Ser|
|Pro|Thr|Gly 435|Thr|Phe|Leu|Leu|Val 440|Gly|Leu|Ser|Arg|Pro 445|His|Ser|Ser|
|Leu|Arg 450|Glu|Leu|Leu|Ala|Thr 455|Cys|Trp|Asp|Gly|Gly 460|Leu|His|Val|Asp|
|Gly 465|Val|Ala|Val|Thr|Leu 470|Thr|Ser|Cys|Cys|Ile 475|Pro|Arg|Pro|Lys|Glu 480|
|Lys|Ser|Asn|Leu|Ile 485|Val|Val|Gln|Arg|Gly 490|His|Ser|Pro|Pro|Thr 495|Ser|
|Ser|Leu|Val|Gln 500|Pro|Gln|Ser|Gln|Tyr 505|Gln|Leu|Ser|Gln|Met 510|Thr|Phe|
|His|Lys|Ile 515|Pro|Ala|Asp|Ser|Leu 520|Glu|Trp|His|Glu|Asn 525|Leu|Gly|His|
|Gly|Ser 530|Phe|Thr|Lys|Ile|Tyr 535|Arg|Gly|Cys|Arg|His 540|Glu|Val|Val|Asp|
|Gly|Glu 545|Ala|Arg|Lys|Thr 550|Glu|Val|Leu|Leu|Lys 555|Val|Met|Asp|Ala|Lys 560|
|His|Lys|Asn|Cys|Met 565|Glu|Ser|Phe|Leu|Glu 570|Ala|Ala|Ser|Leu|Met 575|Ser|
|Gln|Val|Ser|Tyr 580|Arg|His|Leu|Val|Leu 585|Leu|His|Gly|Val|Cys 590|Met|Ala|
|Gly|Asp|Ser 595|Thr|Met|Val|Glu|Glu 600|Phe|Val|His|Leu|Gly 605|Ala|Ile|Asp|
|Met|Tyr 610|Leu|Arg|Lys|Arg|Gly 615|His|Leu|Val|Pro|Ala 620|Ser|Trp|Lys|Leu|
|Gln 625|Val|Val|Lys|Gln|Leu 630|Ala|Tyr|Ala|Leu|Asn 635|Tyr|Leu|Glu|Asp|Lys 640|
|Gly|Leu|Ser|His|Gly 645|Asn|Val|Ser|Ala|Arg 650|Lys|Val|Leu|Leu|Ala 655|Arg|
|Glu|Gly|Ala|Asp 660|Gly|Ser|Pro|Pro|Phe 665|Ile|Lys|Leu|Ser|Asp 670|Pro|Gly|
|Val|Ser|Pro 675|Ala|Val|Leu|Ser|Leu 680|Glu|Met|Leu|Thr|Asp 685|Arg|Ile|Pro|
|Trp|Val|Ala|Pro|Glu|Cys|Leu|Arg|Glu|Ala|Gln|Thr|Leu|Ser|Leu|Glu|

|     |     |     |     |     | 690 |     |     |     |     | 695 |     |     |     |     | 700 |     |     |     |     |
| --- | --- | --- | --- | --- | --- | --- | --- | --- | --- | --- | --- | --- | --- | --- | --- | --- | --- | --- | --- |
| Ala | Asp | Lys | Trp | Gly | Phe | Gly | Ala | Thr | Val | Trp | Glu | Val | Phe | Ser | Gly |
| 705 |     |     |     |     | 710 |     |     |     |     | 715 |     |     |     |     | 720 |

Val Thr Met Pro Ile Ser Ala Leu Asp Pro Ala Lys Lys Leu Gln Phe
                725                 730                 735

Tyr Glu Asp Arg Gln Gln Leu Ser Ala Pro Lys Trp Thr Glu Leu Ala
                740                 745                 750

Leu Leu Ile Gln Gln Cys Met Ala Tyr Glu Pro Val Gln Arg Pro Ser
                755                 760                 765

Leu Arg Ala Val Ile Arg Asp Leu Asn Ser Leu Ile Ser Ser Asp Tyr
                770                 775                 780

Glu Leu Leu Ser Asp His Thr Trp Cys Pro Gly Thr Arg Asp Gly Leu
785                 790                 795                 800

Trp Asn Gly Ala Gln Leu Tyr Ala Cys Gln Asp Pro Thr Ile Phe Glu
                805                 810                 815

Glu Arg His Leu Lys Tyr Ile Ser Gln Leu Gly Lys Gly Phe Phe Gly
                820                 825                 830

Ser Val Glu Leu Cys Arg Tyr Asp Pro Leu Gly Asp Asn Thr Gly Ala
                835                 840                 845

Leu Val Ala Val Lys Gln Leu Gln His Ser Gly Pro Asp Gln Gln Arg
850                 855                 860

Asp Phe Gln Arg Glu Ile Gln Ile Leu Lys Ala Gln His Ser Asp Phe
865                 870                 875                 880

Ile Val Lys Tyr Arg Gly Val Ser Tyr Gly Pro Gly Arg Gln Ser Pro
                885                 890                 895

Ala Leu Val Met Glu Tyr Leu Pro Ser Gly Cys Leu Arg Asp Phe Leu
                900                 905                 910

Gln Arg His Arg Gly Leu Asp Ala Ser Arg Leu Leu Leu Tyr Ser Ser
                915                 920                 925

Gln Ile Cys Lys Gly Met Glu Tyr Leu Gly Ser Arg Arg Cys Val His
930                 935                 940

Arg Asp Leu Ala Ala Arg Asn Ile Leu Val Glu Ser Glu Ala His Val
945                 950                 955                 960

Lys Ile Ala Asp Phe Gly Leu Ala Lys Leu Leu Pro Leu Asp Lys Asp
                965                 970                 975

Tyr Tyr Val Val Arg Glu Pro Gly Gln Ser Pro Ile Phe Trp Tyr Ala
                980                 985                 990

Pro Glu Ser Leu Ser Asp Asn Ile Phe Ser Arg Gln Ser Asp Val Trp
                995                 1000                1005

Ser Phe Gly Val Val Leu Tyr Glu Leu Phe Thr Tyr Cys Asp Lys Ser
                1010                1015                1020

Cys Ser Pro Ser Ala Glu Phe Leu Arg Met Met Gly Cys Glu Arg Asp
1025                1030                1035                1040

Val Pro Arg Leu Cys Arg Leu Leu Glu Leu Leu Glu Glu Gly Gln Arg
                1045                1050                1055

Leu Pro Ala Pro Pro Cys Cys Pro
                1060

( 2 ) INFORMATION FOR SEQ ID NO:3:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

AGCCGCCTCC TTCTCT  16

( 2 ) INFORMATION FOR SEQ ID NO:4:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:4:

CGGCAGCAGC TTAGCTAGG  19

( 2 ) INFORMATION FOR SEQ ID NO:5:

( i ) SEQUENCE CHARACTERISTICS:
      ( A ) LENGTH: 1082 amino acids
      ( B ) TYPE: amino acid
      ( C ) STRANDEDNESS: Not Relevant
      ( D ) TOPOLOGY: linear ( i i ) MOLECULE TYPE: protein ( x i ) SEQUENCE DESCRIPTION: SEQ ID NO:5:

```
Met Ala Pro Pro Ser Glu Glu Thr Pro Leu Ile Pro Gln Arg Ser Cys
 1               5                  10                  15

Ser Leu Leu Ser Thr Glu Ala Gly Ala Leu His Val Leu Leu Pro Ala
                20                  25                  30

Arg Gly Pro Gly Pro Pro Gln Arg Leu Ser Phe Ser Phe Gly Asp His
            35                  40                  45

Leu Ala Glu Asp Leu Cys Val Gln Ala Ala Lys Ala Ser Ala Ile Leu
        50                  55                  60

Pro Val Tyr His Ser Leu Phe Ala Leu Ala Thr Glu Asp Leu Ser Cys
65                  70                  75                  80

Trp Phe Pro Arg Ala Thr Ser Ser Pro Trp Arg Met Pro Ala Pro Gln
                85                  90                  95

Val Leu Leu Tyr Arg Ile Arg Phe Tyr Phe Pro Asn Trp Phe Gly Leu
               100                 105                 110

Glu Lys Cys His Arg Phe Gly Leu Arg Lys Asp Leu Ala Ser Ala Ile
           115                 120                 125

Leu Asp Leu Pro Val Leu Glu His Leu Phe Ala Gln His Arg Ser Asp
       130                 135                 140

Leu Val Ser Gly Arg Leu Pro Arg Gly Leu Ser Leu Lys Glu Gln Gly
145                 150                 155                 160

Glu Cys Leu Ser Leu Ala Val Leu Asp Leu Ala Arg Met Ala Arg Glu
                165                 170                 175

Gln Ala Gln Arg Arg Gly Glu Leu Leu Lys Thr Val Ser Tyr Lys Ala
            180                 185                 190

Cys Leu Pro Pro Ser Leu Arg Asp Leu Ile Gln Gly Leu Ser Phe Val
        195                 200                 205

Thr Gly Arg Arg Ile Arg Arg Thr Val Glu Ser Pro Leu Arg Arg Val
       210                 215                 220

Ala Ala Cys Gln Ala Asp Arg His Ser Leu Met Ala Lys Tyr Ile Met
225                 230                 235                 240

Asp Leu Glu Arg Leu Asp Pro Ala Gly Ala Ala Glu Thr Phe His Val
```

-continued

|     |     |     |     |     |     | 245 |     |     |     |     | 250 |     |     |     |     | 255 |     |
|---|---|---|---|---|---|---|---|---|---|---|---|---|---|---|---|---|---|
| Gly | Leu | Pro | Gly 260 | Ala | Leu | Gly | Gly | His 265 | Asp | Gly | Leu | Gly 270 | Leu | Val | Arg |
| Val | Ala | Gly 275 | Asp | Gly | Gly | Ile | Ala 280 | Trp | Thr | Gln | Gly | Gln 285 | Glu | Val |
| Leu | Gln | Pro 290 | Phe | Cys | Asp | Phe 295 | Pro | Glu | Ile | Val | Asp 300 | Ile | Ser | Ile | Lys |
| Gln | Ala | Pro | Arg | Val | Gly | Pro | Ala | Gly | Glu | His | Arg | Leu | Val | Thr | Val |
| 305 | | | | 310 | | | | 315 | | | | | | | 320 |
| Thr | Arg | Thr | Asp | Asn 325 | Gln | Ile | Leu | Glu | Ala 330 | Glu | Phe | Pro | Gly | Leu 335 | Pro |
| Glu | Ala | Leu | Ser 340 | Phe | Val | Ala | Leu | Val 345 | Asp | Gly | Tyr | Phe | Arg 350 | Leu | Thr |
| Thr | Asp | Ser 355 | Gln | His | Phe | Phe | Cys 360 | Lys | Glu | Val | Asp | Pro 365 | Arg | Leu | Leu |
| Glu | Glu | Val | Ala | Glu | Gln | Cys | His | Gly | Pro | Ile | Thr | Leu | Asp | Phe | Ala |
| 370 | | | | | 375 | | | | | 380 | | | | | |
| Ile | Asn | Lys | Leu | Lys | Thr | Gly | Gly | Ser | Arg | Pro | Gly | Ser | Tyr | Val | Leu |
| 385 | | | | 390 | | | | | 395 | | | | | | 400 |
| Arg | Arg | Ile | Pro | Gln 405 | Asp | Phe | Asp | Ser | Phe 410 | Leu | Leu | Thr | Val | Cys 415 | Val |
| Gln | Asn | Pro | Leu 420 | Gly | Pro | Asp | Tyr | Lys 425 | Gly | Cys | Leu | Ile | Arg 430 | Arg | Ser |
| Pro | Thr | Gly 435 | Thr | Phe | Leu | Leu | Val 440 | Gly | Leu | Ser | Arg | Pro 445 | His | Ser | Ser |
| Leu | Arg | Glu | Leu | Leu | Ala | Thr | Cys | Trp | Asp | Gly | Gly | Leu | His | Val | Asp |
| 450 | | | | | 455 | | | | | 460 | | | | | |
| Gly | Val | Ala | Val | Thr | Leu | Thr | Ser | Cys | Cys | Ile | Pro | Arg | Pro | Lys | Glu |
| 465 | | | | 470 | | | | | 475 | | | | | | 480 |
| Lys | Ser | Asn | Leu | Ile 485 | Val | Val | Gln | Arg | Gly 490 | His | Ser | Pro | Pro | Thr 495 | Ser |
| Ser | Leu | Val | Gln 500 | Pro | Gln | Ser | Gln | Tyr 505 | Gln | Leu | Ser | Gln | Met 510 | Thr | Phe |
| His | Lys | Ile 515 | Pro | Ala | Asp | Ser | Leu 520 | Glu | Trp | His | Glu | Asn 525 | Leu | Gly | His |
| Gly | Ser | Phe | Thr | Lys | Ile | Tyr | Arg | Gly | Cys | Arg | His | Glu | Val | Val | Asp |
| 530 | | | | | 535 | | | | | 540 | | | | | |
| Gly | Glu | Ala | Arg | Lys | Thr | Glu | Val | Leu | Leu | Lys | Val | Met | Asp | Ala | Lys |
| 545 | | | | | 550 | | | | | 555 | | | | | 560 |
| His | Lys | Asn | Cys | Met 565 | Glu | Ser | Phe | Leu | Glu 570 | Ala | Ala | Ser | Leu | Met 575 | Ser |
| Gln | Val | Ser | Tyr 580 | Arg | His | Leu | Val | Leu 585 | Leu | His | Gly | Val | Cys 590 | Met | Ala |
| Gly | Asp | Ser 595 | Thr | Met | Val | Glu | Glu 600 | Phe | Val | His | Leu | Gly 605 | Ala | Ile | Asp |
| Met | Tyr 610 | Leu | Arg | Lys | Arg | Gly 615 | His | Leu | Val | Pro | Ala 620 | Ser | Trp | Lys | Leu |
| Gln 625 | Val | Val | Lys | Gln | Leu 630 | Ala | Tyr | Ala | Leu | Asn 635 | Tyr | Leu | Glu | Asp | Lys 640 |
| Gly | Leu | Ser | His | Gly 645 | Asn | Val | Ser | Ala | Arg 650 | Lys | Val | Leu | Leu | Ala 655 | Arg |
| Glu | Gly | Ala | Asp 660 | Gly | Ser | Pro | Pro | Phe 665 | Ile | Lys | Leu | Ser | Asp 670 | Pro | Gly |

-continued

| | | | | | | | | | | | | | | | |
|---|---|---|---|---|---|---|---|---|---|---|---|---|---|---|---|
| Val | Ser | Pro 675 | Ala | Val | Leu | Ser | Leu 680 | Glu | Met | Leu | Thr | Asp 685 | Arg | Ile | Pro |
| Trp | Val 690 | Ala | Pro | Glu | Cys 695 | Leu | Arg | Glu | Ala | Gln 700 | Thr | Leu | Ser | Leu | Glu |
| Ala 705 | Asp | Lys | Trp | Gly 710 | Phe | Gly | Ala | Thr | Val 715 | Trp | Glu | Val | Phe | Ser | Gly 720 |
| Val | Thr | Met | Pro | Ile 725 | Ser | Ala | Leu | Asp | Pro 730 | Ala | Lys | Lys | Leu | Gln 735 | Phe |
| Tyr | Glu | Asp | Arg 740 | Gln | Gln | Leu | Ser | Ala 745 | Pro | Lys | Trp | Thr | Glu 750 | Leu | Ala |
| Leu | Leu | Ile 755 | Gln | Gln | Cys | Met | Ala 760 | Tyr | Glu | Pro | Val | Gln 765 | Arg | Pro | Ser |
| Leu | Arg 770 | Ala | Val | Ile | Arg | Asp 775 | Leu | Asn | Ser | Leu | Ile 780 | Ser | Ser | Asp | Tyr |
| Glu 785 | Leu | Leu | Ser | Asp | His 790 | Thr | Trp | Cys | Pro | Gly 795 | Thr | Arg | Asp | Gly | Leu 800 |
| Trp | Asn | Gly | Ala | Gln 805 | Leu | Tyr | Ala | Cys | Gln 810 | Asp | Pro | Thr | Ile | Phe 815 | Glu |
| Glu | Arg | His | Leu 820 | Lys | Tyr | Ile | Ser | Gln 825 | Leu | Gly | Lys | Gly | Phe 830 | Phe | Gly |
| Ser | Val | Glu 835 | Leu | Cys | Arg | Tyr | Asp 840 | Pro | Leu | Gly | Asp | Asn 845 | Thr | Gly | Ala |
| Leu | Val 850 | Ala | Val | Lys | Gln | Leu 855 | Gln | His | Ser | Gly | Pro 860 | Asp | Gln | Gln | Arg |
| Asp 865 | Phe | Gln | Arg | Glu | Ile 870 | Gln | Ile | Leu | Lys | Ala 875 | Gln | His | Ser | Asp | Phe 880 |
| Ile | Val | Lys | Tyr | Arg 885 | Gly | Val | Ser | Tyr | Gly 890 | Pro | Gly | Arg | Gln | Ser 895 | Pro |
| Ala | Leu | Val | Met 900 | Glu | Tyr | Leu | Pro | Ser 905 | Gly | Cys | Leu | Arg | Asp 910 | Phe | Leu |
| Gln | Arg | His 915 | Arg | Gly | Leu | Asp | Ala 920 | Ser | Arg | Leu | Leu | Leu 925 | Tyr | Ser | Ser |
| Gln | Ile 930 | Cys | Lys | Gly | Met | Glu 935 | Tyr | Leu | Gly | Ser | Arg 940 | Arg | Cys | Val | His |
| Arg 945 | Asp | Leu | Ala | Ala | Arg 950 | Asn | Ile | Leu | Val | Glu 955 | Ser | Glu | Ala | His 960 | Val |
| Lys | Ile | Ala | Asp | Phe 965 | Gly | Leu | Ala | Lys | Leu 970 | Leu | Pro | Leu | Asp | Lys 975 | Asp |
| Tyr | Tyr | Val | Val 980 | Arg | Glu | Pro | Gly | Gln 985 | Ser | Pro | Ile | Phe | Trp 990 | Tyr | Ala |
| Pro | Glu | Ser 995 | Leu | Ser | Asp | Asn | Ile 1000 | Phe | Ser | Arg | Gln | Ser 1005 | Asp | Val | Trp |
| Ser | Phe | Gly 1010 | Val | Val | Leu | Tyr | Glu 1015 | Leu | Phe | Thr | Tyr | Cys 1020 | Asp | Lys | Ser |
| Cys 1025 | Ser | Pro | Ser | Ala | Glu 1030 | Phe | Leu | Arg | Met | Met 1035 | Gly | Cys | Glu | Arg | Asp 1040 |
| Val | Pro | Arg | Leu | Cys 1045 | Arg | Leu | Leu | Glu | Leu 1050 | Leu | Glu | Glu | Gly | Gln 1055 | Arg |
| Leu | Pro | Ala | Pro 1060 | Pro | Cys | Cys | Pro | Ala 1065 | Glu | Val | Ser | Cys 1070 | Tyr | Ser | Gly |
| Trp | Arg | Asp 1075 | Asp | Ile | Cys | Leu | Pro 1080 | Ala | Glu | | | | | | |

( 2 ) INFORMATION FOR SEQ ID NO:6:

( i ) SEQUENCE CHARACTERISTICS:
   ( A ) LENGTH: 1129 amino acids
   ( B ) TYPE: amino acid
   ( C ) STRANDEDNESS: Not Relevant
   ( D ) TOPOLOGY: linear ( i i ) MOLECULE TYPE: protein ( x i ) SEQUENCE DESCRIPTION: SEQ ID NO:6:

| Met | Gly | Met | Ala | Cys | Leu | Thr | Met | Thr | Glu | Met | Glu | Ala | Thr | Ser | Thr |
|---|---|---|---|---|---|---|---|---|---|---|---|---|---|---|---|
| 1 | | | | 5 | | | | | 10 | | | | | 15 | |
| Ser | Pro | Val | His | Gln | Asn | Gly | Asp | Ile | Pro | Gly | Ser | Ala | Asn | Ser | Val |
| | | | 20 | | | | | 25 | | | | | 30 | | |
| Lys | Gln | Ile | Glu | Pro | Val | Leu | Gln | Val | Tyr | Leu | Tyr | His | Ser | Leu | Gly |
| | | 35 | | | | | 40 | | | | | 45 | | | |
| Gln | Ala | Glu | Gly | Glu | Tyr | Leu | Lys | Phe | Pro | Ser | Gly | Glu | Tyr | Val | Ala |
| | 50 | | | | | 55 | | | | | 60 | | | | |
| Glu | Glu | Ile | Cys | Val | Ala | Ala | Ser | Lys | Ala | Cys | Gly | Ile | Thr | Pro | Val |
| 65 | | | | 70 | | | | | 75 | | | | | 80 | |
| Tyr | His | Asn | Met | Phe | Ala | Leu | Met | Ser | Glu | Thr | Glu | Arg | Ile | Trp | Tyr |
| | | | | 85 | | | | | 90 | | | | | 95 | |
| Pro | Pro | Asn | His | Val | Phe | His | Ile | Asp | Glu | Ser | Thr | Arg | His | Asp | Ile |
| | | | 100 | | | | | 105 | | | | | 110 | | |
| Leu | Tyr | Arg | Ile | Arg | Phe | Tyr | Phe | Pro | His | Trp | Tyr | Cys | Ser | Gly | Ser |
| | | 115 | | | | | 120 | | | | | 125 | | | |
| Ser | Arg | Thr | Tyr | Arg | Tyr | Gly | Val | Ser | Arg | Gly | Ala | Glu | Ala | Pro | Leu |
| | 130 | | | | | 135 | | | | | 140 | | | | |
| Leu | Asp | Asp | Phe | Val | Met | Ser | Tyr | Leu | Phe | Val | Gln | Trp | Arg | His | Asp |
| 145 | | | | 150 | | | | | 155 | | | | | 160 | |
| Phe | Val | His | Gly | Trp | Ile | Lys | Val | Pro | Val | Thr | His | Glu | Thr | Gln | Glu |
| | | | | 165 | | | | | 170 | | | | | 175 | |
| Glu | Cys | Leu | Gly | Met | Ala | Val | Leu | Asp | Met | Met | Arg | Ile | Ala | Lys | Glu |
| | | | 180 | | | | | 185 | | | | | 190 | | |
| Lys | Asp | Gln | Thr | Pro | Leu | Ala | Val | Tyr | Asn | Ser | Val | Ser | Tyr | Lys | Thr |
| | | 195 | | | | | 200 | | | | | 205 | | | |
| Phe | Leu | Pro | Lys | Cys | Val | Arg | Ala | Lys | Ile | Gln | Asp | Tyr | His | Ile | Leu |
| | 210 | | | | | 215 | | | | | 220 | | | | |
| Thr | Arg | Lys | Arg | Ile | Arg | Tyr | Arg | Phe | Arg | Arg | Phe | Ile | Gln | Gln | Phe |
| 225 | | | | 230 | | | | | 235 | | | | | | 240 |
| Ser | Gln | Cys | Lys | Ala | Thr | Ala | Arg | Asn | Leu | Lys | Leu | Lys | Tyr | Leu | Ile |
| | | | | 245 | | | | | 250 | | | | | 255 | |
| Asn | Leu | Glu | Thr | Leu | Gln | Ser | Ala | Phe | Tyr | Thr | Glu | Gln | Phe | Glu | Val |
| | | | 260 | | | | | 265 | | | | | 270 | | |
| Lys | Glu | Ser | Ala | Arg | Gly | Pro | Ser | Gly | Glu | Glu | Ile | Phe | Ala | Thr | Ile |
| | | 275 | | | | | 280 | | | | | 285 | | | |
| Ile | Ile | Thr | Gly | Asn | Gly | Gly | Ile | Gln | Trp | Ser | Arg | Gly | Lys | His | Lys |
| | 290 | | | | | 295 | | | | | 300 | | | | |
| Glu | Ser | Glu | Thr | Leu | Thr | Glu | Gln | Asp | Val | Gln | Leu | Tyr | Cys | Asp | Phe |
| 305 | | | | 310 | | | | | 315 | | | | | | 320 |
| Pro | Asp | Ile | Ile | Asp | Val | Ser | Ile | Lys | Gln | Ala | Asn | Gln | Glu | Cys | Ser |
| | | | | 325 | | | | | 330 | | | | | 335 | |
| Asn | Glu | Ser | Arg | Ile | Val | Thr | Val | His | Lys | Gln | Asp | Gly | Lys | Val | Leu |
| | | | 340 | | | | | 345 | | | | | 350 | | |
| Glu | Ile | Glu | Leu | Ser | Ser | Leu | Lys | Glu | Ala | Leu | Ser | Phe | Val | Ser | Leu |
| | | 355 | | | | | 360 | | | | | 365 | | | |

-continued

| | | | | | | | | | | | | | |
|---|---|---|---|---|---|---|---|---|---|---|---|---|---|
| Ile | Asp | Gly | Tyr | Tyr | Arg | Leu | Thr | Ala | Asp | Ala | His | His | Tyr | Leu | Cys |
| | 370 | | | | 375 | | | | | 380 | | | | |
| Lys | Glu | Val | Ala | Pro | Pro | Ala | Val | Leu | Glu | Asn | Ile | His | Ser | Asn | Cys |
| 385 | | | | | 390 | | | | 395 | | | | | 400 |
| His | Gly | Pro | Ile | Ser | Met | Asp | Phe | Ala | Ile | Ser | Lys | Leu | Lys | Lys | Ala |
| | | | | 405 | | | | | 410 | | | | | 415 | |
| Gly | Asn | Gln | Thr | Gly | Leu | Tyr | Val | Leu | Arg | Cys | Ser | Pro | Lys | Asp | Phe |
| | | | 420 | | | | | 425 | | | | | 430 | | |
| Asn | Lys | Tyr | Phe | Leu | Thr | Phe | Ala | Val | Glu | Arg | Glu | Asn | Val | Ile | Glu |
| | | 435 | | | | | 440 | | | | | 445 | | | |
| Tyr | Lys | His | Cys | Leu | Ile | Thr | Lys | Asn | Glu | Asn | Gly | Glu | Tyr | Asn | Leu |
| | 450 | | | | | 455 | | | | | 460 | | | | |
| Ser | Gly | Thr | Asn | Arg | Asn | Phe | Ser | Asn | Leu | Lys | Asp | Leu | Leu | Asn | Cys |
| 465 | | | | | 470 | | | | | 475 | | | | | 480 |
| Tyr | Gln | Met | Glu | Thr | Val | Arg | Ser | Asp | Ser | Ile | Ile | Phe | Gln | Phe | Thr |
| | | | | 485 | | | | | 490 | | | | | 495 | |
| Lys | Cys | Cys | Pro | Pro | Lys | Pro | Lys | Asp | Lys | Ser | Asn | Leu | Leu | Val | Phe |
| | | | 500 | | | | 505 | | | | | 510 | | | |
| Arg | Thr | Asn | Gly | Ile | Ser | Asp | Val | Gln | Ile | Ser | Pro | Thr | Leu | Gln | Arg |
| | | | 515 | | | | 520 | | | | | 525 | | | |
| His | Asn | Asn | Val | Asn | Gln | Met | Val | Phe | His | Lys | Ile | Arg | Asn | Glu | Asp |
| | 530 | | | | | 535 | | | | | 540 | | | | |
| Leu | Ile | Phe | Asn | Glu | Ser | Leu | Gly | Gln | Gly | Thr | Phe | Thr | Lys | Ile | Phe |
| 545 | | | | | 550 | | | | | 555 | | | | | 560 |
| Lys | Gly | Val | Arg | Arg | Glu | Val | Gly | Asp | Tyr | Gly | Gln | Leu | His | Lys | Thr |
| | | | | 565 | | | | | 570 | | | | | 575 | |
| Glu | Val | Leu | Leu | Lys | Val | Leu | Asp | Lys | Ala | His | Arg | Asn | Tyr | Ser | Glu |
| | | | 580 | | | | | 585 | | | | | 590 | | |
| Ser | Phe | Phe | Glu | Ala | Ala | Ser | Met | Met | Ser | Gln | Leu | Ser | His | Lys | His |
| | | 595 | | | | | 600 | | | | | 605 | | | |
| Leu | Val | Leu | Asn | Tyr | Gly | Val | Cys | Val | Cys | Gly | Glu | Glu | Asn | Ile | Leu |
| | 610 | | | | | 615 | | | | | 620 | | | | |
| Val | Gln | Glu | Phe | Val | Lys | Phe | Gly | Ser | Leu | Asp | Thr | Tyr | Leu | Lys | Lys |
| 625 | | | | | 630 | | | | | 635 | | | | | 640 |
| Asn | Lys | Asn | Ser | Ile | Asn | Ile | Leu | Trp | Lys | Leu | Gly | Val | Ala | Lys | Gln |
| | | | | 645 | | | | | 650 | | | | | 655 | |
| Leu | Ala | Trp | Ala | Met | His | Phe | Leu | Glu | Glu | Lys | Ser | Leu | Ile | His | Gly |
| | | | 660 | | | | | 665 | | | | | 670 | | |
| Asn | Val | Cys | Ala | Lys | Asn | Ile | Leu | Leu | Ile | Arg | Glu | Glu | Asp | Arg | Arg |
| | | 675 | | | | | 680 | | | | | 685 | | | |
| Thr | Gly | Asn | Pro | Pro | Phe | Ile | Lys | Leu | Ser | Asp | Pro | Gly | Ile | Ser | Ile |
| | 690 | | | | | 695 | | | | | 700 | | | | |
| Thr | Val | Leu | Pro | Lys | Asp | Ile | Leu | Gln | Glu | Arg | Ile | Pro | Trp | Val | Pro |
| 705 | | | | | 710 | | | | | 715 | | | | | 720 |
| Pro | Glu | Cys | Ile | Glu | Asn | Pro | Lys | Asn | Leu | Asn | Leu | Ala | Thr | Asp | Lys |
| | | | | 725 | | | | | 730 | | | | | 735 | |
| Trp | Ser | Phe | Gly | Thr | Thr | Leu | Trp | Glu | Ile | Cys | Ser | Gly | Gly | Asp | Lys |
| | | | 740 | | | | | 745 | | | | | 750 | | |
| Pro | Leu | Ser | Ala | Leu | Asp | Ser | Gln | Arg | Lys | Leu | Gln | Phe | Tyr | Glu | Asp |
| | | 755 | | | | | 760 | | | | | 765 | | | |
| Lys | His | Gln | Leu | Pro | Ala | Pro | Lys | Trp | Thr | Glu | Leu | Ala | Asn | Leu | Ile |
| | 770 | | | | | 775 | | | | | 780 | | | | |
| Asn | Asn | Cys | Met | Asp | Tyr | Glu | Pro | Asp | Phe | Arg | Pro | Ala | Phe | Arg | Ala |
| 785 | | | | | 790 | | | | | 795 | | | | | 800 |

```
Val Ile Arg Asp Leu Asn Ser Leu Phe Thr Pro Asp Tyr Glu Leu Leu
                805                 810                 815

Thr Glu Asn Asp Met Leu Pro Asn Met Arg Ile Gly Ala Leu Gly Phe
            820                 825                 830

Ser Gly Ala Phe Glu Asp Arg Asp Pro Thr Gln Phe Glu Arg His
        835                 840                 845

Leu Lys Phe Leu Gln Gln Leu Gly Lys Gly Asn Phe Gly Ser Val Glu
    850                 855                 860

Met Cys Arg Tyr Asp Pro Leu Gln Asp Asn Thr Gly Glu Val Val Ala
865                 870                 875                 880

Val Lys Lys Leu Gln His Ser Thr Glu Glu His Leu Arg Asp Phe Glu
            885                 890                 895

Arg Glu Ile Glu Ile Leu Lys Ser Leu Gln His Asp Asn Ile Val Lys
        900                 905                 910

Tyr Lys Gly Val Cys Tyr Ser Ala Gly Arg Arg Asn Leu Arg Leu Ile
        915                 920                 925

Met Glu Tyr Leu Pro Tyr Gly Ser Leu Arg Asp Tyr Leu Gln Lys His
    930                 935                 940

Lys Glu Arg Ile Asp His Lys Lys Leu Leu Gln Tyr Thr Ser Gln Ile
945                 950                 955                 960

Cys Lys Gly Met Glu Tyr Leu Gly Thr Lys Arg Tyr Ile His Arg Asp
            965                 970                 975

Leu Ala Thr Arg Asn Ile Leu Val Glu Asn Glu Asn Arg Val Lys Ile
        980                 985                 990

Gly Asp Phe Gly Leu Thr Lys Val Leu Pro Gln Asp Lys Glu Tyr Tyr
    995                 1000                1005

Lys Val Lys Glu Pro Gly Glu Ser Pro Ile Phe Trp Tyr Ala Pro Gln
1010                1015                1020

Ser Leu Thr Glu Ser Lys Phe Ser Val Ala Ser Asp Val Trp Ser Phe
1025                1030                1035                1040

Gly Val Val Leu Tyr Glu Leu Phe Thr Tyr Ile Glu Lys Ser Lys Ser
            1045                1050                1055

Pro Pro Val Glu Phe Met Arg Met Ile Gly Asn Asp Lys Gln Gly Gln
        1060                1065                1070

Met Ile Val Phe His Leu Ile Glu Leu Leu Lys Ser Asn Gly Arg Leu
    1075                1080                1085

Pro Arg Pro Glu Gly Cys Pro Asp Glu Ile Tyr Val Ile Met Thr Glu
        1090                1095                1100

Cys Trp Asn Asn Asn Val Ser Gln Arg Pro Ser Phe Arg Asp Leu Ser
1105                1110                1115                1120

Phe Gly Trp Ile Lys Cys Gly Thr Val
                1125
```

( 2 ) INFORMATION FOR SEQ ID NO:7:

( i ) SEQUENCE CHARACTERISTICS:
( A ) LENGTH: 1154 amino acids
( B ) TYPE: amino acid
( C ) STRANDEDNESS: Not Relevant
( D ) TOPOLOGY: linear ( i i ) MOLECULE TYPE: protein ( x i ) SEQUENCE DESCRIPTION: SEQ ID NO:7:

```
Met Gln Tyr Leu Asn Ile Lys Glu Asp Cys Asn Ala Met Ala Phe Cys
1               5                   10                  15
```

```
Ala Lys Met Arg Ser Ser Lys Lys Thr Glu Val Asn Leu Glu Ala Pro
         20                  25                  30
Glu Pro Gly Val Glu Val Ile Phe Tyr Leu Ser Asp Arg Glu Pro Leu
             35              40              45
Arg Leu Gly Ser Gly Glu Tyr Thr Ala Glu Leu Cys Ile Arg Ala
         50              55              60
Ala Gln Ala Cys Arg Ile Ser Pro Leu Cys His Asn Leu Phe Ala Leu
65                   70              75                       80
Tyr Asp Glu Asn Thr Lys Leu Trp Tyr Ala Pro Asn Arg Thr Ile Thr
                 85              90                  95
Val Asp Asp Lys Met Ser Leu Arg Leu His Tyr Arg Met Arg Phe Tyr
             100             105             110
Phe Thr Asn Trp His Gly Thr Asn Asp Asn Glu Gln Ser Val Trp Arg
         115             120             125
His Ser Pro Lys Lys Gln Lys Asn Gly Tyr Glu Lys Lys Ile Pro
     130             135             140
Asp Ala Thr Pro Leu Leu Asp Ala Ser Ser Leu Glu Tyr Leu Phe Ala
145             150             155                       160
Gln Gly Gln Tyr Asp Leu Val Lys Cys Leu Ala Pro Ile Arg Asp Pro
             165             170             175
Lys Thr Glu Gln Asp Gly His Asp Ile Glu Asn Glu Cys Leu Gly Met
         180             185             190
Ala Val Leu Ala Ile Ser His Tyr Ala Met Met Lys Lys Met Gln Leu
         195             200             205
Pro Glu Leu Pro Lys Asp Ile Ser Tyr Lys Arg Tyr Ile Pro Glu Thr
     210             215             220
Leu Asn Lys Ser Ile Arg Gln Arg Asn Leu Leu Thr Arg Met Arg Ile
225             230             235                       240
Asn Asn Val Phe Lys Asp Phe Leu Lys Glu Phe Asn Asn Lys Thr Ile
             245             250             255
Cys Asp Ser Ser Val Ser Thr His Asp Leu Lys Val Lys Tyr Leu Ala
         260             265             270
Thr Leu Glu Thr Leu Thr Lys His Tyr Gly Ala Glu Ile Phe Glu Thr
         275             280             285
Ser Met Leu Leu Ile Ser Ser Glu Asn Glu Met Asn Trp Phe His Ser
     290             295             300
Asn Asp Gly Gly Asn Val Leu Tyr Tyr Glu Val Met Val Thr Gly Asn
305             310             315                       320
Leu Gly Ile Gln Trp Arg His Lys Pro Asn Val Val Ser Val Glu Lys
             325             330             335
Glu Lys Asn Lys Leu Lys Arg Lys Lys Leu Glu Asn Lys Asp Lys Lys
         340             345             350
Asp Glu Glu Lys Asn Lys Ile Arg Glu Glu Trp Asn Asn Phe Ser Phe
         355             360             365
Phe Pro Glu Ile Thr His Ile Val Ile Lys Glu Ser Val Val Ser Ile
     370             375             380
Asn Lys Gln Asp Asn Lys Lys Met Glu Leu Lys Leu Ser Ser His Glu
385             390             395                       400
Glu Ala Leu Ser Phe Val Ser Leu Val Asp Gly Tyr Phe Arg Leu Thr
             405             410             415
Ala Asp Ala His His Tyr Leu Cys Thr Asp Val Ala Pro Pro Leu Ile
         420             425             430
Val His Asn Ile Gln Asn Gly Cys His Gly Pro Ile Cys Thr Glu Tyr
         435             440             445
```

-continued

| | | | | | | | | | | | | | | |
|---|---|---|---|---|---|---|---|---|---|---|---|---|---|---|
| Ala | Ile | Asn | Lys | Leu | Arg | Gln | Glu | Gly | Ser | Glu | Gly | Met | Tyr | Val |
| | | | 450 | | | | 455 | | | | 460 | | | |
| Leu | Arg | Trp | Ser | Cys | Thr | Asp | Phe | Asp | Asn | Ile | Leu | Met | Thr | Val | Thr |
| 465 | | | | | 470 | | | | | 475 | | | | | 480 |
| Cys | Phe | Glu | Lys | Ser | Glu | Gln | Val | Gln | Gly | Ala | Gln | Lys | Gln | Phe | Lys |
| | | | | 485 | | | | | 490 | | | | | 495 | |
| Asn | Phe | Gln | Ile | Glu | Val | Gln | Lys | Gly | Arg | Tyr | Ser | Leu | His | Gly | Ser |
| | | | | 500 | | | | | 505 | | | | | 510 | |
| Asp | Arg | Ser | Phe | Pro | Ser | Leu | Gly | Asp | Leu | Met | Ser | His | Leu | Lys | Lys |
| | | 515 | | | | | 520 | | | | | 525 | | | |
| Gln | Ile | Leu | Arg | Thr | Asp | Asn | Ile | Ser | Phe | Met | Leu | Lys | Arg | Cys | Cys |
| | 530 | | | | | 535 | | | | | 540 | | | | |
| Gln | Pro | Lys | Pro | Arg | Glu | Ile | Ser | Asn | Leu | Leu | Val | Ala | Thr | Lys | Lys |
| 545 | | | | | 550 | | | | | 555 | | | | | 560 |
| Ala | Gln | Glu | Trp | Gln | Pro | Val | Tyr | Pro | Met | Ser | Gln | Leu | Ser | Phe | Asp |
| | | | | 565 | | | | | 570 | | | | | 575 | |
| Arg | Ile | Leu | Lys | Lys | Asp | Leu | Val | Gln | Gly | Glu | His | Leu | Gly | Arg | Gly |
| | | | 580 | | | | | 585 | | | | | 590 | | |
| Thr | Arg | Thr | His | Ile | Tyr | Ser | Gly | Thr | Leu | Met | Asp | Tyr | Lys | Asp | Asp |
| | | 595 | | | | | 600 | | | | | 605 | | | |
| Glu | Gly | Thr | Ser | Glu | Glu | Lys | Lys | Ile | Lys | Val | Ile | Leu | Lys | Val | Leu |
| | 610 | | | | | 615 | | | | | 620 | | | | |
| Asp | Pro | Ser | His | Arg | Asp | Ile | Ser | Leu | Ala | Phe | Phe | Glu | Ala | Ala | Ser |
| 625 | | | | | 630 | | | | | 635 | | | | | 640 |
| Met | Met | Arg | Gln | Val | Ser | His | Lys | His | Ile | Val | Tyr | Leu | Tyr | Gly | Val |
| | | | | 645 | | | | | 650 | | | | | 655 | |
| Cys | Val | Arg | Asp | Val | Glu | Asn | Ile | Met | Val | Glu | Glu | Phe | Val | Glu | Gly |
| | | | 660 | | | | | 665 | | | | | 670 | | |
| Gly | Pro | Leu | Asp | Leu | Phe | Met | His | Arg | Lys | Ser | Asp | Val | Leu | Thr | Thr |
| | | | 675 | | | | | 680 | | | | | 685 | | |
| Pro | Trp | Lys | Phe | Lys | Val | Ala | Lys | Gln | Leu | Ala | Ser | Ala | Leu | Ser | Tyr |
| | 690 | | | | | 695 | | | | | 700 | | | | |
| Leu | Glu | Asp | Lys | Asp | Leu | Val | His | Gly | Asn | Val | Cys | Thr | Lys | Asn | Leu |
| 705 | | | | | 710 | | | | | 715 | | | | | 720 |
| Leu | Leu | Ala | Arg | Glu | Gly | Ile | Asp | Ser | Glu | Cys | Gly | Pro | Phe | Ile | Lys |
| | | | | 725 | | | | | 730 | | | | | 735 | |
| Leu | Ser | Asp | Pro | Gly | Ile | Pro | Ile | Thr | Val | Leu | Ser | Arg | Gln | Glu | Cys |
| | | | 740 | | | | | 745 | | | | | 750 | | |
| Ile | Glu | Arg | Ile | Pro | Trp | Ile | Ala | Pro | Glu | Cys | Val | Glu | Asp | Ser | Lys |
| | | 755 | | | | | 760 | | | | | 765 | | | |
| Asn | Leu | Ser | Val | Ala | Ala | Asp | Lys | Trp | Ser | Phe | Gly | Thr | Thr | Leu | Trp |
| | 770 | | | | | 775 | | | | | 780 | | | | |
| Glu | Ile | Cys | Tyr | Asn | Gly | Glu | Ile | Pro | Leu | Lys | Asp | Lys | Thr | Leu | Ile |
| 785 | | | | | 790 | | | | | 795 | | | | | 800 |
| Glu | Lys | Glu | Arg | Phe | Tyr | Glu | Ser | Arg | Cys | Arg | Pro | Val | Thr | Pro | Ser |
| | | | | 805 | | | | | 810 | | | | | 815 | |
| Cys | Lys | Glu | Leu | Ala | Asp | Leu | Met | Thr | Arg | Cys | Met | Asn | Tyr | Asp | Pro |
| | | | 820 | | | | | 825 | | | | | 830 | | |
| Asn | Gln | Arg | Pro | Phe | Phe | Arg | Ala | Ile | Met | Arg | Asp | Ile | Asn | Lys | Leu |
| | | | 835 | | | | | 840 | | | | | 845 | | |
| Glu | Glu | Gln | Asn | Pro | Asp | Ile | Val | Ser | Arg | Lys | Lys | Asn | Gln | Pro | Thr |
| | | | | 850 | | | | | 855 | | | | | 860 | |
| Glu | Val | Asp | Pro | Thr | His | Phe | Glu | Lys | Arg | Phe | Leu | Lys | Arg | Ile | Arg |

-continued

|     |     | 865 |     |     |     | 870 |     |     |     | 875 |     |     |     | 880 |
| --- | --- | --- | --- | --- | --- | --- | --- | --- | --- | --- | --- | --- | --- | --- |

Asp Leu Gly Glu Gly His Phe Gly Lys Val Glu Leu Cys Arg Tyr Asp
            885                 890                 895

Pro Glu Asp Asn Thr Gly Glu Gln Val Ala Val Lys Ser Leu Lys Pro
            900                 905                 910

Glu Ser Gly Gly Asn His Ile Ala Asp Leu Lys Lys Glu Ile Glu Ile
            915                 920                 925

Leu Arg Asn Leu Tyr His Glu Asn Ile Val Lys Tyr Lys Gly Ile Cys
            930                 935                 940

Thr Glu Asp Gly Gly Asn Gly Ile Lys Leu Ile Met Glu Phe Leu Pro
945                 950                 955                 960

Ser Gly Ser Leu Lys Glu Tyr Leu Pro Lys Asn Lys Asn Lys Ile Asn
                    965                 970                 975

Leu Lys Gln Gln Leu Lys Tyr Ala Val Gln Ile Cys Lys Gly Met Asp
                    980                 985                 990

Tyr Leu Gly Ser Arg Gln Tyr Val His Arg Asp Leu Ala Ala Arg Asn
            995                 1000                1005

Val Leu Val Glu Ser Glu His Gln Val Lys Ile Gly Asp Phe Gly Leu
    1010                1015                1020

Thr Lys Ala Ile Glu Thr Asp Lys Glu Tyr Tyr Thr Val Lys Asp Asp
1025                1030                1035                1040

Arg Asp Ser Pro Val Phe Trp Tyr Ala Pro Glu Cys Leu Met Gln Ser
            1045                1050                1055

Lys Phe Tyr Ile Ala Ser Asp Val Trp Ser Phe Gly Val Thr Leu His
            1060                1065                1070

Glu Leu Leu Thr Tyr Cys Asp Ser Asp Ser Ser Pro Met Ala Leu Phe
            1075                1080                1085

Leu Lys Met Ile Gly Pro Thr His Gly Gln Met Thr Val Thr Arg Leu
    1090                1095                1100

Val Asn Thr Leu Lys Glu Gly Lys Arg Leu Pro Cys Pro Pro Asn Cys
1105                1110                1115                1120

Pro Asp Glu Val Tyr Gln Leu Met Arg Lys Cys Trp Glu Phe Gln Pro
            1125                1130                1135

Ser Asn Arg Thr Ser Phe Gln Asn Leu Ile Glu Gly Phe Glu Ala Leu
            1140                1145                1150

Leu Lys (2) INFORMATION FOR SEQ ID NO:8:

(i) SEQUENCE CHARACTERISTICS:
        (A) LENGTH: 1187 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:8:

Met Pro Leu Arg His Trp Gly Met Ala Arg Gly Ser Lys Pro Val Gly
1                   5                   10                  15

Asp Gly Ala Gln Pro Met Ala Ala Met Gly Gly Leu Lys Val Leu Leu
            20                  25                  30

His Trp Ala Gly Pro Gly Gly Gly Glu Pro Trp Val Thr Phe Ser Glu
        35                  40                  45

Ser Ser Leu Thr Ala Glu Glu Val Cys Ile His Ile Ala His Lys Val
    50                  55                  60

```
Gly Ile Thr Pro Pro Cys Phe Asn Leu Phe Ala Leu Phe Asp Ala Gln
 65                  70                  75                  80

Ala Gln Val Trp Leu Pro Pro Asn His Ile Leu Glu Ile Pro Arg Asp
                 85                  90                  95

Ala Ser Leu Met Leu Tyr Phe Arg Ile Arg Phe Tyr Phe Arg Asn Trp
            100                 105                 110

His Gly Met Asn Pro Arg Glu Pro Ala Val Tyr Arg Cys Gly Pro Pro
            115                 120                 125

Gly Thr Glu Ala Ser Ser Asp Gln Thr Ala Gln Gly Met Gln Leu Leu
        130                 135                 140

Asp Pro Ala Ser Phe Glu Tyr Leu Phe Glu Gln Gly Lys His Glu Phe
145                 150                 155                 160

Val Asn Asp Val Ala Ser Leu Trp Glu Leu Ser Thr Glu Glu Glu Ile
                165                 170                 175

His His Phe Lys Asn Glu Ser Leu Gly Met Ala Phe Leu His Leu Cys
            180                 185                 190

His Leu Ala Leu Arg His Gly Ile Pro Leu Glu Glu Val Ala Lys Lys
            195                 200                 205

Thr Ser Phe Lys Asp Cys Ile Pro Arg Ser Phe Arg Arg His Ile Arg
    210                 215                 220

Gln His Ser Ala Leu Thr Arg Leu Arg Leu Arg Asn Val Phe Arg Arg
225                 230                 235                 240

Phe Leu Arg Asp Phe Gln Pro Gly Arg Leu Ser Gln Gln Met Val Met
                245                 250                 255

Val Lys Tyr Leu Ala Thr Leu Glu Arg Leu Ala Pro Arg Phe Gly Thr
            260                 265                 270

Glu Arg Val Pro Val Cys His Leu Arg Leu Leu Ala Gln Ala Glu Gly
        275                 280                 285

Glu Pro Cys Tyr Ile Arg Asp Ser Gly Val Ala Pro Thr Asp Pro Gly
290                 295                 300

Pro Glu Ser Ala Ala Gly Pro Pro Thr His Glu Val Leu Val Thr Gly
305                 310                 315                 320

Thr Gly Gly Ile Gln Trp Trp Pro Val Glu Glu Val Asn Lys Glu
                325                 330                 335

Glu Gly Ser Ser Gly Ser Ser Gly Arg Asn Pro Gln Ala Ser Leu Phe
            340                 345                 350

Gly Lys Lys Ala Lys Ala His Lys Ala Phe Gly Gln Pro Ala Asp Arg
        355                 360                 365

Pro Arg Glu Pro Leu Trp Ala Tyr Phe Cys Asp Phe Arg Asp Ile Thr
370                 375                 380

His Val Val Leu Lys Glu His Cys Val Ser Ile His Arg Gln Asp Asn
385                 390                 395                 400

Lys Cys Leu Glu Leu Ser Leu Pro Ser Arg Ala Ala Ala Leu Ser Phe
            405                 410                 415

Val Ser Leu Val Asp Gly Tyr Phe Arg Leu Thr Ala Asp Ser Ser His
            420                 425                 430

Tyr Leu Cys His Glu Val Ala Pro Pro Arg Leu Val Met Ser Ile Arg
        435                 440                 445

Asp Gly Ile His Gly Pro Leu Leu Glu Pro Phe Val Gln Ala Lys Leu
        450                 455                 460

Arg Pro Glu Asp Gly Leu Tyr Leu Ile His Trp Ser Thr Ser His Pro
465                 470                 475                 480

Tyr Arg Leu Ile Leu Thr Val Ala Gln Arg Ser Gln Ala Pro Asp Gly
                485                 490                 495
```

| | | | | | | | | | | | | | |
|---|---|---|---|---|---|---|---|---|---|---|---|---|---|
|Met|Gln|Ser|Leu 500|Arg|Leu|Arg|Lys 505|Phe|Pro|Ile|Glu|Gln 510|Asp|Gly|
|Ala|Phe|Val 515|Leu|Glu|Gly|Trp|Gly 520|Arg|Ser|Phe|Pro|Ser 525|Val|Arg|Glu|
|Leu|Gly 530|Ala|Ala|Leu|Gln|Gly 535|Cys|Leu|Leu|Arg|Ala 540|Gly|Asp|Asp|Cys|
|Phe 545|Ser|Leu|Arg|Arg|Cys 550|Cys|Leu|Pro|Gln|Pro 555|Gly|Glu|Thr|Ser|Asn 560|
|Leu|Ile|Ile|Met|Arg 565|Gly|Ala|Arg|Ala|Ser 570|Pro|Arg|Thr|Leu|Asn 575|Leu|
|Ser|Gln|Leu|Ser 580|Phe|His|Arg|Val|Asp 585|Gln|Lys|Glu|Ile|Thr 590|Gln|Leu|
|Ser|His|Leu 595|Gly|Gln|Gly|Thr|Arg 600|Thr|Asn|Val|Tyr|Glu 605|Gly|Arg|Leu|
|Arg|Val 610|Glu|Gly|Ser|Gly|Asp 615|Pro|Glu|Glu|Gly|Lys 620|Met|Asp|Asp|Glu|
|Asp 625|Pro|Leu|Val|Pro|Gly 630|Arg|Asp|Arg|Gly|Gln 635|Glu|Leu|Arg|Val|Val 640|
|Leu|Lys|Val|Leu|Asp 645|Pro|Ser|His|His|Asp 650|Ile|Ala|Leu|Ala|Phe 655|Tyr|
|Glu|Thr|Ala|Ser 660|Leu|Met|Ser|Gln|Val 665|Ser|His|Thr|His|Leu 670|Ala|Phe|
|Val|His|Gly 675|Val|Cys|Val|Arg|Gly 680|Pro|Glu|Asn|Ser|Met 685|Val|Thr|Glu|
|Tyr|Val 690|Glu|His|Gly|Pro|Leu 695|Asp|Val|Trp|Leu|Arg 700|Arg|Glu|Arg|Gly|
|His 705|Val|Pro|Met|Ala|Trp 710|Lys|Met|Val|Val|Ala 715|Gln|Gln|Leu|Ala|Ser 720|
|Ala|Leu|Ser|Tyr|Leu 725|Glu|Asn|Lys|Asn|Leu 730|Val|His|Gly|Asn|Val 735|Cys|
|Gly|Arg|Asn|Ile 740|Leu|Leu|Ala|Arg|Leu 745|Gly|Leu|Ala|Glu|Gly 750|Thr|Ser|
|Pro|Phe|Ile 755|Lys|Leu|Ser|Asp|Pro 760|Gly|Val|Gly|Leu|Gly 765|Ala|Leu|Ser|
|Arg|Glu 770|Glu|Arg|Val|Glu|Arg 775|Ile|Pro|Trp|Leu|Ala 780|Pro|Glu|Cys|Leu|
|Pro 785|Gly|Gly|Ala|Asn|Ser 790|Leu|Ser|Thr|Ala|Met 795|Asp|Lys|Trp|Gly|Phe 800|
|Gly|Ala|Thr|Leu|Leu 805|Glu|Ile|Cys|Phe|Asp 810|Gly|Glu|Ala|Pro|Leu 815|Gln|
|Ser|Arg|Ser|Pro 820|Ser|Glu|Lys|Glu|His 825|Phe|Tyr|Gln|Arg|Gln 830|His|Arg|
|Leu|Pro|Glu 835|Pro|Ser|Cys|Pro|Gln 840|Leu|Ala|Thr|Leu|Thr 845|Ser|Gln|Cys|
|Leu|Thr 850|Tyr|Glu|Pro|Thr|Gln 855|Arg|Pro|Ser|Phe|Arg 860|Thr|Ile|Leu|Arg|
|Asp 865|Leu|Thr|Arg|Val|Gln 870|Pro|His|Asn|Leu|Ala 875|Asp|Val|Leu|Thr|Val 880|
|Asn|Arg|Asp|Ser|Pro 885|Ala|Val|Gly|Pro|Thr 890|Thr|Phe|His|Lys|Arg 895|Tyr|
|Leu|Lys|Lys|Ile 900|Arg|Asp|Leu|Gly|Glu 905|Gly|His|Phe|Gly|Lys 910|Val|Ser|
|Leu|Tyr|Cys|Tyr|Asp|Pro|Thr|Asn|Asp|Gly|Thr|Gly|Glu|Met|Val|Ala|

|  |  |  |  |  | 915 |  |  |  |  | 920 |  |  |  |  | 925 |  |  |
|---|---|---|---|---|---|---|---|---|---|---|---|---|---|---|---|---|---|
| Val | Lys | Ala | Leu | Lys | Ala | Asp | Cys | Gly | Pro | Gln | His | Arg | Ser | Gly | Trp |
| 930 |  |  |  |  | 935 |  |  |  |  | 940 |  |  |  |  |  |

```
                              915                       920                            925
    Val  Lys  Ala  Leu  Lys  Ala  Asp  Cys  Gly  Pro  Gln  His  Arg  Ser  Gly  Trp
    930                      935                      940

Lys  Gln  Glu  Ile  Asp  Ile  Leu  Arg  Thr  Leu  Tyr  His  Glu  His  Ile  Ile
    945                      950                      955                           960

Lys  Tyr  Lys  Gly  Cys  Cys  Glu  Asp  Gln  Gly  Glu  Lys  Ser  Leu  Gln  Leu
                             965                      970                      975

Val  Met  Glu  Tyr  Val  Pro  Leu  Gly  Ser  Leu  Arg  Asp  Tyr  Leu  Pro  Arg
                   980                      985                      990

His  Ser  Ile  Gly  Leu  Ala  Gln  Leu  Leu  Phe  Ala  Gln  Gln  Ile  Cys
              995                     1000                    1005

Glu  Gly  Met  Ala  Tyr  Leu  His  Ala  His  Asp  Tyr  Ile  His  Arg  Asp  Leu
              1010                    1015                    1020

Ala  Ala  Arg  Asn  Val  Leu  Leu  Asp  Asn  Asp  Arg  Leu  Val  Lys  Ile  Gly
    1025                    1030                    1035                         1040

Asp  Phe  Gly  Leu  Ala  Lys  Ala  Val  Pro  Glu  Gly  His  Glu  Tyr  Tyr  Arg
                        1045                    1050                         1055

Val  Arg  Glu  Asp  Gly  Asp  Ser  Pro  Val  Phe  Trp  Tyr  Ala  Pro  Glu  Cys
                   1060                    1065                    1070

Leu  Lys  Glu  Tyr  Lys  Phe  Tyr  Tyr  Ala  Ser  Asp  Val  Trp  Ser  Phe  Gly
              1075                    1080                    1085

Val  Thr  Leu  Tyr  Glu  Leu  Leu  Thr  His  Cys  Asp  Ser  Ser  Gln  Ser  Pro
              1090                    1095                    1100

Pro  Thr  Lys  Phe  Leu  Glu  Leu  Ile  Gly  Ile  Ala  Gln  Gly  Gln  Met  Thr
    1105                    1110                    1115                         1120

Val  Leu  Arg  Leu  Thr  Glu  Leu  Leu  Glu  Arg  Gly  Glu  Arg  Leu  Pro  Arg
                        1125                    1130                         1135

Pro  Asp  Lys  Cys  Pro  Cys  Glu  Val  Tyr  His  Leu  Met  Lys  Asn  Cys  Trp
                        1140                    1145                    1150

Glu  Thr  Glu  Ala  Ser  Phe  Arg  Pro  Thr  Phe  Glu  Asn  Leu  Ile  Pro  Ile
                        1155                    1160                    1165

Leu  Lys  Thr  Val  His  Glu  Lys  Tyr  Gln  Gly  Gln  Ala  Pro  Ser  Val  Phe
              1170                    1175                    1180

Ser  Val  Cys
    1185
```

( 2 ) INFORMATION FOR SEQ ID NO:9:

( i ) SEQUENCE CHARACTERISTICS:
        ( A ) LENGTH: 498 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:9:

```
    Met  Pro  Leu  Gly  Ala  Glu  Glu  Cys  Ala  Ala  Ile  Pro  His  Asn  Leu  Phe
    1                    5                       10                           15

Ala  Leu  Trp  Pro  Pro  Asn  Leu  Tyr  Arg  Ile  Arg  Phe  Tyr  Phe  Asn  Trp
                   20                      25                      30

Gly  Leu  Leu  Asp  Glu  Tyr  Leu  Phe  Gln  Asp  Val  Glu  Gln  Glu  Cys  Leu
              35                      40                      45

Gly  Met  Ala  Val  Leu  Ala  Glu  Ser  Tyr  Lys  Pro  Arg  Ile  Leu  Thr  Arg
              50                      55                      60

Arg  Ile  Arg  Phe  Phe  Leu  Phe  Leu  Lys  Lys  Tyr  Leu  Leu  Glu  Leu  Glu
    65                      70                      75                           80
```

-continued

| | | | | | | | | | | | | | | |
|---|---|---|---|---|---|---|---|---|---|---|---|---|---|---|
|Phe|Val|Val|Val|Thr 85|Gly|Gly|Gly|Ile|Gln 90|Trp|Glu|Phe|Cys 95|Asp|Phe|
|Pro|Ile|Ile|Lys 100|Val|Gln|Asp|Asn|Lys 105|Leu|Glu|Leu|Ser|Glu 110|Ala|Leu|
|Ser|Phe|Val 115|Ser|Leu|Val|Asp|Gly 120|Tyr|Phe|Arg|Leu|Thr 125|Ala|Asp|His|
|Tyr|Leu 130|Cys|Val|Ala|Pro|Pro 135|Ile|Cys|His|Gly|Pro 140|Ile|Phe|Ala|Ile|
|Lys 145|Leu|Gly|Tyr|Val|Leu 150|Arg|Trp|Ser|Asp|Phe 155|Leu|Thr|Val|Val|Lys 160|
|Ile|Gly|Leu|Gly|Arg 165|Phe|Ser|Leu|Arg|Phe 170|Cys|Cys|Pro|Pro|Ser 175|Asn|
|Leu|Leu|Val|Gln 180|Ser|Gln|Phe|His|Ile 185|Leu|Glu|Leu|Gly|Gly 190|Thr|Thr|
|Ile|Tyr|Gly 195|Asp|Val|Leu|Lys|Val 200|Leu|Asp|His|Phe|Glu 205|Ala|Ala|Ser|
|Met|Ser 210|Gln|Val|Ser|His|His 215|Leu|Val|Gly|Val|Cys 220|Val|Glu|Asn|Val|
|Glu 225|Phe|Val|Gly|Leu|Asp 230|Arg|Trp|Lys|Val|Ala 235|Lys|Gln|Leu|Ala|Ala 240|
|Leu|Tyr|Leu|Glu|Asp 245|Leu|Leu|His|Gly|Asn 250|Val|Cys|Asn|Ile|Leu 255|Leu|
|Ala|Arg|Glu|Gly 260|Pro|Phe|Ile|Lys|Leu 265|Ser|Asp|Pro|Gly|Val 270|Leu|Ser|
|Glu|Arg|Ile 275|Pro|Trp|Ala|Pro|Glu 280|Cys|Asn|Leu|Ser|Ala 285|Asp|Lys|Trp|
|Phe|Gly 290|Thr|Leu|Trp|Glu|Cys 295|Gly|Pro|Leu|Lys|Phe 300|Tyr|Glu|Leu|Pro|
|Glu 305|Leu|Ala|Leu|Cys|Met 310|Tyr|Glu|Pro|Gln|Arg 315|Pro|Phe|Arg|Ala|Arg 320|
|Asp|Leu|Asn|Leu|Pro 325|Asp|Pro|Thr|Phe|Glu 330|Arg|Leu|Lys|Ile|Leu 335|Gly|
|Gly|Phe|Gly|Val 340|Glu|Leu|Cys|Arg|Tyr 345|Asp|Pro|Asp|Asn|Thr 350|Gly|Glu|
|Val|Ala|Val 355|Lys|Leu|Ser|Gly|His 360|Asp|Glu|Ile|Ile|Leu 365|Leu|His|Ile|
|Val|Lys 370|Tyr|Lys|Gly|Cys|Gly 375|Leu|Met|Glu|Tyr|Leu 380|Pro|Gly|Ser|Leu|
|Arg 385|Asp|Tyr|Leu|Ile|Leu 390|Leu|Leu|Tyr|Leu|Leu 395|Gln|Ile|Cys|Lys|Gly 400|
|Met|Tyr|Leu|Gly|Tyr 405|His|Arg|Asp|Leu|Ala 410|Ala|Arg|Asn|Leu|Val 415|Glu|
|Glu|Val|Lys|Ile 420|Gly|Asp|Phe|Gly|Leu 425|Lys|Pro|Asp|Lys|Glu 430|Tyr|Tyr|
|Val|Glu|Gly 435|Ser|Pro|Phe|Trp|Tyr 440|Ala|Pro|Glu|Leu|Leu 445|Phe|Ala|Ser|
|Asp|Val 450|Trp|Ser|Phe|Gly|Val 455|Leu|Tyr|Glu|Leu|Thr 460|Tyr|Cys|Asp|Ser|
|Ser 465|Pro|Phe|Leu|Met|Ile 470|Gly|Gly|Gln|Met|Val 475|Arg|Leu|Glu|Leu|Leu 480|
|Gly|Arg|Leu|Pro|Pro 485|Cys|Pro|Glu|Val|Tyr 490|Leu|Met|Cys|Trp|Ser 495|Arg|
|Phe|Leu| | | | | | | | | | | | | | |

( 2 ) INFORMATION FOR SEQ ID NO:10:

( i ) SEQUENCE CHARACTERISTICS:
        ( A ) LENGTH: 1082 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:10:

```
Met Ala Pro Pro Ser Glu Glu Thr Pro Leu Ile Pro Gln Arg Ser Cys
 1               5                  10                  15

Ser Leu Leu Ser Thr Glu Ala Gly Ala Leu His Val Leu Leu Pro Ala
            20                  25                  30

Arg Gly Pro Gly Pro Pro Gln Arg Leu Ser Phe Ser Phe Gly Asp His
            35                  40                  45

Leu Ala Glu Asp Leu Cys Val Gln Ala Ala Lys Ala Ser Ala Ile Leu
50                      55                  60

Pro Val Tyr His Ser Leu Phe Ala Leu Ala Thr Glu Asp Leu Ser Cys
65                      70                  75                  80

Trp Phe Pro Arg Ala Thr Ser Ser Pro Trp Arg Met Pro Ala Pro Gln
                    85                  90                  95

Val Leu Leu Tyr Arg Ile Arg Phe Tyr Phe Pro Asn Trp Phe Gly Leu
                100                 105                 110

Glu Lys Cys His Arg Phe Gly Leu Arg Lys Asp Leu Ala Ser Ala Ile
            115                 120                 125

Leu Asp Leu Pro Val Leu Glu His Leu Phe Ala Gln His Arg Ser Asp
130                 135                 140

Leu Val Ser Gly Arg Leu Pro Arg Gly Leu Ser Leu Lys Glu Gln Gly
145                 150                 155                 160

Glu Cys Leu Ser Leu Ala Val Leu Asp Leu Ala Arg Met Ala Arg Glu
                165                 170                 175

Gln Ala Gln Arg Arg Gly Glu Leu Leu Lys Thr Val Ser Tyr Lys Ala
            180                 185                 190

Cys Leu Pro Pro Ser Leu Arg Asp Leu Ile Gln Gly Leu Ser Phe Val
            195                 200                 205

Thr Gly Arg Arg Ile Arg Arg Thr Val Glu Ser Pro Leu Arg Arg Val
210                 215                 220

Ala Ala Cys Gln Ala Asp Arg His Ser Leu Met Ala Lys Tyr Ile Met
225                 230                 235                 240

Asp Leu Glu Arg Leu Asp Pro Ala Gly Ala Ala Glu Thr Phe His Val
                245                 250                 255

Gly Leu Pro Gly Ala Leu Gly Gly His Asp Gly Leu Gly Leu Val Arg
            260                 265                 270

Val Ala Gly Asp Gly Gly Ile Ala Trp Thr Gln Gly Glu Gln Glu Val
            275                 280                 285

Leu Gln Pro Phe Cys Asp Phe Pro Glu Ile Val Asp Ile Ser Ile Lys
290                 295                 300

Gln Ala Pro Arg Val Gly Pro Ala Gly Glu His Arg Leu Val Thr Val
305                 310                 315                 320

Thr Arg Thr Asp Asn Gln Ile Leu Glu Ala Glu Phe Pro Gly Leu Pro
                325                 330                 335

Glu Ala Leu Ser Phe Val Ala Leu Val Asp Gly Tyr Phe Arg Leu Thr
            340                 345                 350
```

-continued

| | | | | | | | | | | | | | |
|---|---|---|---|---|---|---|---|---|---|---|---|---|---|
| Thr | Asp | Ser 355 | Gln | His | Phe | Phe | Cys 360 | Lys | Glu | Val | Asp | Pro 365 | Arg | Leu | Leu |
| Glu | Glu 370 | Val | Ala | Glu | Gln | Cys 375 | His | Gly | Pro | Ile | Thr 380 | Leu | Asp | Phe | Ala |
| Ile 385 | Asn | Lys | Leu | Lys | Thr 390 | Gly | Gly | Ser | Arg | Pro 395 | Gly | Ser | Tyr | Val | Leu 400 |
| Arg | Arg | Ile | Pro | Gln 405 | Asp | Phe | Asp | Ser | Phe 410 | Leu | Leu | Thr | Val | Cys 415 | Val |
| Gln | Asn | Pro | Leu 420 | Gly | Pro | Asp | Tyr | Lys 425 | Gly | Cys | Leu | Ile | Arg 430 | Arg | Ser |
| Pro | Thr | Gly 435 | Thr | Phe | Leu | Leu | Val 440 | Gly | Leu | Ser | Arg | Pro 445 | His | Ser | Ser |
| Leu | Arg 450 | Glu | Leu | Leu | Ala | Thr 455 | Cys | Trp | Asp | Gly | Gly 460 | Leu | His | Val | Asp |
| Gly 465 | Val | Ala | Val | Thr | Leu 470 | Thr | Ser | Cys | Cys | Ile 475 | Pro | Arg | Pro | Lys | Glu 480 |
| Lys | Ser | Asn | Leu | Ile 485 | Val | Val | Gln | Arg | Gly 490 | His | Ser | Pro | Pro | Thr 495 | Ser |
| Ser | Leu | Val | Gln 500 | Pro | Gln | Ser | Gln | Tyr 505 | Gln | Leu | Ser | Gln | Met 510 | Thr | Phe |
| His | Lys | Ile 515 | Pro | Ala | Asp | Ser | Leu 520 | Glu | Trp | His | Glu | Asn 525 | Leu | Gly | His |
| Gly | Ser 530 | Phe | Thr | Lys | Ile | Tyr 535 | Arg | Gly | Cys | Arg | His 540 | Glu | Val | Val | Asp |
| Gly 545 | Glu | Ala | Arg | Lys | Thr 550 | Glu | Val | Leu | Leu | Lys 555 | Val | Met | Asp | Ala | Lys 560 |
| His | Lys | Asn | Cys | Met 565 | Glu | Ser | Phe | Leu | Glu 570 | Ala | Ala | Ser | Leu | Met 575 | Ser |
| Gln | Val | Ser | Tyr 580 | Arg | His | Leu | Val | Leu 585 | Leu | His | Gly | Val | Cys 590 | Met | Ala |
| Gly | Asp | Ser 595 | Thr | Met | Val | Glu | Glu 600 | Phe | Val | His | Leu | Gly 605 | Ala | Ile | Asp |
| Met | Tyr 610 | Leu | Arg | Lys | Arg | Gly 615 | His | Leu | Val | Pro | Ala 620 | Ser | Trp | Lys | Leu |
| Gln 625 | Val | Val | Lys | Gln | Leu 630 | Ala | Tyr | Ala | Leu | Asn 635 | Tyr | Leu | Glu | Asp | Lys 640 |
| Gly | Leu | Ser | His | Gly 645 | Asn | Val | Ser | Ala | Arg 650 | Lys | Val | Leu | Leu | Ala 655 | Arg |
| Glu | Gly 660 | Ala | Asp | Gly | Ser | Pro | Pro | Phe 665 | Ile | Lys | Leu | Ser | Asp 670 | Pro | Gly |
| Val | Ser | Pro 675 | Ala | Val | Leu | Ser | Leu 680 | Glu | Met | Leu | Thr | Asp 685 | Arg | Ile | Pro |
| Trp | Val 690 | Ala | Pro | Glu | Cys | Leu 695 | Arg | Glu | Ala | Gln | Thr 700 | Leu | Ser | Leu | Glu |
| Ala 705 | Asp | Lys | Trp | Gly | Phe 710 | Gly | Ala | Thr | Val | Trp 715 | Glu | Val | Phe | Ser | Gly 720 |
| Val | Thr | Met | Pro | Ile 725 | Ser | Ala | Leu | Asp | Pro 730 | Ala | Lys | Lys | Leu | Gln 735 | Phe |
| Tyr | Glu | Asp | Arg 740 | Gln | Gln | Leu | Ser | Ala 745 | Pro | Lys | Trp | Thr | Glu 750 | Leu | Ala |
| Leu | Leu | Ile 755 | Gln | Gln | Cys | Met | Ala 760 | Tyr | Glu | Pro | Val | Gln 765 | Arg | Pro | Ser |
| Leu | Arg 770 | Ala | Val | Ile | Arg | Asp 775 | Leu | Asn | Ser | Leu | Ile 780 | Ser | Ser | Asp | Tyr |

| Glu 785 | Leu | Leu | Ser | Asp | His 790 | Thr | Trp | Cys | Pro | Gly 795 | Thr | Arg | Asp | Gly | Leu 800 |

| Trp | Asn | Gly | Ala | Gln 805 | Leu | Tyr | Ala | Cys | Gln 810 | Asp | Pro | Thr | Ile | Phe 815 | Glu |

| Glu | Arg | His | Leu 820 | Lys | Tyr | Ile | Ser | Gln 825 | Leu | Gly | Lys | Gly | Phe 830 | Phe | Gly |

| Ser | Val | Glu 835 | Leu | Cys | Arg | Tyr | Asp 840 | Pro | Leu | Gly | Asp | Asn 845 | Thr | Gly | Ala |

| Leu | Val 850 | Ala | Val | Lys | Gln 855 | Leu | Gln | His | Ser | Gly 860 | Pro | Asp | Gln | Gln | Arg |

| Asp 865 | Phe | Gln | Arg | Glu | Ile 870 | Gln | Ile | Leu | Lys | Ala 875 | Gln | His | Ser | Asp | Phe 880 |

| Ile | Val | Lys | Tyr | Arg 885 | Gly | Val | Ser | Tyr | Gly 890 | Pro | Gly | Arg | Gln | Ser 895 | Pro |

| Ala | Leu | Val | Met 900 | Glu | Tyr | Leu | Pro | Ser 905 | Gly | Cys | Leu | Arg | Asp 910 | Phe | Leu |

| Gln | Arg | His 915 | Arg | Gly | Leu | Asp | Ala 920 | Ser | Arg | Leu | Leu | Leu 925 | Tyr | Ser | Ser |

| Gln | Ile | Cys 930 | Lys | Gly | Met | Glu 935 | Tyr | Leu | Gly | Ser | Arg 940 | Arg | Cys | Val | His |

| Arg 945 | Asp | Leu | Ala | Ala | Arg 950 | Asn | Ile | Leu | Val | Glu 955 | Ser | Glu | Ala | His | Val 960 |

| Lys | Ile | Ala | Asp | Phe 965 | Gly | Leu | Ala | Lys | Leu 970 | Leu | Pro | Leu | Asp | Lys 975 | Asp |

| Tyr | Tyr | Val | Val 980 | Arg | Glu | Pro | Gly | Gln 985 | Ser | Pro | Ile | Phe | Trp 990 | Tyr | Ala |

| Pro | Glu | Ser 995 | Leu | Ser | Asp | Asn | Ile 1000 | Phe | Ser | Arg | Gln | Ser 1005 | Asp | Val | Trp |

| Ser | Phe 1010 | Gly | Val | Val | Leu | Tyr 1015 | Glu | Leu | Phe | Thr | Tyr 1020 | Cys | Asp | Lys | Ser |

| Cys 1025 | Ser | Pro | Ser | Ala | Glu 1030 | Phe | Leu | Arg | Met | Met 1035 | Gly | Cys | Glu | Arg | Asp 1040 |

| Val | Pro | Arg | Leu | Cys 1045 | Arg | Leu | Leu | Glu | Leu 1050 | Leu | Glu | Glu | Gly | Gln 1055 | Arg |

| Leu | Pro | Ala | Pro 1060 | Pro | Cys | Cys | Pro | Ala 1065 | Glu | Val | Ser | Cys | Tyr 1070 | Ser | Gly |

| Trp | Arg | Asp 1075 | Asp | Ile | Cys | Leu | Pro 1080 | Ala | Glu |

( 2 ) INFORMATION FOR SEQ ID NO:11:

( i ) SEQUENCE CHARACTERISTICS:
( A ) LENGTH: 1100 amino acids
( B ) TYPE: amino acid
( C ) STRANDEDNESS: Not Relevant
( D ) TOPOLOGY: linear ( i i ) MOLECULE TYPE: protein ( x i ) SEQUENCE DESCRIPTION: SEQ ID NO:11:

| Met 1 | Ala | Pro | Pro | Ser 5 | Glu | Glu | Thr | Pro | Leu 10 | Ile | Ser | Gln | Arg | Ser 15 | Cys |

| Ser | Leu | Ser | Ser 20 | Ser | Glu | Ala | Gly | Ala 25 | Leu | His | Val | Leu | Leu 30 | Pro | Pro |

| Arg | Gly | Pro 35 | Gly | Pro | Pro | Gln | Arg 40 | Leu | Ser | Phe | Ser | Phe 45 | Gly | Asp | Tyr |

-continued

| | | | | | | | | | | | | | | | |
|---|---|---|---|---|---|---|---|---|---|---|---|---|---|---|---|
| Leu | Ala | Glu | Asp | Leu | Cys | Val | Arg | Ala | Ala | Lys | Ala | Cys | Gly | Ile | Leu |
| | 50 | | | | 55 | | | | 60 | | | | | | |
| Pro | Val | Tyr | His | Ser | Leu | Phe | Ala | Leu | Ala | Thr | Glu | Asp | Leu | Ser | Cys |
| 65 | | | | 70 | | | | 75 | | | | | | | 80 |
| Trp | Phe | Pro | Pro | Ser | His | Ile | Phe | Ser | Ile | Glu | Asp | Val | Asp | Thr | Gln |
| | | | | 85 | | | | 90 | | | | | 95 | | |
| Val | Leu | Val | Tyr | Arg | Leu | Arg | Phe | Tyr | Phe | Pro | Gly | Trp | Phe | Gly | Leu |
| | | | 100 | | | | | 105 | | | | | 110 | | |
| Glu | Thr | Cys | His | Arg | Phe | Gly | Leu | His | Lys | Asp | Leu | Thr | Ser | Ala | Ile |
| | | 115 | | | | | 120 | | | | | 125 | | | |
| Leu | Asp | Val | His | Val | Leu | Glu | His | Leu | Phe | Ala | Gln | His | Arg | Ser | Asp |
| | 130 | | | | | 135 | | | | | 140 | | | | |
| Leu | Val | Ser | Gly | Arg | Leu | Pro | Val | Gly | Leu | Ser | Leu | Lys | Asp | Gln | Gly |
| 145 | | | | | 150 | | | | | 155 | | | | | 160 |
| Glu | Phe | Leu | Ser | Leu | Ala | Val | Leu | Asp | Leu | Ala | Gln | Met | Ala | Arg | Lys |
| | | | | 165 | | | | | 170 | | | | | 175 | |
| Gln | Ala | Gln | Arg | Pro | Gly | Glu | Leu | Leu | Lys | Ser | Val | Ser | Tyr | Lys | Ala |
| | | | 180 | | | | | 185 | | | | | 190 | | |
| Cys | Leu | Pro | Pro | Ser | Leu | Arg | Asp | Leu | Ile | Gln | Gly | Gln | Ser | Phe | Val |
| | | 195 | | | | | 200 | | | | | 205 | | | |
| Thr | Arg | Arg | Arg | Ile | Arg | Arg | Thr | Val | Val | Gln | Ala | Leu | Ala | Pro | Cys |
| | 210 | | | | | 215 | | | | | 220 | | | | |
| Ser | Ser | Leu | Pro | Ser | Arg | Pro | Tyr | Ala | Leu | Met | Ala | Lys | Tyr | Ile | Leu |
| 225 | | | | | 230 | | | | | 235 | | | | | 240 |
| Asp | Leu | Glu | Arg | Leu | His | Pro | Ala | Ala | Thr | Thr | Glu | Ser | Phe | Leu | Val |
| | | | | 245 | | | | | 250 | | | | | 255 | |
| Gly | Leu | Pro | Gly | Ala | Gln | Glu | Glu | Pro | Gly | Cys | Leu | Arg | Val | Thr | Gly |
| | | | 260 | | | | | 265 | | | | | 270 | | |
| Asp | Asn | Gly | Ile | Ala | Trp | Ser | Ser | Lys | Asp | Gln | Glu | Leu | Phe | Gln | Thr |
| | | 275 | | | | | 280 | | | | | 285 | | | |
| Phe | Cys | Asp | Phe | Pro | Glu | Ile | Val | Asp | Val | Ser | Ile | Lys | Gln | Ala | Pro |
| | 290 | | | | | 295 | | | | | 300 | | | | |
| Arg | Val | Gly | Pro | Ala | Gly | Glu | His | Arg | Leu | Val | Thr | Ile | Thr | Arg | Met |
| 305 | | | | | 310 | | | | | 315 | | | | | 320 |
| Asp | Gly | His | Ile | Leu | Glu | Ala | Glu | Phe | Pro | Gly | Leu | Pro | Glu | Ala | Leu |
| | | | | 325 | | | | | 330 | | | | | 335 | |
| Ser | Phe | Val | Ala | Leu | Val | Asp | Gly | Tyr | Phe | Arg | Leu | Ile | Cys | Asp | Ser |
| | | | 340 | | | | | 345 | | | | | 350 | | |
| Arg | His | Phe | Phe | Cys | Lys | Glu | Val | Ala | Pro | Pro | Arg | Leu | Leu | Glu | Glu |
| | | 355 | | | | | 360 | | | | | 365 | | | |
| Glu | Ala | Glu | Leu | Cys | His | Gly | Pro | Ile | Thr | Leu | Asp | Phe | Ala | Ile | His |
| | 370 | | | | | 375 | | | | | 380 | | | | |
| Lys | Leu | Lys | Ala | Ala | Gly | Ser | Leu | Pro | Gly | Ser | Tyr | Ile | Leu | Arg | Arg |
| 385 | | | | | 390 | | | | | 395 | | | | | 400 |
| Ser | Pro | Gln | Asp | Tyr | Asp | Ser | Phe | Leu | Leu | Thr | Ala | Cys | Val | Gln | Thr |
| | | | | 405 | | | | | 410 | | | | | 415 | |
| Pro | Leu | Gly | Pro | Asp | Tyr | Lys | Gly | Cys | Leu | Ile | Arg | Gln | Asp | Pro | Ser |
| | | | 420 | | | | | 425 | | | | | 430 | | |
| Gly | Ala | Phe | Ser | Leu | Val | Gly | Leu | Ser | Gln | Leu | His | Arg | Ser | Leu | Gln |
| | | | 435 | | | | | 440 | | | | | 445 | | |
| Glu | Leu | Leu | Thr | Ala | Cys | Trp | His | Ser | Gly | Leu | Gln | Val | Asp | Gly | Thr |
| | 450 | | | | | 455 | | | | | 460 | | | | |
| Ala | Leu | Asn | Leu | Thr | Ser | Cys | Cys | Val | Pro | Arg | Pro | Lys | Glu | Lys | Ser |
| 465 | | | | | 470 | | | | | 475 | | | | | 480 |

```
Asn  Leu  Ile  Val  Val  Arg  Arg  Gly  Arg  Asn  Pro  Thr  Pro  Ala  Pro  Gly
               485                      490                     495

His  Ser  Pro  Ser  Cys  Cys  Ala  Leu  Thr  Lys  Leu  Ser  Phe  His  Thr  Ile
               500                      505                     510

Pro  Ala  Asp  Ser  Leu  Glu  Trp  His  Glu  Asn  Leu  Gly  His  Gly  Ser  Phe
               515                      520                     525

Thr  Lys  Ile  Phe  His  Gly  His  Arg  Arg  Glu  Val  Val  Asp  Gly  Glu  Thr
     530                     535                          540

His  Asp  Thr  Glu  Val  Leu  Leu  Lys  Val  Met  Asp  Ser  Arg  His  Gln  Asn
545                      550                     555                          560

Cys  Met  Glu  Ser  Phe  Leu  Glu  Ala  Ala  Ser  Leu  Met  Ser  Gln  Val  Ser
               565                      570                     575

Tyr  Pro  His  Leu  Val  Leu  Leu  His  Gly  Val  Cys  Met  Ala  Gly  Asp  Ser
               580                      585                     590

Ile  Met  Val  Gln  Glu  Phe  Val  Tyr  Leu  Gly  Ala  Ile  Asp  Thr  Tyr  Leu
               595                      600                     605

Arg  Lys  Arg  Gly  His  Leu  Val  Pro  Ala  Ser  Trp  Lys  Leu  Gln  Val  Thr
     610                     615                          620

Lys  Gln  Leu  Ala  Tyr  Ala  Leu  Asn  Tyr  Leu  Glu  Asp  Lys  Gly  Leu  Pro
625                      630                     635                          640

His  Gly  Asn  Val  Ser  Ala  Arg  Lys  Val  Leu  Leu  Ala  Arg  Glu  Gly  Val
               645                      650                     655

Asp  Gly  Asn  Pro  Pro  Phe  Ile  Lys  Leu  Ser  Asp  Pro  Gly  Val  Ser  Pro
               660                      665                     670

Thr  Val  Leu  Ser  Leu  Glu  Met  Leu  Thr  Asp  Arg  Ile  Pro  Trp  Val  Ala
               675                      680                     685

Pro  Glu  Cys  Leu  Gln  Glu  Ala  Gly  Thr  Leu  Asn  Leu  Glu  Ala  Asp  Lys
     690                     695                          700

Trp  Gly  Phe  Gly  Ala  Thr  Thr  Trp  Glu  Val  Phe  Ser  Gly  Ala  Pro  Met
705                      710                     715                          720

His  Ile  Thr  Ser  Leu  Glu  Pro  Ala  Lys  Lys  Leu  Lys  Phe  Tyr  Glu  Asp
               725                      730                     735

Arg  Gly  Gln  Leu  Pro  Ala  Leu  Lys  Trp  Thr  Glu  Leu  Glu  Gly  Leu  Ile
               740                      745                     750

Ala  Gln  Cys  Met  Ala  Tyr  Asp  Pro  Gly  Arg  Arg  Pro  Ser  Phe  Arg  Ala
               755                      760                     765

Ile  Leu  Arg  Asp  Leu  Asn  Gly  Leu  Ile  Thr  Ser  Asp  Tyr  Glu  Leu  Leu
     770                     775                          780

Ser  Asp  Pro  Thr  Pro  Gly  Ile  Pro  Asn  Pro  Arg  Asp  Glu  Leu  Cys  Gly
785                      790                     795                          800

Gly  Ala  Gln  Leu  Tyr  Ala  Cys  Gln  Asp  Pro  Ala  Ile  Phe  Glu  Glu  Arg
               805                      810                     815

His  Leu  Lys  Tyr  Ile  Ser  Leu  Leu  Gly  Lys  Gly  Asn  Phe  Gly  Ser  Val
               820                      825                     830

Glu  Leu  Cys  Arg  Tyr  Asp  Pro  Leu  Gly  Asp  Asn  Thr  Gly  Pro  Leu  Val
               835                      840                     845

Ala  Val  Lys  Gln  Leu  Gln  His  Ser  Gly  Pro  Glu  Gln  Gln  Arg  Asp  Phe
850                      855                     860

Gln  Arg  Glu  Ile  Gln  Ile  Leu  Lys  Ala  Leu  His  Cys  Asp  Phe  Ile  Val
865                      870                     875                          880

Lys  Tyr  Arg  Gly  Val  Ser  Tyr  Gly  Pro  Gly  Arg  Gln  Glu  Leu  Arg  Leu
               885                      890                     895

Val  Met  Glu  Tyr  Leu  Pro  Ser  Gly  Cys  Leu  Arg  Asp  Phe  Leu  Gln  Arg
```

His Arg Ala Arg Leu His Asn Asp Arg Leu Leu Leu Phe Ala Trp Gln
       915                 920                 925

Ile Cys Lys Gly Met Glu Tyr Leu Gly Ala Arg Arg Cys Val His Arg
    930                 935                 940

Asp Leu Ala Ala Arg Asn Ile Leu Val Glu Ser Glu Ala His Val Lys
945                 950                 955                 960

Ile Ala Asp Phe Gly Leu Ala Lys Leu Leu Pro Leu Gly Lys Asp Tyr
            965                 970                 975

Tyr Val Val Arg Val Pro Gly Gln Ser Pro Ile Phe Trp Tyr Ala Pro
        980                 985                 990

Glu Ser Leu Ser Asp Asn Ile Phe Ser Arg Gln Ser Asp Val Trp Ser
        995                 1000                1005

Phe Gly Val Val Leu Tyr Glu Leu Phe Thr Tyr Ser Asp Lys Ser Cys
    1010                1015                1020

Ser Pro Ser Thr Glu Phe Leu Arg Met Ile Gly Pro Glu Arg Glu Gly
1025                1030                1035                1040

Ser Pro Leu Cys His Leu Leu Glu Leu Leu Ala Glu Gly Arg Arg Leu
            1045                1050                1055

Pro Pro Pro Ser Thr Cys Pro Thr Glu Val Gln Glu Leu Met Gln Leu
            1060                1065                1070

Cys Trp Ser Pro Asn Pro Gln Asp Arg Pro Ala Phe Asp Thr Leu Ser
        1075                1080                1085

Pro Gln Leu Asp Ala Leu Trp Arg Gly Ser Pro Gly
    1090                1095                1100

(2) INFORMATION FOR SEQ ID NO:12:

(i) SEQUENCE CHARACTERISTICS:
     (A) LENGTH: 846 amino acids
     (B) TYPE: amino acid
     (C) STRANDEDNESS: Not Relevant
     (D) TOPOLOGY: linear (ii) MOLECULE TYPE: protein (xi) SEQUENCE DESCRIPTION: SEQ ID NO:12:

Met Ala Pro Pro Ser Glu Glu Thr Pro Leu Ile Gln Arg Ser Cys Ser
1               5                   10                  15

Leu Ser Glu Ala Gly Ala Leu His Val Leu Leu Pro Arg Gly Pro Gly
            20                  25                  30

Pro Pro Gln Arg Leu Ser Phe Ser Phe Gly Asp Leu Ala Glu Asp Leu
        35                  40                  45

Cys Val Ala Ala Lys Ala Ile Leu Pro Val Tyr His Ser Leu Phe Ala
    50                  55                  60

Leu Ala Thr Glu Asp Leu Ser Cys Trp Phe Pro Gln Val Leu Tyr Arg
65                  70                  75                  80

Arg Phe Tyr Phe Pro Trp Phe Gly Leu Glu Cys His Arg Phe Gly Leu
                85                  90                  95

Lys Asp Leu Ser Ala Ile Leu Asp Val Leu Glu His Leu Phe Ala Gln
            100                 105                 110

His Arg Ser Asp Leu Val Ser Gly Arg Leu Pro Gly Leu Ser Leu Lys
        115                 120                 125

Gln Gly Glu Leu Ser Leu Ala Val Leu Asp Leu Ala Met Ala Arg Gln
    130                 135                 140

Ala Gln Arg Gly Glu Leu Leu Lys Val Ser Tyr Lys Ala Cys Leu Pro
145                 150                 155                 160

```
Pro Ser Leu Arg Asp Leu Ile Gln Gly Ser Phe Val Thr Arg Arg Ile
            165                 170                 175
Arg Arg Thr Val Leu Leu Met Ala Lys Tyr Ile Asp Leu Glu Arg Leu
        180                 185                 190
Pro Ala Glu Phe Val Gly Leu Pro Gly Ala Gly Arg Val Gly Asp Gly
        195                 200                 205
Ile Ala Trp Gln Glu Gln Phe Cys Asp Phe Pro Glu Ile Val Asp Ser
    210                 215                 220
Ile Lys Gln Ala Pro Arg Val Gly Pro Ala Gly Glu His Arg Leu Val
225                 230                 235                 240
Thr Thr Arg Asp Ile Leu Glu Ala Glu Phe Pro Gly Leu Pro Glu Ala
            245                 250                 255
Leu Ser Phe Val Ala Leu Val Asp Gly Tyr Phe Arg Leu Asp Ser His
            260                 265                 270
Phe Phe Cys Lys Glu Val Pro Arg Leu Leu Glu Glu Ala Glu Cys His
        275                 280                 285
Gly Pro Ile Thr Leu Asp Phe Ala Ile Lys Leu Lys Gly Ser Pro Gly
    290                 295                 300
Ser Tyr Leu Arg Arg Pro Gln Asp Asp Ser Phe Leu Leu Thr Cys Val
305                 310                 315                 320
Gln Pro Leu Gly Pro Asp Tyr Lys Gly Cys Leu Ile Arg Pro Gly Phe
            325                 330                 335
Leu Val Gly Leu Ser His Ser Leu Glu Leu Leu Cys Trp Gly Leu Val
            340                 345                 350
Asp Gly Ala Leu Thr Ser Cys Cys Pro Arg Pro Lys Glu Lys Ser Asn
        355                 360                 365
Leu Ile Val Val Arg Gly Pro Thr Ser Leu Phe His Ile Pro Ala Asp
370                 375                 380
Ser Leu Glu Trp His Glu Asn Leu Gly His Gly Ser Phe Thr Lys Ile
385                 390                 395                 400
Gly Arg Glu Val Val Asp Gly Glu Thr Glu Val Leu Leu Lys Val Met
            405                 410                 415
Asp His Asn Cys Met Glu Ser Phe Leu Glu Ala Ala Ser Leu Met Ser
        420                 425                 430
Gln Val Ser Tyr His Leu Val Leu Leu His Gly Val Cys Met Ala Gly
        435                 440                 445
Asp Ser Met Val Glu Phe Val Leu Gly Ala Ile Asp Tyr Leu Arg Lys
    450                 455                 460
Arg Gly His Leu Val Pro Ala Ser Trp Lys Leu Gln Val Lys Gln Leu
465                 470                 475                 480
Ala Tyr Ala Leu Asn Tyr Leu Glu Asp Lys Gly Leu His Gly Asn Val
            485                 490                 495
Ser Ala Arg Lys Val Leu Leu Ala Arg Glu Gly Asp Gly Pro Pro Phe
        500                 505                 510
Ile Lys Leu Ser Asp Pro Gly Val Ser Pro Val Leu Ser Leu Glu Met
        515                 520                 525
Leu Thr Asp Arg Ile Pro Trp Val Ala Pro Glu Cys Leu Glu Ala Thr
        530                 535                 540
Leu Leu Glu Ala Asp Lys Trp Gly Phe Gly Ala Thr Trp Glu Val Phe
545                 550                 555                 560
Ser Gly Met Ile Leu Pro Ala Lys Lys Leu Phe Tyr Glu Asp Arg Gln
            565                 570                 575
Leu Ala Lys Trp Thr Glu Leu Leu Ile Gln Cys Met Ala Tyr Pro Arg
```

-continued

```
                580                              585                              590
    Pro  Ser  Arg  Ala  Arg  Asp  Leu  Asn  Leu  Ile  Ser  Asp  Tyr  Glu  Leu  Leu
              595                      600                      605

Ser  Asp  Thr  Pro  Arg  Asp  Leu  Gly  Ala  Gln  Leu  Tyr  Ala  Cys  Gln  Asp
         610                      615                      620

Pro  Ile  Phe  Glu  Glu  Arg  His  Leu  Lys  Tyr  Ile  Ser  Leu  Gly  Lys  Gly
    625                      630                      635                      640

Phe  Gly  Ser  Val  Glu  Leu  Cys  Arg  Tyr  Asp  Pro  Leu  Gly  Asp  Asn  Thr
                        645                      650                      655

Gly  Leu  Val  Ala  Val  Lys  Gln  Leu  Gln  His  Ser  Gly  Pro  Gln  Gln  Arg
                   660                      665                      670

Asp  Phe  Gln  Arg  Glu  Ile  Gln  Ile  Leu  Lys  Ala  His  Asp  Phe  Ile  Val
              675                      680                      685

Lys  Tyr  Arg  Gly  Val  Ser  Tyr  Gly  Pro  Gly  Arg  Gln  Leu  Val  Met  Glu
         690                      695                      700

Tyr  Leu  Pro  Ser  Gly  Cys  Leu  Arg  Asp  Phe  Leu  Gln  Arg  His  Arg  Ala
    705                      710                      715                      720

Leu  Arg  Leu  Leu  Leu  Gln  Ile  Cys  Lys  Gly  Met  Glu  Tyr  Leu  Gly  Arg
                        725                      730                      735

Arg  Cys  Val  His  Arg  Asp  Leu  Ala  Ala  Arg  Asn  Ile  Leu  Val  Glu  Ser
                   740                      745                      750

Glu  Ala  His  Val  Lys  Ile  Ala  Asp  Phe  Gly  Leu  Ala  Lys  Leu  Leu  Pro
              755                      760                      765

Leu  Lys  Asp  Tyr  Tyr  Val  Val  Arg  Pro  Gly  Gln  Ser  Pro  Ile  Phe  Trp
         770                      775                      780

Tyr  Ala  Pro  Glu  Ser  Leu  Ser  Asp  Asn  Ile  Phe  Ser  Arg  Gln  Ser  Asp
    785                      790                      795                      800

Val  Trp  Ser  Phe  Gly  Val  Val  Leu  Tyr  Glu  Leu  Phe  Thr  Tyr  Asp  Lys
                        805                      810                      815

Ser  Cys  Ser  Pro  Ser  Glu  Phe  Leu  Arg  Met  Gly  Glu  Arg  Leu  Cys  Leu
                   820                      825                      830

Leu  Glu  Leu  Leu  Glu  Gly  Arg  Leu  Pro  Pro  Cys  Pro  Glu  Val
              835                      840                      845
```